(12) United States Patent
Alvaro et al.

(10) Patent No.: US 10,934,278 B2
(45) Date of Patent: Mar. 2, 2021

(54) COMPOUNDS

(71) Applicant: Autifony Therapeutics Limited, Stevenage (GB)

(72) Inventors: Giuseppe Alvaro, Stevenage (GB); Agostino Marasco, Stevenage (GB); Guido Marconi, Stevenage (GB)

(73) Assignee: Autifony Therapeutics Limited, Stevenage (GB)

( * ) Notice: Subject to any disclaimer, the term of this patent is extended or adjusted under 35 U.S.C. 154(b) by 0 days.

(21) Appl. No.: 16/321,742

(22) PCT Filed: Jul. 28, 2017

(86) PCT No.: PCT/GB2017/052207
§ 371 (c)(1),
(2) Date: Jan. 29, 2019

(87) PCT Pub. No.: WO2018/020263
PCT Pub. Date: Feb. 1, 2018

(65) Prior Publication Data
US 2019/0161479 A1 May 30, 2019

(30) Foreign Application Priority Data

Jul. 29, 2016 (GB) ..................... 1613163

(51) Int. Cl.

| | | |
|---|---|---|
| *C07D 207/36* | (2006.01) | |
| *C07D 207/333* | (2006.01) | |
| *C07D 233/72* | (2006.01) | |
| *C07D 307/94* | (2006.01) | |
| *C07D 491/107* | (2006.01) | |
| *C07D 405/12* | (2006.01) | |
| *C07C 43/21* | (2006.01) | |
| *C07C 43/196* | (2006.01) | |
| *C07C 217/00* | (2006.01) | |
| *C07C 69/78* | (2006.01) | |
| *C07C 43/23* | (2006.01) | |
| *C07F 7/18* | (2006.01) | |
| *C07C 255/54* | (2006.01) | |
| *A61K 45/06* | (2006.01) | |
| *C07C 43/225* | (2006.01) | |
| *A61P 25/00* | (2006.01) | |

(52) U.S. Cl.
CPC ............ *C07D 405/12* (2013.01); *A61K 45/06* (2013.01); *A61P 25/00* (2018.01); *C07C 43/196* (2013.01); *C07C 43/21* (2013.01); *C07C 43/225* (2013.01); *C07C 43/23* (2013.01); *C07C 69/78* (2013.01); *C07C 217/00* (2013.01); *C07C 255/54* (2013.01); *C07D 207/333* (2013.01); *C07D 233/72* (2013.01); *C07D 307/94* (2013.01); *C07D 491/107* (2013.01); *C07F 7/1804* (2013.01); *C07C 2601/04* (2017.05)

(58) Field of Classification Search
CPC .............. C07D 207/36; C07D 207/333; C07D 233/72; C07D 307/94; C07D 491/107
See application file for complete search history.

(56) References Cited

U.S. PATENT DOCUMENTS 8,183,238 B2 * 5/2012 Claffey ................... A61P 25/24
514/235.2
2011/0098300 A1 4/2011 Sylvain et al.

FOREIGN PATENT DOCUMENTS

| WO | 2009/147149 A1 | 12/2009 |
|---|---|---|
| WO | 2011/069951 A1 | 6/2011 |
| WO | 2012/076877 A1 | 6/2012 |
| WO | 2012/168710 A1 | 12/2012 |
| WO | 2013/083994 A1 | 6/2013 |
| WO | 2013/175211 A1 | 11/2013 |
| WO | 2013/175215 A1 | 11/2013 |
| WO | 2013/182851 A1 | 12/2013 |
| WO | 2017/098254 A1 | 6/2017 |
| WO | 2017/103604 A1 | 6/2017 |

OTHER PUBLICATIONS

Database Chemical Abstracts Service, XP002774518, compounds 1873572-82-7.
Database Chemical Abstracts Service, XP002774519, compound 1870101-45-3.

\* cited by examiner

*Primary Examiner* — Rebecca L Anderson
(74) *Attorney, Agent, or Firm* — McDermott Will & Emery LLP

(57) ABSTRACT

The present invention provides compounds of the formula (I) and their use as Kv3 modulators.

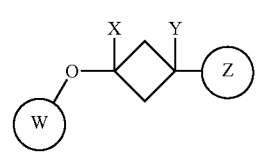

(I)

18 Claims, 6 Drawing Sheets

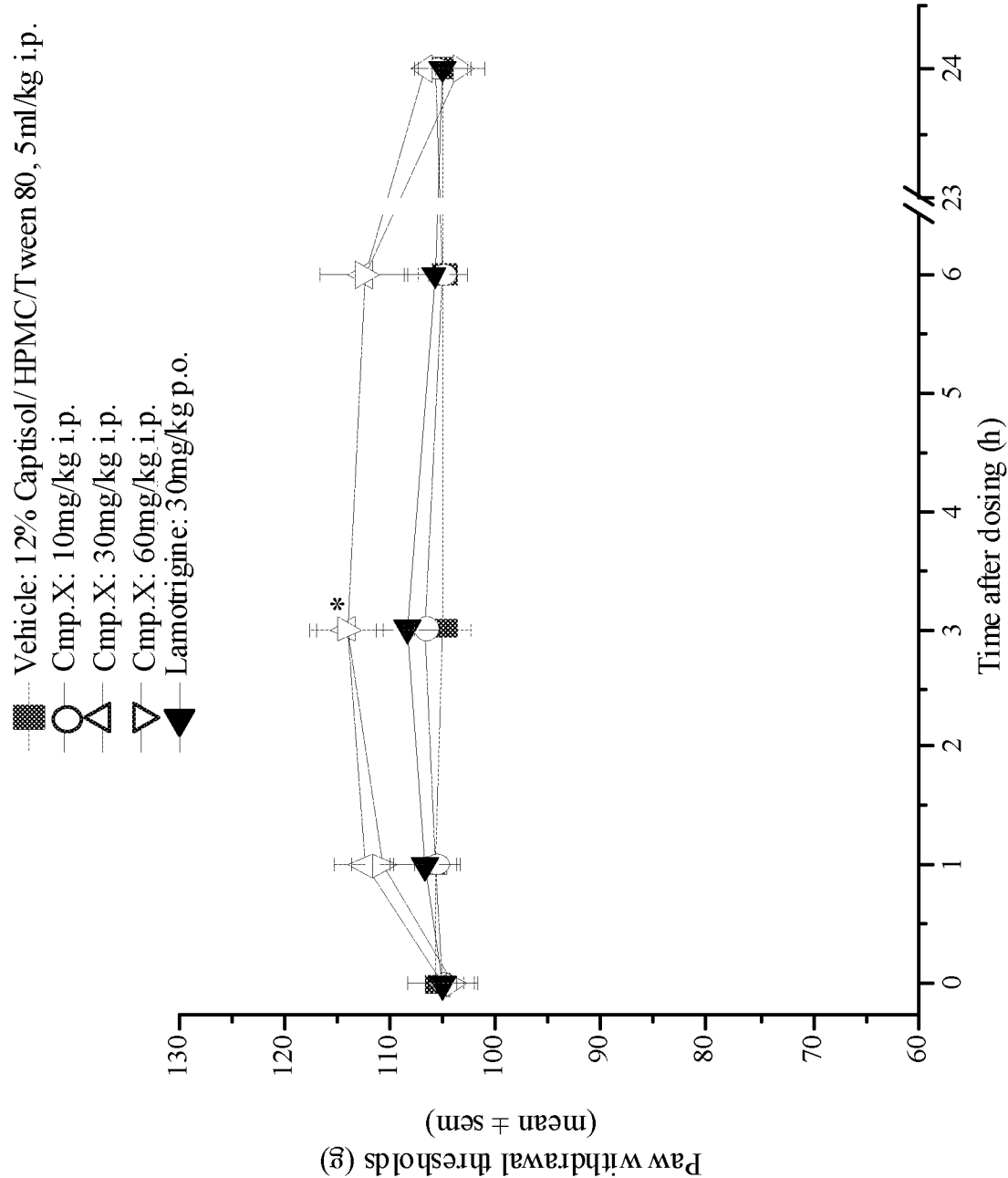

COMPOUNDS

RELATED APPLICATIONS

This application is a United States National Phase under 35 U.S.C. § 371 of International Application No. PCT/GB2017/052207, filed on Jul. 28, 2017, which claims priority to European Patent Application No. 1613163.3, filed Jul. 29, 2016.

TECHNICAL FIELD

This invention relates to novel compounds, pharmaceutical compositions containing them and their use in therapy, in particular in the prophylaxis or treatment of hearing disorders, including hearing loss and tinnitus, as well as schizophrenia, substance abuse disorders or pain such as neuropathic pain, inflammatory pain and miscellaneous pain, and in the prophylaxis of acute noise-induced hearing loss.

BACKGROUND TO THE INVENTION

The Kv3 voltage-gated potassium channel family includes four members, Kv3.1, Kv3.2, Kv3.3, and Kv3.4. Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy et al., 2001). Kv3.1-3 subtypes are predominant in the CNS, whereas Kv3.4 channels are found predominantly in skeletal muscle and sympathetic neurons (Weiser et al., 1994). Kv3.1-3 channel subtypes are differentially expressed by sub-classes of interneurons in cortical and hippocampal brain areas (e.g. Chow et al., 1999; Martina et al., 1998; McDonald et al., 2006; Chang et al., 2007), in the thalamus (e.g. Kasten et al., 2007), cerebellum (e.g. Sacco et al., 2006; Puente et al., 2010), and auditory brain stem nuclei (Li et al., 2001).

Tetraethylammonium (TEA) has been shown to inhibit the channels at low millimolar concentrations (Rudy et al., 2001), and blood-depressing substance (BDS) toxins from the sea anemone, *Anemonia sulcata* (Diochot et al., 1998), have been shown to selectively inhibit Kv3 channels with high affinity (Yeung et al., 2005).

Kv3 channels are important determinants of the function of the cerebellum, a region of the brain important for motor control (Joho et al., 2009). Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999). The deletion of Kv3.2 leads to a reduction in seizure threshold and altered cortical electroencephalographic activity (Lau et al., 2000). Deletion of Kv3.3 is associated with mild ataxia and motor deficits (McMahon et al., 2004). Double deletion of Kv3.1 and Kv3.3 gives rise to a severe phenotype characterised by spontaneous seizures, ataxia, and an increased sensitivity to the effects of ethanol (Espinosa et al., 2001; Espinosa et al., 2008). Mutations of the Kv3.3 gene in humans have been associated with forms of spinocerebellar ataxia (SCA13) (Figueroa et al., 2010).

Bipolar disorder, schizophrenia, anxiety, and epilepsy are serious disorders of the central nervous system that have been associated with reduced function of inhibitory interneurons and gamma-amino butyric acid (GABA) transmission (Reynolds et al., 2004; Benes et al., 2008; Brambilla et al., 2003; Aroniadou-Anderjaska et al., 2007; Ben-Ari, 2006). Parvalbumin positive basket cells that express Kv3 channels in the cortex and hippocampus play a key role in generating feedback inhibition within local circuits (Markram et al., 2004). Given the relative dominance of excitatory synaptic input over inhibitory input to glutamatergic pyramidal neurons in these circuits, fast-firing of interneurons supplying inhibitory input is essential to ensure balanced inhibition. Furthermore, accurate timing of inhibitory input is necessary to sustain network synchronisation, for example, in the generation of gamma frequency field potential oscillations that have been associated with cognitive function (Fisahn et al., 2005; Engel et al., 2001). Notably, a reduction in gamma oscillations has been observed in patients with schizophrenia (Spencer et al., 2004). Consequently, positive modulators of Kv3 channels might be expected to enhance the firing capabilities of specific groups of fast-firing neurons in the brain. These effects may be beneficial in disorders associated with abnormal activity of these neuronal groups. In addition, Kv3.2 channels have been shown to be expressed by neurons of the superchiasmatic nucleus (SCN) the main circadian pacemaker in the CNS (Schulz et al., 2009).

Voltage-gated ion channels of the Kv3 family are expressed at high levels in auditory brainstem nuclei (Li et al., 2001) where they permit the fast firing of neurons that transmit auditory information from the cochlear to higher brain regions. Phosphorylation of Kv3.1 and Kv3.3 channels in auditory brainstem neurons is suggested to contribute to the rapid physiological adaptation to sound levels that may play a protective role during exposure to noise (Desai et al., 2008; Song et al., 2005). Loss of Kv3.1 channel expression in central auditory neurons is observed in hearing impaired mice (von Hehn et al., 2004); furthermore, a decline in Kv3.1 expression may be associated with loss of hearing in aged mice (Jung et al. 2005), and loss of Kv3 channel function may also follow noise-trauma induced hearing loss (Pilati et al., 2012). Furthermore, pathological plasticity of auditory brainstem networks is likely to contribute to symptoms that are experienced by many people suffering from hearing loss of different types. Recent studies have shown that regulation of Kv3.1 channel function and expression has a major role in controlling auditory neuron excitability (Kaczmarek et al., 2005), suggesting that this mechanism could account for some of the plastic changes that give rise to tinnitus. Tinnitus may follow noise-induced hearing loss as a result of adaptive changes in central auditory pathways from brainstem to auditory cortex (Roberts et al., 2010). Kv3.1 and/or Kv3.2 channels are expressed in many of these circuits and contribute to the function of GABAergic inhibitory interneurons that may control the function of these circuits.

In the broadest sense, pain can be grouped in to acute pain and chronic pain. Acute pain is defined as pain that is self-limited and generally requires treatment for no more than up to a few weeks, for example postoperative or acute musculoskeletal pain, such as fractures (US Food and Drug Administration, 2014). Chronic pain can be defined either as pain persisting for longer than 1 month beyond resolution of the initial trauma, or pain persisting beyond three months. There is often no clear cause of chronic pain, and a multitude of other health problems such as fatigue, depression, insomnia, mood changes and reduction in movement, often accompany chronic pain.

Chronic pain can be sub-divided in to the following groups: neuropathic pain, chronic musculoskeletal pain and miscellaneous chronic pain. Neuropathic pain usually accompanies tissue injury and is initiated or caused by damage to the nervous system (peripheral nervous system and/or central nervous system), such as amputation, stroke, diabetes, or multiple sclerosis. Chronic musculoskeletal pain can be a symptom of diseases such as osteoarthritis and chronic lower back pain and can occur following damage to muscle tissue as well as trauma to an area for example, fractures, sprains and dislocation. Miscellaneous chronic pain encompasses all other types of long term pain and includes non-neuropathic pain conditions such as cancer pain and fibromyalgia as well as headaches and tendinitis.

Chronic pain is a highly heterogeneous condition that remains amongst the most troublesome and difficult to manage of clinical indications (McCarberg et al., 2008; Woolf 2010; Finnerup et al., 2015). Despite years of research and drug development, there has been little progress in identifying treatments that can match the opioids for efficacy without significant side effects and risk of dependence. Voltage-gated ion channels have been important targets for the management of specific pain indications, in particular neuropathic pain states. Furthermore, genetic mutations in specific ion channels have been linked to some chronic pain disorders (Bennett et al., 2014). Examples of voltage-gated ion channels that are being explored as pharmaceutical targets include: Sodium channels (*in particular NaV1.7*)—Sun et al., 2014; Dib-Hajj et al., 2013; *N-type calcium channels*—Zamponi et al., 2015; *Kv7 potassium channels*—Devulder 2010; Wickenden et al., 2009; and *SLACK*—Lu et al., 2015.

The basic hypothesis underlying these approaches is that chronic pain states are associated with increased excitability and/or aberrant firing of peripheral sensory neurons, in particular neurons involved in the transmission of painful sensory stimuli, such as the C-fibres of the dorsal root ganglia and specific circuits within the spinal cord (Baranauskas et al., 1998; Cervero 2009; Woolf et al., 2011; Baron et al., 2013). Animal models of neuropathic and inflammatory chronic pain provide the main support for this hypothesis, although demonstration of causality is still lacking (Cervero 2009).

Drugs targeting hyperexcitability, such as sodium channel blockers (e.g. CNV1014802, lamotrigine, carbamazepine, and local anaesthetics), Kv7 positive modulators (e.g. flupertine and retigabine), and N-type calcium channel modulators (e.g. gabapentin, which interacts with the α2δ subunit of the N-type calcium channel, and ziconitide, derived from a cone snail toxin) show efficacy in models of inflammatory and/or neuropathic pain. However, amongst these drugs, there is mixed evidence for clinical efficacy, for example, balancing efficacy and increased burden of side effects on the central nervous system. The disparity between efficacy in animal models and efficacy in humans is likely to be due to a range of factors, but in particular, drug concentration achievable in humans (due to poor tolerability) and heterogeneity of human pain conditions are likely to be the main culprits. For pain indications, there is also a need to identify targets through which pain relief can be achieved with reduced tolerance or tachyphylaxis and reduced abuse liability and/or risk of dependence.

Thus, improving the pharmacological management of pain is focused on mechanisms that can deliver good efficacy with a reduced side-effect burden, reduced tolerance or tachyphylaxis, and reduced abuse liability and/or risk of dependence.

Recently, Kv3.4 channels have become a target of interest for the treatment of chronic pain. Kv3.4 channels are expressed on neurons of the dorsal root ganglia (Ritter et al., 2012; Chien et al., 2007), where they are predominantly expressed on sensory C-fibres (Chien et al., 2007). Kv3 channels are also expressed by specific subsets of neurons in the spinal cord. Specifically, Kv3.1b (Deuchars et al., 2001; Brooke et al., 2002), Kv3.3 (Brooke et al., 2006), and Kv3.4 subunits (Brooke et al., 2004) have been identified in rodent spinal cord, although not always in association with circuits involved with sensory processing.

Recent animal model data suggest a down-regulation of Kv3.4 channel surface expression in DRG neurons following spinal cord injury associated with hypersensitivity to painful stimuli (Ritter et al., 2015). Similarly, it has been observed that there is a down-regulation of Kv3.4 expression in DRGs of rodents following spinal cord ligation (Chien et al., 2007). This latter study also showed that intrathecal administration to rats of an antisense oligonucleotide to suppress the expression of Kv3.4 led to hypersensitivity to mechanical stimuli. It has been shown that Kv3.4 channel inactivation could be influenced by protein kinase C-dependent phosphorylation of the channels, and that this physiological mechanism might allow DRG neurons to alter their firing characteristics in response to painful stimuli (Ritter et al., 2012). These studies suggest a causal relationship between the emergence of mechanical allodynia and reduced Kv3.4 channel expression or function. No evaluation of Kv3.1, Kv3.2, or Kv3.3 expression in SC or DRG neurons was conducted in any of these studies, and expression of these two subtypes has not been explicitly demonstrated on DRG neurons (although as mentioned above, they are abundant within specific regions of the spinal cord). The in vivo studies reported above provide a rationale for modulation of Kv3.4 as a novel approach to the treatment of certain neuropathic pain states. There are currently no data specifically linking Kv3.1 and/or Kv3.2 and/or Kv3.3 channel subtypes to pain processing.

Dementia with Lewy Bodies (DLB) and Parkinson's disease (PD) are serious neurodegenerative disorders that are associated with the accumulation of the protein, alpha-synuclein in Lewy bodies, which leads to loss of connectivity and neuronal cell death. Symptoms of DLB include progressive cognitive deficits, in particular difficulties with planning and attention. Visual hallucinations are also common, occurring in approximately 60% of patients. PD is associated initially with motor deficits, primarily due to loss of dopamine neurons. While there are currently no studies directly linking Kv3 channels to DLB or PD, the location and role of Kv3 channels, in particular Kv3.1, in cortical and basal ganglia circuits suggests that modulators of these channels could improve symptoms of DLB or PD, either alone, or in combination with current treatments, such as acetyl-cholinesterase inhibitors for DLB or L-DOPA for PD.

Patent applications WO2011/069951, WO2012/076877, WO2012/168710, WO2013/175215, WO2013/182851 and WO2017/103604 disclose compounds which are modulators of Kv3.1 and Kv3.2. Further, the utility of such compounds is demonstrated in animal models of seizure, hyperactivity, sleep disorders, psychosis, hearing disorders and bipolar disorders.

Patent application WO2013/175211 discloses that modulation of Kv3.1, Kv3.2 and/or Kv3.3 channels has been found to be beneficial in preventing or limiting the establishment of a permanent hearing loss resulting from acute noise exposure. The benefits of such prevention may be observed even after administration of the Kv3.1, Kv3.2 and/or Kv3.3 modulator has ceased.

Patent application WO2017/098254 discloses that modulation of Kv3.1, Kv3.2 and/or Kv3.3 channels has been found to be beneficial in the prophylaxis or treatment of pain, in particular neuropathic or inflammatory pain.

There remains a need for the identification of alternative modulators of Kv3.1, Kv3.2 and/or Kv3.3, in particular modulators of Kv3.1 and/or Kv3.2. Such modulators may demonstrate high in vivo potency, channel selectivity or desirable pharmacokinetic parameters, for example high brain availability, that reduces the dose required for therapeutic effect in vivo. Compounds which have balanced Kv3.1, Kv3.2 and/or Kv3.3 modulatory properties may be desirable e.g. compounds with modulate Kv3.1 and Kv3.2 to the same, or a similar extent. For certain therapeutic indications, there is also a need to identify compounds with a different modulatory effect on Kv3.1, Kv3.2 and/or Kv3.3 channels, for example, compounds that alter the kinetics of channel gating or channel inactivation, and which may behave in vivo as negative modulators of the channels.

SUMMARY OF THE INVENTION

The present invention provides a compound of formula (I):

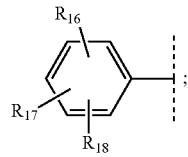

(I)

wherein:
X is H or $CH_3$;
Y is H or $CH_3$;
wherein at least one of X and Y is H;
W is group (Wa), group (Wb) or group (Wc):
wherein group (Wa) and group (Wb) are:

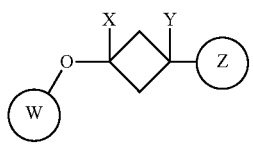

(Wa)

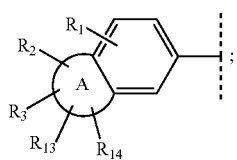

(Wb)

wherein:
$R_1$ is H, $C_{1-4}$alkyl, halo, halo$C_{1-4}$alkyl, CN, $C_{1-4}$alkoxy or halo$C_{1-4}$alkoxy;

$R_2$ is H, $C_{1-4}$alkyl, $C_{3-5}$ spiro carbocyclyl, halo$C_{1-4}$alkyl or halo;
$R_3$ is H, $C_{1-4}$alkyl, halo$C_{1-4}$alkyl, halo; or $R_3$ is absent;
$R_{13}$ is H, $C_{1-4}$alkyl, halo$C_{1-4}$alkyl, halo; or $R_{13}$ is absent;
$R_{14}$ is H, $C_{1-4}$alkyl, halo$C_{1-4}$alkyl, halo; or $R_{14}$ is absent;
A is a 5 or 6 membered saturated or unsaturated heterocycle, with at least one 0 atom; which heterocycle is optionally fused with a cyclopropyl group, or a cyclobutyl group, or a cyclopentyl group to form a tricycle when considered together with the phenyl;
wherein $R_2$ and $R_3$ may be attached to the same or a different ring atom; $R_2$ may be attached to a fused ring atom; and wherein $R_{13}$ and $R_{14}$ may be attached to the same or a different ring atom;
wherein group (Wc) is:

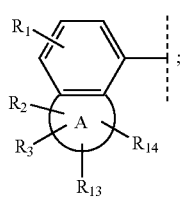

(Wc)

wherein:
$R_{16}$ is halo, $C_{1-4}$alkyl, $C_{1-4}$alkoxy, halo$C_{1-4}$alkyl, halo$C_{1-4}$alkoxy or CN;
$R_{17}$ is H, halo, CN, $C_{1-4}$alkyl, $C_{1-4}$alkoxy or halo $C_{1-4}$alkoxy;
$R_{18}$ is H, halo, CN, $C_{1-4}$alkyl or $C_{1-4}$alkoxy;
Z is group (Za) or (Zb):
wherein group (Za) is:

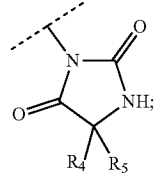

(Za)

wherein:
$R_4$ is H or $C_{1-4}$ alkyl;
$R_5$ is H or $C_{1-4}$ alkyl; or
$R_4$ and $R_5$ can be fused to form a $C_{3-5}$ spiro carbocyclyl or a $C_{2-5}$ spiro heterocyclyl;
and wherein group (Zb) is:

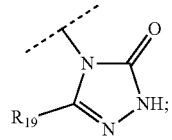

(Zb)

wherein:
$R_{19}$ is $C_{1-4}$ alkyl.

In particular, compounds are provided wherein $R_4$ is $C_{1-4}$ alkyl; $R_5$ is H or $C_{1-4}$ alkyl; or $R_4$ and $R_5$ can be fused to form a $C_{3-5}$ spiro carbocyclyl or a $C_{2-4}$ spiro heterocyclyl.

A compound of formula (I) may be provided in the form of a pharmaceutically acceptable salt and/or solvate thereof and/or derivative thereof. In one embodiment, the compound of formula (I) is provided in the form of a pharmaceutically acceptable salt.

The compounds of formula (I) may be used as medicaments, in particular for use in the prophylaxis or treatment of hearing disorders, including hearing loss and tinnitus, as well as schizophrenia, substance abuse disorders or pain such as neuropathic pain, inflammatory pain and miscellaneous pain. Compounds of formula (I) may also be used in the prophylaxis of acute noise-induced hearing loss.

Further, there is provided a method for the prophylaxis or treatment of hearing disorders, including hearing loss and tinnitus, as well as hearing disorders, including hearing loss and tinnitus, as well as schizophrenia, substance abuse disorders or pain such as neuropathic pain, inflammatory pain and miscellaneous pain, by administering to a subject in need thereof a compound of formula (I). A method of prophylaxis of acute noise-induced hearing loss, by administering to a subject a compound of formula (I) is also provided.

Compounds of formula (I) may be used in the manufacture of a medicament for the prophylaxis or treatment of hearing disorders, including hearing loss and tinnitus, as well as schizophrenia, substance abuse disorders or pain such as neuropathic pain, inflammatory pain and miscellaneous pain. Further, compounds of formula (I) may be used in the manufacture of a medicament for the prophylaxis of acute noise-induced hearing loss.

Also provided are pharmaceutical compositions containing a compound of formula (I) and a pharmaceutically acceptable carrier or excipient.

Also provided are processes for preparing compounds of formula (I) and novel intermediates of use in the preparation of compounds of formula (I).

Additionally provided are prodrug derivatives of the compounds of formula (I).

DETAILED DESCRIPTION OF THE INVENTION

Figure 1A:
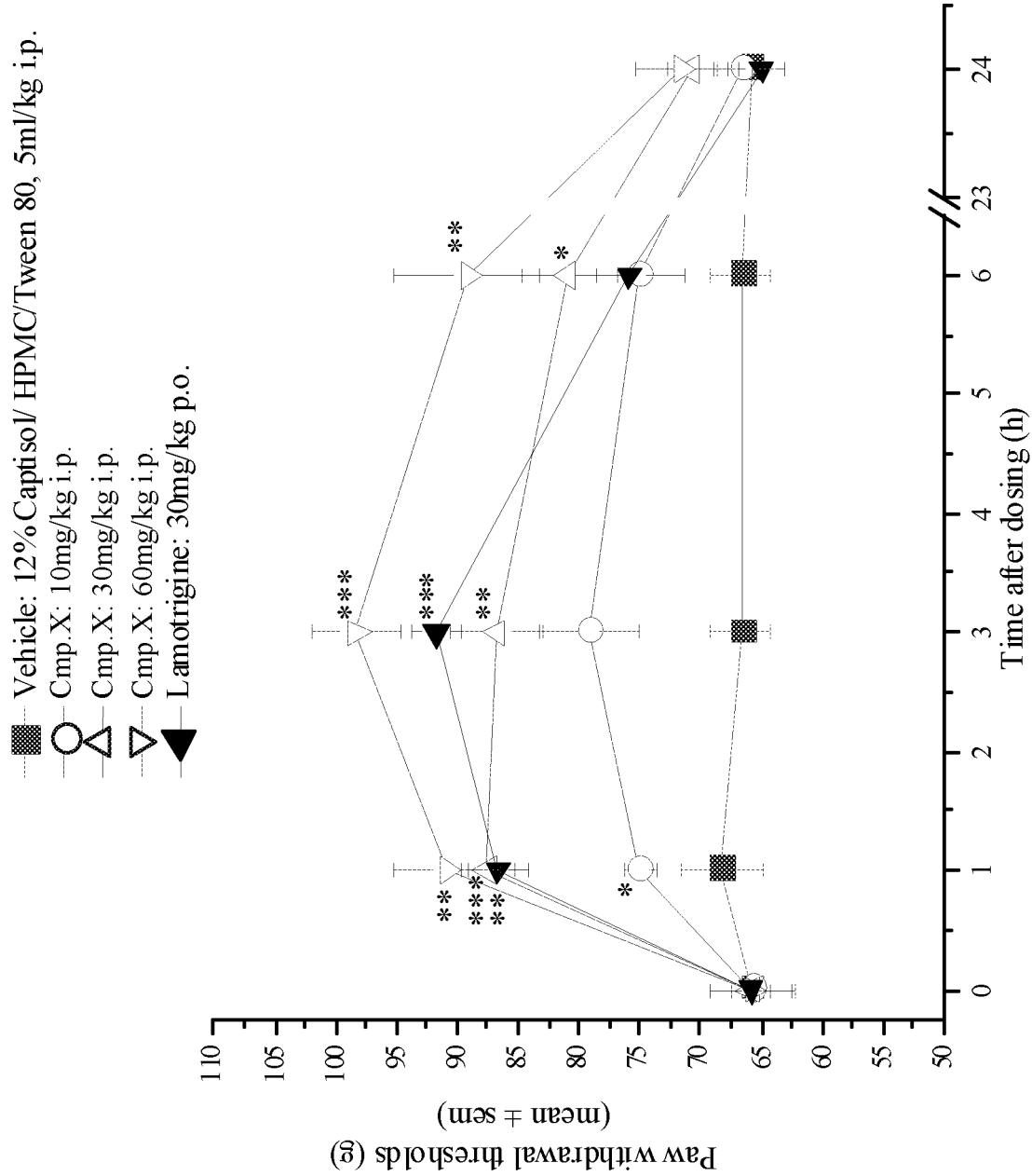
FIG. 1 shows the effect of Compound X on paw withdrawal thresholds under mechanical pressure in a neuropathic pain model: ipsilateral paw (FIG. 1a); contralateral paw (FIG. 1b); and percentage reversals (FIG. 1c).

The present invention provides a compound of formula (I):

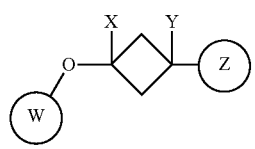

(I)

wherein:

X is H or $CH_3$;

Y is H or $CH_3$;

wherein at least one of X and Y is H;

W is group (Wa), group (Wb) or group (Wc):

wherein group (Wa) and group (Wb) are:

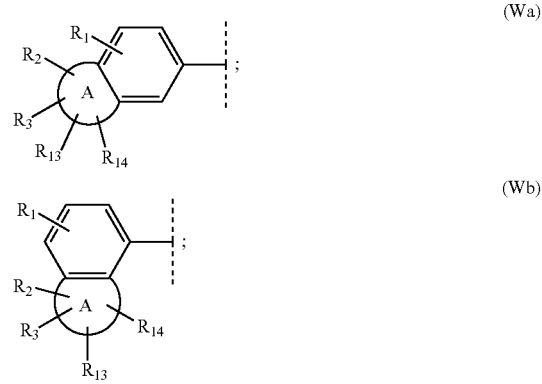

wherein:

$R_1$ is H, $C_{1-4}$alkyl, halo, halo$C_{1-4}$alkyl, CN, $C_{1-4}$alkoxy or halo$C_{1-4}$alkoxy;

$R_2$ is H, $C_{1-4}$alkyl, $C_{3-5}$ spiro carbocyclyl, halo$C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

$R_{14}$ is H, $C_{1-4}$alkyl, halo$C_{1-4}$alkyl, halo; or $R_{14}$ is absent;

A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;

wherein $R_2$ and $R_3$ may be attached to the same or a different ring atom; $R_2$ may be attached to a fused ring atom; and wherein $R_{13}$ and $R_{14}$ may be attached to the same or a different ring atom;

wherein group (Wc) is:

wherein:

$R_{16}$ is halo, $C_{1-4}$alkyl, $C_{1-4}$alkoxy, halo$C_{1-4}$alkyl, halo$C_{1-4}$alkoxy or CN;

$R_{17}$ is H, halo, CN, $C_{1-4}$alkyl, $C_{1-4}$alkoxy or halo $C_{1-4}$alkoxy;

$R_{18}$ is H, halo, CN, $C_{1-4}$alkyl or $C_{1-4}$alkoxy;

Z is group (Za) or (Zb):
wherein group (Za) is:

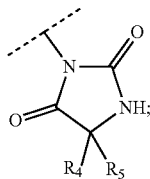

(Za)

wherein:
R$_4$ is H or C$_{1-4}$ alkyl;
R$_5$ is H or C$_{1-4}$ alkyl; or
R$_4$ and R$_5$ can be fused to form a C$_{3-5}$ spiro carbocyclyl or a C$_{2-5}$ spiro heterocyclyl;
and wherein group (Zb) is:

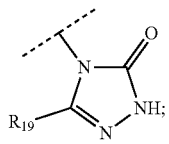

(Zb)

wherein:
R$_{19}$ is C$_{1-4}$ alkyl;
or a pharmaceutically acceptable salt and/or solvate thereof and/or derivative thereof.

The present invention also provides a compound of formula (I):

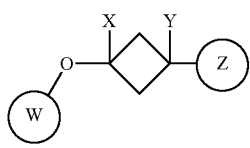

(I)

wherein:
X is H or CH$_3$;
Y is H or CH$_3$;
wherein at least one of X and Y is H;
W is group (Wa), group (Wb) or group (Wc):
  wherein group (Wa) and group (Wb) are:

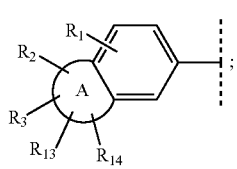

(Wa)

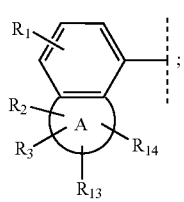

(Wb)

wherein:
R$_1$ is H, C$_{1-4}$alkyl, halo, haloC$_{1-4}$alkyl, CN, C$_{1-4}$alkoxy or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;
wherein group (Wc) is:

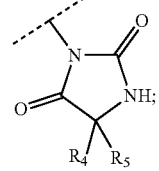

(Wc)

wherein:
R$_{16}$ is halo, C$_{1-4}$alkyl, C$_{1-4}$alkoxy, haloC$_{1-4}$alkyl, haloC$_{1-4}$alkoxy or CN;
R$_{17}$ is H, halo, CN, C$_{1-4}$alkyl, C$_{1-4}$alkoxy or haloC$_{1-4}$alkoxy;
R$_{18}$ is H, halo, CN, C$_{1-4}$alkyl or C$_{1-4}$alkoxy;
Z is group (Za) or (Zb):
  wherein group (Za) is:

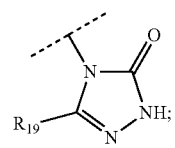

(Za)

wherein:
R$_4$ is C$_{1-4}$ alkyl;
R$_5$ is H or C$_{1-4}$ alkyl; or
R$_4$ and R$_5$ can be fused to form a C$_{3-5}$ spiro carbocyclyl or a C$_{2-4}$ spiro heterocyclyl; and wherein group (Zb) is:

(Zb)

wherein:

$R_{19}$ is $C_{1-4}$ alkyl;

or a pharmaceutically acceptable salt and/or solvate thereof and/or derivative thereof.

Embodiments set out below relating to relative stereochemistry and the nature of groups, including A, X, Y, W, (Wa), (Wb), (Wc), (Wc-a), (Wc-b), Z, (Za), (Zb), R', R", $R_1$, $R_2$, $R_3$, $R_4$, $R_5$, $R_{13}$, $R_{14}$, $R_{16}$, $R_{17}$, $R_{18}$, $R_{19}$, $R_{20}$, $R_{21}$, $R_{22}$, $R_{23}$, $R_{24}$, $R_{30}$ and $R_{31}$ are envisaged as being independently, fully combinable with one another to form further embodiments of the invention. Such embodiments apply equally to intermediates which may be of use in the synthesis of a compound of formula (I) e.g. compounds of formulae (II) and (XII).

Reference to a compound of formula (I) also applies to a compound of formulae (Iab), (Iac), (Ia), (Ib), (Ic), (I-I), I-Iab), I-Iac), (Ia-I), (Ib-I), (Ic-I), (I-II), (I-IIab), (I-IIac), (Ia-II), (Ib-II), (Ic-II), (I-III), (I-IIab), (I-IIac), (Ia-III), (Ib-III), (Ic-III), (I-IV), (I-IVab), (I-IVac), (Ia-IV), (Ib-IV), (Ic-IV), (I-V), (I-Vab), (I-Vac), (Ia-V), (Ib-V), (Ic-V), (IA), (IaA), (IbA), (IcA), (IB), (IaB), (IbB), (IcB), (IC), (IaC), (IbC), (IcC), (ID), (IaD), (IbD), (IcD), (IE), (IaE), (IbE), (IcE), (IF), (IaF), (IbF) and (IcF) unless otherwise stated, and where appropriate to the circumstances (i.e. where chemically sensible).

In all compounds of formula (I), the following group represents a cyclobutyl moiety:

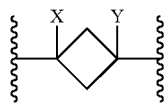

Groups W and Z may be on the same face of the cyclobutyl moiety, i.e. in a syn arrangement, or on opposite faces of the cyclobutyl ring i.e. in an anti arrangement:

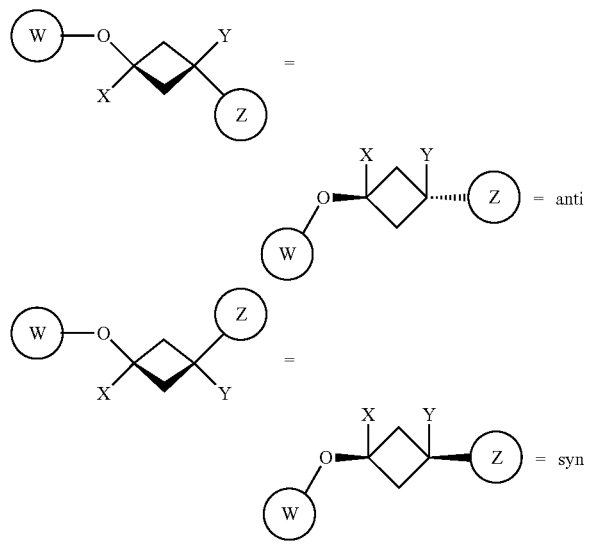

In one embodiment, the compound of formula (I) has syn configuration. Suitably the compound of formula (I) has anti configuration. Compounds of formula (I) with anti configuration typically have increased potency at Kv3.1 compared with the equivalent compounds of syn configuration.

X is H or $CH_3$ and Y is H or $CH_3$, but at least one of X and Y is H. In one embodiment, X and Y are both H. In one embodiment, X is H and Y is $CH_3$. In one embodiment, X is $CH_3$ and Y is H.

Group Z may be group (Za) or group (Zb). In one embodiment, group Z is group (Za). In one embodiment, group Z is group (Zb).

Group (Za) is a hydantoin moiety bearing substituents $R_4$ and $R_5$. In one embodiment, $R_4$ is methyl, ethyl, isopropyl or tert-butyl, in particular methyl. In one embodiment, $R_5$ is $C_{1-4}$ alkyl such as methyl, ethyl, isopropyl or tert-butyl. In one embodiment, $R_5$ is H. In one embodiment $R_4$ is H. In one embodiment, $R_4$ and $R_5$ are fused to form a $C_{3-4}$ spiro carbocyclyl. In one embodiment, $R_4$ and $R_5$ are fused to form a $C_{2-4}$ spiro heterocyclyl containing one heteroatom which is suitably O or N, e.g. oxetane. Suitably $R_4$ and $R_5$ are fused to form a $C_{3-5}$ spiro heterocyclyl containing O, namely oxetane, tetrahydrofuran or tetrahydropyran.

Suitably $R_4$ is H, methyl or ethyl, and $R_5$ is independently H, methyl or ethyl.

In one embodiment, $R_4$ is $C_{1-4}$ alkyl such as methyl, ethyl, isopropyl or tert-butyl, and $R_5$ is H. In one embodiment, $R_4$ is $C_{1-4}$ alkyl such as methyl, ethyl, isopropyl or tert-butyl, and $R_5$ is $C_{1-4}$ alkyl such as methyl, ethyl, isopropyl or tert-butyl. In this embodiment, $R_4$ and $R_5$ may be the same or different. In one embodiment, $R_4$ and $R_5$ are both methyl or both ethyl. In one embodiment, one of $R_4$ and $R_5$ is methyl and the remaining $R_4$ or $R_5$ is ethyl. In one embodiment $R_4$ is H and $R_5$ is H.

In embodiments wherein $R_4$ and $R_5$ are different, they may have the following stereochemical arrangement:

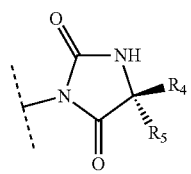

In this embodiment, for example, $R_4$ is $C_{1-4}$ alkyl such as methyl, ethyl, isopropyl or tert-butyl, and $R_5$ is H. Alternatively, $R_4$ may be $C_{2-4}$ alkyl such as ethyl, isopropyl or tert-butyl, and $R_5$ is $C_{1-3}$ alkyl such as methyl, ethyl or isopropyl, but $R_4$ contains a greater number of carbon atoms than $R_5$.

In embodiments wherein $R_4$ and $R_5$ are different, they may alternatively have the following stereochemical arrangement:

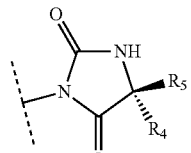

In this embodiment, for example, $R_4$ is $C_{1-4}$ alkyl such as methyl, ethyl, isopropyl or tert-butyl, and $R_5$ is H. Alternatively, $R_4$ may be $C_{2-4}$ alkyl such as ethyl, isopropyl or tert-butyl, and $R_5$ is $C_{1-3}$ alkyl such as methyl, ethyl or isopropyl, but $R_4$ contains a greater number of carbon atoms than $R_5$.

Group (Zb) is a triazolone moiety bearing substituent $R_{19}$. $R_{19}$ is $C_{1-4}$ alkyl such as methyl, ethyl, isopropyl or tert-butyl, suitably $R_{19}$ is methyl or ethyl, in particular methyl.

Group W is group (Wa), group (Wb) or group (Wc). In one embodiment, group W is group (Wa). In one embodiment, group W is group (Wb). In one embodiment, group W is group (Wc).

Groups (Wa) and (Wb) both contain ring A and bear substituents $R_1$, $R_2$, $R_3$, $R_{13}$ and $R_{14}$.

In one embodiment, ring A is a 5 membered saturated heterocycle, with at least one O atom; which heterocycle is optionally fused with a cyclopropyl group, or a cyclobutyl group, or a cyclopentyl group to form a tricycle when considered together with the phenyl. In one embodiment, ring A contains one heteroatom which is oxygen. In one embodiment, ring A contains two heteroatoms, e.g. two oxygen atoms or one oxygen atom and one nitrogen atom.

In one embodiment ring A is dihydrofuran, isoxazole, dihydropyran, 1,3-dioxolane, 1,3-oxazine or dihydropyran. Suitably, ring A is dihydrofuran or dihydropyran, in particular dihydrofuran.

In one embodiment, ring A is selected from the group consisting of:

1
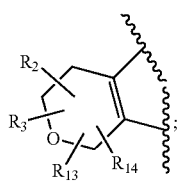

2
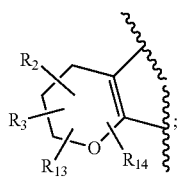

3
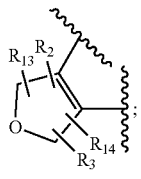

4
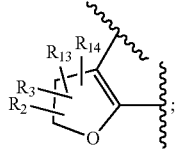

5
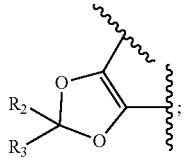

6
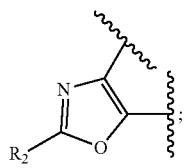

7
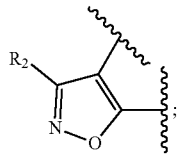

8
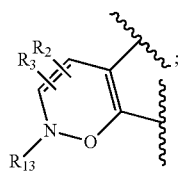

9
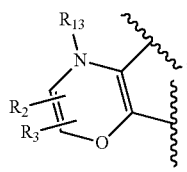

10
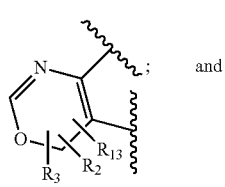
and

11
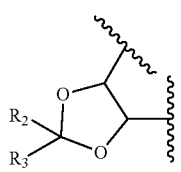

wherein

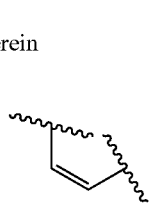

denotes a point at which ring A is fused to the phenyl ring.

In one embodiment, ring A is selected from the group consisting of:

1
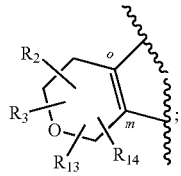

-continued
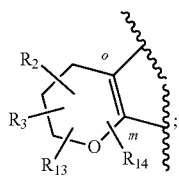
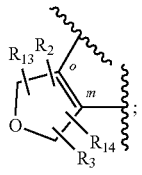
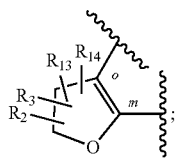
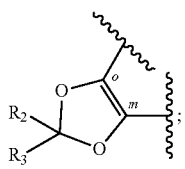
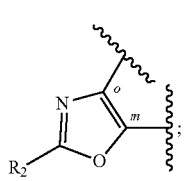
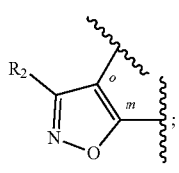
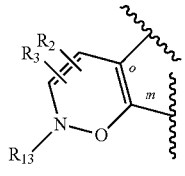
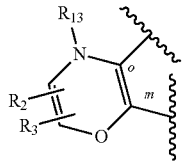
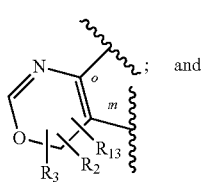 and
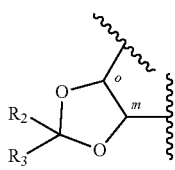
wherein
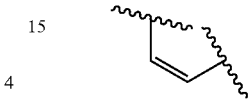
denotes a point at which ring A is fused to the phenyl ring, and "o" and "m" indicate the ortho- and meta-positions of the phenyl ring to which group A is fused.
In one embodiment, ring A is selected from the group consisting of:
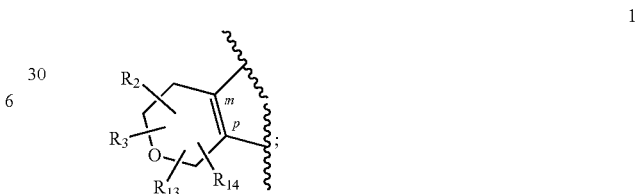
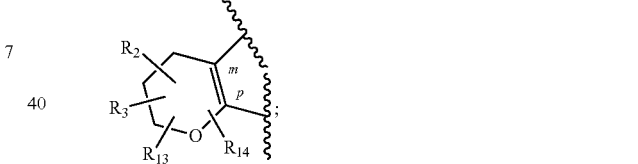
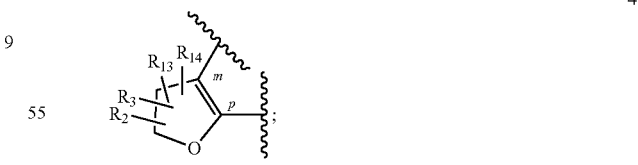
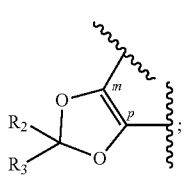

-continued
6
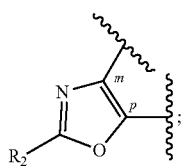
7
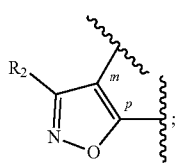
8
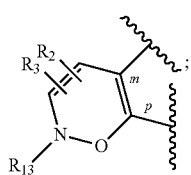
9
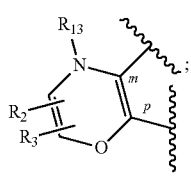
10
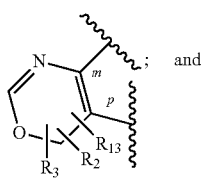; and
11
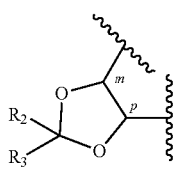
wherein
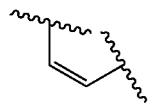 [SMILES: */C=C\*]
denotes a point at which ring A is fused to the phenyl ring, wherein "m" and "p" indicate the meta- and para-positions of the phenyl ring to which group A is fused.
Suitably, ring A is:
1
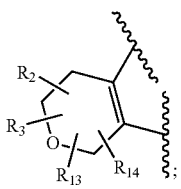;
2
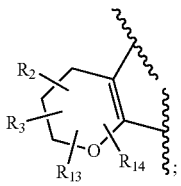;
3
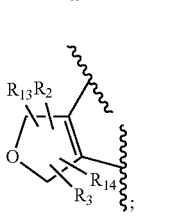;
4
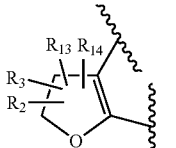 or
11
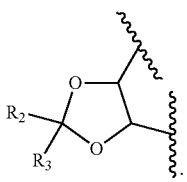.
Suitably, ring A is:
1
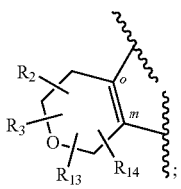;
2
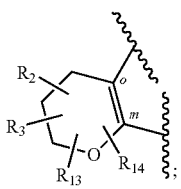;

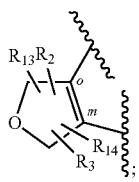
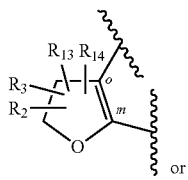
or
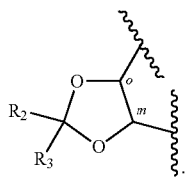
Suitably, ring A is:
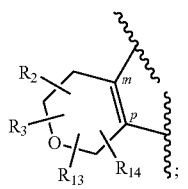
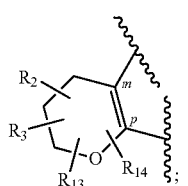
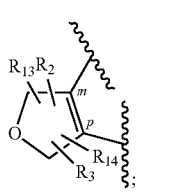
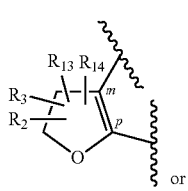
or
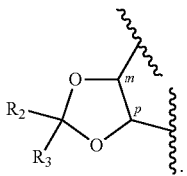
In particular, ring A is
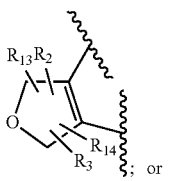
or
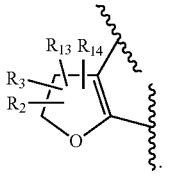
In particular, ring A is
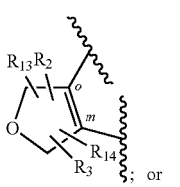
or
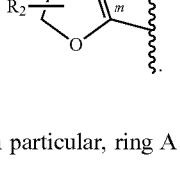
In particular, ring A is
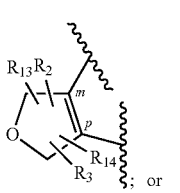
or

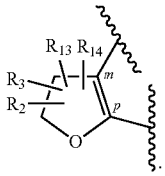

In one embodiment, when ring A is a 5 membered heterocycle containing one heteroatom which is oxygen, wherein suitably the oxygen atom is located at the phenolic position relative to the phenyl ring.

In one embodiment, $R_1$ is H, $C_{1-4}$alkyl, halo halo$C_{1-4}$alkyl or CN, in particular $C_{1-4}$alkyl such as methyl. In one embodiment $R_1$ is H, methyl or CN. In one embodiment $R_1$ is methyl. In one embodiment, $R_1$ is CN. In one embodiment $R_1$ is $C_{1-4}$alkoxy, in particular methoxy or ethoxy such as methyl. In one embodiment, $R_1$ is H.

In one embodiment, when W is group (Wb) $R_1$ is at the para position and is not H:

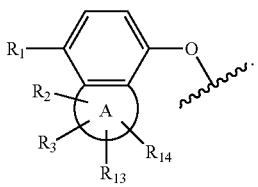

In one embodiment, when W is group (Wb) $R_1$ is at the meta position and is not H:

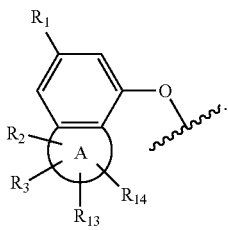

In one embodiment, when W is group (Wb) $R_1$ is at the ortho position and is not H:

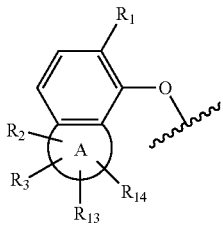

In one embodiment, $R_2$ is H, $C_{1-4}$alkyl, $C_{3-5}$spiro carbocyclyl or halo. In one embodiment, $R_2$ is $C_{1-4}$ alkyl such as methyl or ethyl or $C_{3-5}$spiro carbocyclyl such as $C_3$ spiro carbocycle. In one embodiment, $R_2$ is methyl. In one embodiment, $R_2$ is halo e.g. fluoro.

In one embodiment, $R_3$ is H, $C_{1-4}$alkyl, halo$C_{1-4}$alkyl or halo. In one embodiment, $R_3$ is $C_{1-4}$alkyl such as methyl. In another embodiment $R_3$ is halo e.g. fluoro. In another embodiment $R_3$ is absent.

In one embodiment, $R_2$ and $R_3$ are located on the same ring A atom.

In one embodiment, $R_{13}$ is H or is absent. Suitably, $R_{13}$ is absent.

In one embodiment, $R_{14}$ is H or is absent. Suitably, $R_{14}$ is absent.

Group (Wc) bears substituents $R_{16}$, $R_{17}$, and $R_{18}$.

In one embodiment, $R_{16}$ is not in the para position. In one embodiment, one of $R_{17}$ and $R_{18}$ is not H.

In one embodiment, $R_{16}$ is $C_{1-4}$alkyl, $C_{1-4}$alkoxy, halo $C_{1-4}$alkyl, halo$C_{1-4}$alkoxy or CN. In one embodiment, $R_{16}$ is $C_{1-4}$alkyl, $C_{1-4}$alkoxy, halo$C_{1-4}$alkyl or halo$C_{1-4}$alkoxy. In one embodiment, $R_{16}$ is $C_{1-4}$alkyl, $C_{1-4}$alkoxy or halo $C_{1-4}$alkoxy. In one embodiment, $R_{16}$ is halo, $C_{1-4}$alkyl or $C_{1-4}$alkoxy. In one embodiment, $R_{16}$ is methyl, ethyl, propyl, butyl, cyclopropyl, chloro, fluoro, methoxy, ethoxy, propoxy, trifluoromethyl, trifluoromethoxy or CN.

In one embodiment, $R_{17}$ is H, halo, CN, $C_{1-4}$alkyl or $C_{1-4}$alkoxy. In one embodiment, $R_{17}$ is H, CN, $C_{1-4}$alkyl, $C_{1-4}$alkoxy or halo$C_{1-4}$alkoxy. In one embodiment, $R_{17}$ is $C_{1-4}$alkyl or $C_{1-4}$alkoxy. In one embodiment, $R_{17}$ is H, CN or $C_{1-4}$alkyl. In one embodiment, $R_{17}$ is H, CN or methyl. In one embodiment, $R_{17}$ is methyl, ethyl, propyl, butyl, cyclopropyl, chloro, fluoro, methoxy, ethoxy, propoxy, trifluoromethoxy or CN.

In one embodiment, $R_{18}$ is H.

In one embodiment, $R_{17}$ and $R_{18}$ are H. In this embodiment, $R_{16}$ is suitably at the ortho- or meta-position. In this embodiment, when $R_{16}$ is at the ortho position, it is suitably $C_{1-4}$ alkyl, for example methyl, ethyl, n-propyl, isopropyl, cyclopropyl, n-butyl or tert-butyl. In one embodiment, when $R_{16}$ is at the meta position, it is suitably $C_{1-4}$alkyl for example methyl, ethyl, isopropyl or cyclopropyl; $C_{1-4}$alkoxy for example methoxy or ethoxy; or halo$C_{1-4}$alkoxy for example trifluoromethoxy.

In one embodiment, when the compound of formula (I) has syn configuration and $R_{16}$ is at the ortho position, $R_{16}$ is not tert-butyl.

In one embodiment, $R_{18}$ is H and $R_{17}$ is not H. When this is the case, in one embodiment one of $R_{16}$ or $R_{17}$ is at the ortho position. In this embodiment, the substituent at the ortho position is suitably $C_{1-4}$ alkyl, for example methyl, ethyl, n-propyl, isopropyl, cyclopropyl, n-butyl or tert-butyl. In another embodiment, one of $R_{16}$ and $R_{17}$ is at the ortho-position, and the other is at the meta-position. In this embodiment, the substituent at the ortho position is suitably $C_{1-4}$ alkyl, for example methyl, ethyl, n-propyl, isopropyl, cyclopropyl, n-butyl or tert-butyl and the substituent at the meta position is suitably $C_{1-4}$alkyl for example methyl, ethyl, isopropyl or cyclopropyl; $C_{1-4}$alkoxy for example methoxy or ethoxy; or halo$C_{1-4}$alkoxy for example trifluoromethoxy. In one embodiment, one of $R_{16}$ and $R_{17}$ is at position 1-, and the other is at position 4-. In one embodiment, one of $R_{16}$ and $R_{17}$ is at the ortho-position, and the other is at the para-position. In this embodiment, the substituent in the para position is suitably CN, fluoro or methyl. In one embodiment, both of $R_{16}$ and $R_{17}$ are at the ortho-positions. In this embodiment, the substituents at the ortho position are suitably the same, and are suitably $C_{1-4}$ alkyl, for example methyl, ethyl, n-propyl, isopropyl, cyclopropyl, n-butyl or tert-butyl.

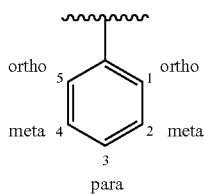

In one embodiment, when group Z is (Za), then when W is group (Wc) it is of formula (Wc-a):

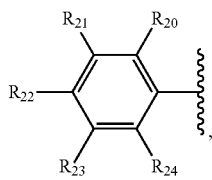

(Wc-a)

wherein
$R_{20}$ is H, $C_{1-4}$alkyl, halo$C_{1-4}$alkyl, or CN;
$R_{21}$ is H, halo, $C_{1-4}$alkyl, $C_{1-4}$alkoxy, halo$C_{1-4}$alkyl, halo $C_{1-4}$alkoxy or CN;
$R_{22}$ is H, halo, $C_{1-4}$alkyl, halo$C_{1-4}$alkyl, or CN;
$R_{23}$ is H, halo, $C_{1-4}$alkyl, $C_{1-4}$alkoxy, halo$C_{1-4}$alkyl or halo$C_{1-4}$alkoxy;
$R_{24}$ is H, $C_{1-4}$alkyl, halo$C_{1-4}$alkyl, or CN;
wherein at least 2, and suitably 3, of $R_{20}$, $R_{21}$, $R_{22}$, $R_{23}$ and $R_{24}$ are H,
and wherein at least one of $R_{20}$, $R_{21}$, $R_{22}$, $R_{23}$ and $R_{24}$ is not H.

In one embodiment, when group Z is (Zb), when W is group (Wc) it is of formula (Wc-a):

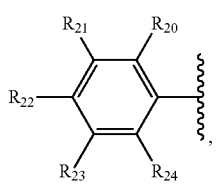

(Wc-a)

wherein
$R_{20}$ is H, $C_{1-4}$alkyl, halo$C_{1-4}$alkyl, or CN;
$R_{21}$ is H, halo, $C_{1-4}$alkyl, $C_{1-4}$alkoxy, halo$C_{1-4}$alkyl, halo $C_{1-4}$alkoxy or CN;
$R_{22}$ is H, halo, $C_{1-4}$alkyl, halo$C_{1-4}$alkyl, or CN;
$R_{23}$ is H, halo, $C_{1-4}$alkyl, $C_{1-4}$alkoxy, halo$C_{1-4}$alkyl or halo$C_{1-4}$alkoxy;
$R_{24}$ is H, $C_{1-4}$alkyl, halo$C_{1-4}$alkyl, or CN;
wherein at least 2, and suitably 3, of $R_{20}$, $R_{21}$, $R_{22}$, $R_{23}$ and $R_{24}$ are H;
and wherein at least one of $R_{20}$, $R_{21}$, $R_{22}$, $R_{23}$ and $R_{24}$ is not H.

It should be noted that compounds of formula (Wc-a) are intended to fall within the scope of formula (Wc), therefore the substituents $R^{20}$-$R^{24}$ are further limited in so far as the resulting phenyl group must fall within formula (Wc).

In one embodiment, Y is H and the compound is a compound of formula (Iab):

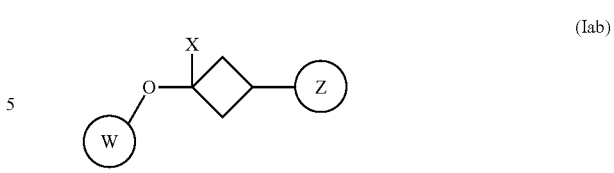

(Iab)

wherein W, X and Z are as defined above, or a pharmaceutically acceptable salt and/or solvate thereof and/or derivative thereof.

In one embodiment, X is H and the compound is a compound of formula (Iac):

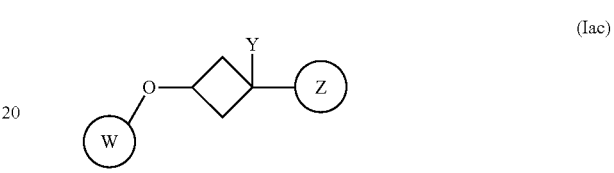

(Iac)

wherein W, Y and Z are as defined above, or a pharmaceutically acceptable salt and/or solvate thereof and/or derivative thereof.

In one embodiment, X and Y are H and the compound is a compound of formula (Ia):

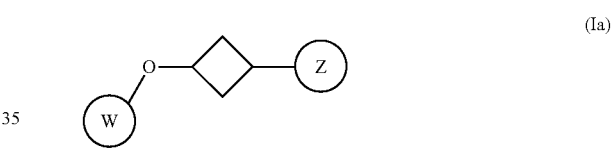

(Ia)

wherein W and Z are as defined above, or a pharmaceutically acceptable salt and/or solvate thereof and/or derivative thereof.

In one embodiment, X is $CH_3$ and Y is H and the compound is a compound of formula (Ib):

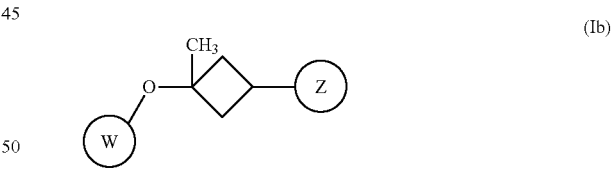

(Ib)

wherein W and Z are as defined above, or a pharmaceutically acceptable salt and/or solvate thereof and/or derivative thereof.

In one embodiment, X is H and Y is $CH_3$ and the compound is a compound of formula (Ic):

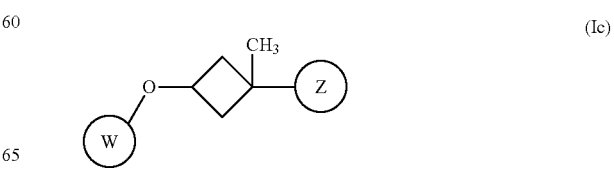

(Ic)

wherein W and Z are as defined above, or a pharmaceutically acceptable salt and/or solvate thereof and/or derivative thereof.

In one embodiment, the compound is a compound of formula (I-I):

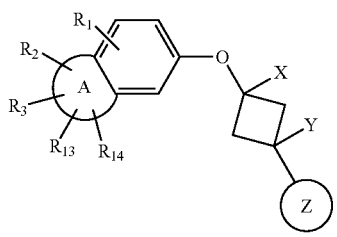
(I-I)

or a pharmaceutically acceptable salt and/or solvate thereof and/or derivative thereof, wherein $R_1$, $R_2$, $R_3$, $R_{13}$, $R_{14}$, A, X, Y and Z are as defined above.

In one embodiment, Y is H and the compound is a compound of formula (I-Iab):

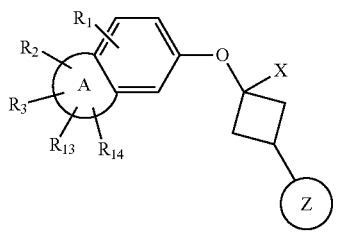
(I-Iab)

or a pharmaceutically acceptable salt and/or solvate thereof and/or derivative thereof, wherein $R_1$, $R_2$, $R_3$, $R_{13}$, $R_{14}$, A, X and Z are as defined above.

In one embodiment, X is H and the compound is a compound of formula I-Iac):

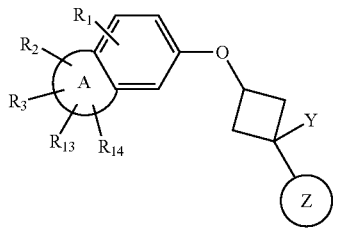
(I-Iac)

or a pharmaceutically acceptable salt and/or solvate thereof and/or derivative thereof, wherein $R_1$, $R_2$, $R_3$, $R_{13}$, $R_{14}$, A, Y and Z are as defined above.

In one embodiment, the compound is a compound of formula (Ia-I):

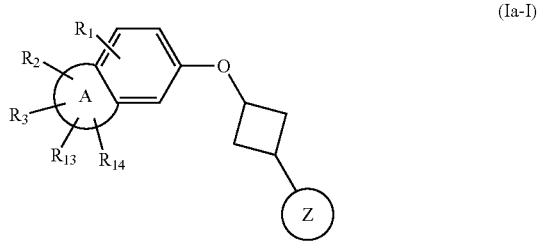
(Ia-I)

or a pharmaceutically acceptable salt and/or solvate thereof and/or derivative thereof, wherein $R_1$, $R_2$, $R_3$, $R_{13}$, $R_{14}$, A and Z are as defined above.

In one embodiment, the compound is a compound of formula (Ib-1): In one embodiment, the compound is a compound of formula (Ib-I):

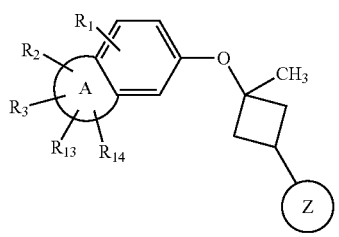
(Ib-1)

or a pharmaceutically acceptable salt and/or solvate thereof and/or derivative thereof, wherein $R_1$, $R_2$, $R_3$, $R_{13}$, $R_{14}$, A and Z are as defined above.

In one embodiment, the compound is a compound of formula (Ic-I):

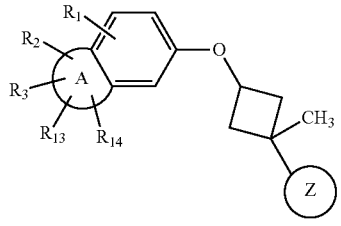
(Ic-1)

or a pharmaceutically acceptable salt and/or solvate thereof and/or derivative thereof, wherein $R_1$, $R_2$, $R_3$, $R_{13}$, $R_{14}$, A and Z are as defined above.

In one embodiment, the compound is a compound of formula (I-II):

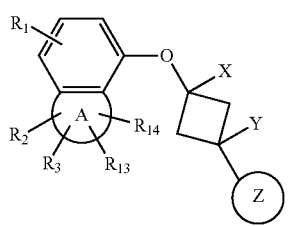
(I-II)

or a pharmaceutically acceptable salt and/or solvate thereof and/or derivative thereof, wherein $R_1$, $R_2$, $R_3$, $R_{13}$, $R_{14}$, A, X, Y and Z are as defined above.

In one embodiment, the compound is a compound of formula (I-IIab):

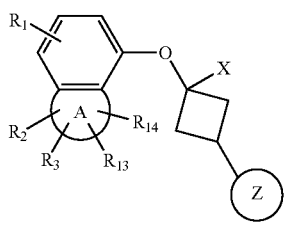
(I-IIab)

or a pharmaceutically acceptable salt and/or solvate thereof and/or derivative thereof, wherein $R_1$, $R_2$, $R_3$, $R_{13}$, $R_{14}$, A, X and Z are as defined above.

In one embodiment, the compound is a compound of formula (I-IIac):

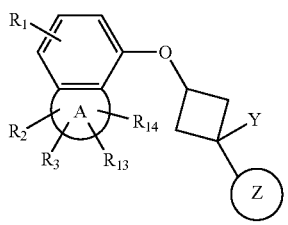
(I-IIac)

or a pharmaceutically acceptable salt and/or solvate thereof and/or derivative thereof, wherein $R_1$, $R_2$, $R_3$, $R_{13}$, $R_{14}$, A, Y and Z are as defined above.

In one embodiment, the compound is a compound of formula (Ia-II):

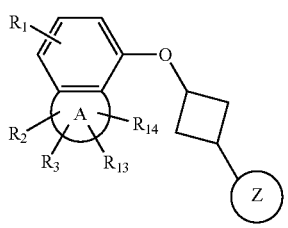
(Ia-II)

or a pharmaceutically acceptable salt and/or solvate thereof and/or derivative thereof, wherein $R_1$, $R_2$, $R_3$, $R_{13}$, $R_{14}$, A and Z are as defined above. In one embodiment, the compound is a compound of formula (Ib-II):

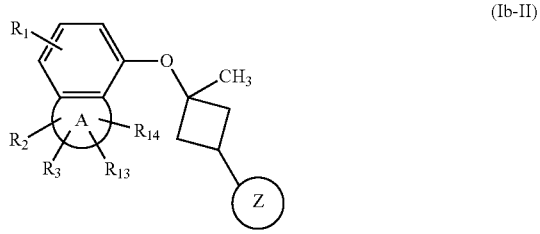
(Ib-II)

or a pharmaceutically acceptable salt and/or solvate thereof and/or derivative thereof, wherein $R_1$, $R_2$, $R_3$, $R_{13}$, $R_{14}$, A and Z are as defined above.

In one embodiment, the compound is a compound of formula (Ic-II):

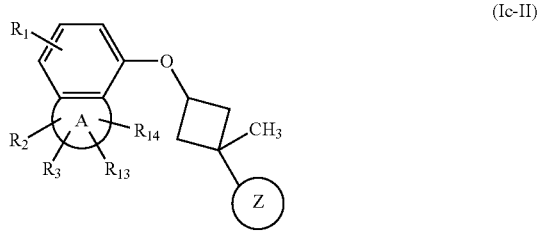
(Ic-II)

or a pharmaceutically acceptable salt and/or solvate thereof and/or derivative thereof, wherein $R_1$, $R_2$, $R_3$, $R_{13}$, $R_{14}$, A and Z are as defined above.

In one embodiment, the compound is a compound of formula (I-III):

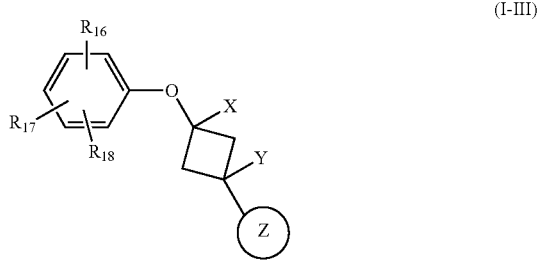
(I-III)

or a pharmaceutically acceptable salt and/or solvate thereof and/or derivative thereof, wherein $R_{16}$, $R_{17}$, $R_{18}$, X, Y and Z are as defined above.

In one embodiment, the compound is a compound of formula (I-IIIab):

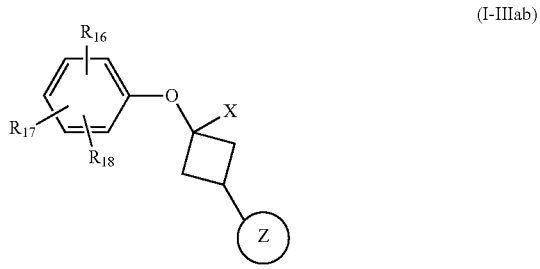
(I-IIIab)

or a pharmaceutically acceptable salt and/or solvate thereof and/or derivative thereof, wherein $R_{16}$, $R_{17}$, $R_{18}$, X and Z are as defined above.

In one embodiment, the compound is a compound of formula (I-IIIac):

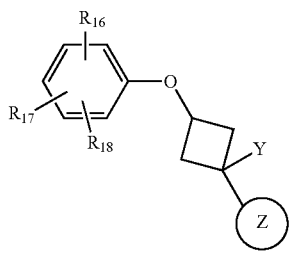

(I-IIIac)

or a pharmaceutically acceptable salt and/or solvate thereof and/or derivative thereof, wherein $R_{16}$, $R_{17}$, $R_{18}$, Y and Z are as defined above.

In one embodiment, the compound is a compound of formula (Ia-III):

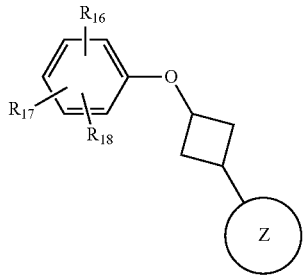

(Ia-III)

or a pharmaceutically acceptable salt and/or solvate thereof and/or derivative thereof, wherein $R_{16}$, $R_{17}$, $R_{18}$ and Z are as defined above.

In one embodiment, the compound is a compound of formula (Ib-III):

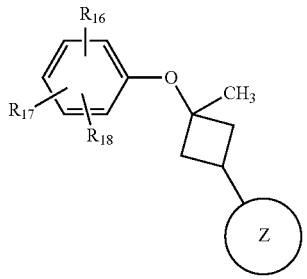

(Ib-III)

or a pharmaceutically acceptable salt and/or solvate thereof and/or derivative thereof, wherein $R_{16}$, $R_{17}$, $R_{18}$ and Z are as defined above.

In one embodiment, the compound is a compound of formula (Ic-III):

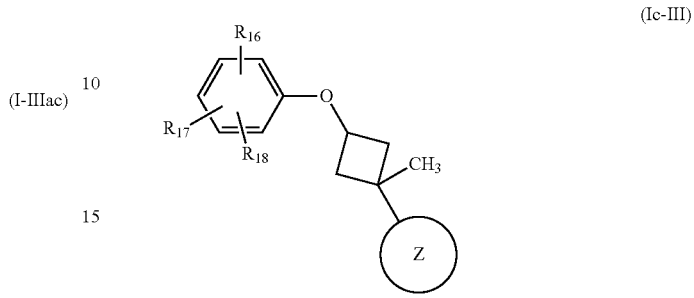

(Ic-III)

or a pharmaceutically acceptable salt and/or solvate thereof and/or derivative thereof, wherein $R_{16}$, $R_{17}$, $R_{18}$ and Z are as defined above.

In one embodiment, the compound is a compound of formula (I-IV):

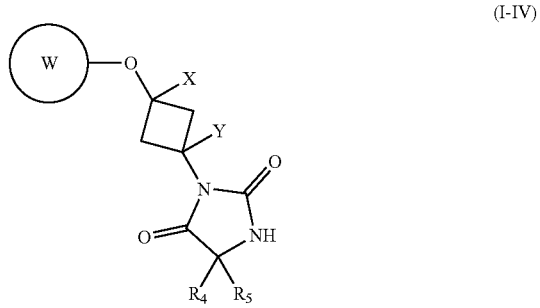

(I-IV)

or a pharmaceutically acceptable salt and/or solvate thereof and/or derivative thereof, wherein $R_4$, $R_5$, X, Y and W are as defined above.

In one embodiment, the compound is a compound of formula (I-IVab):

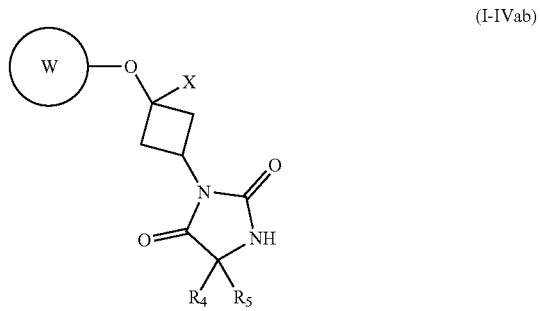

(I-IVab)

or a pharmaceutically acceptable salt and/or solvate thereof and/or derivative thereof, wherein $R_4$, $R_5$, X and W are as defined above.

In one embodiment, the compound is a compound of formula (I-IVac):

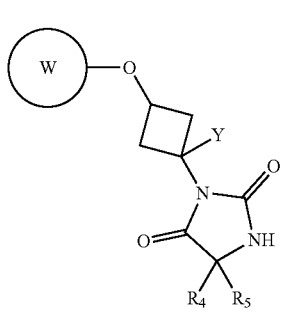

(I-IVac)

or a pharmaceutically acceptable salt and/or solvate thereof and/or derivative thereof, wherein $R_4$, $R_5$, Y and W are as defined above.

In one embodiment, the compound is a compound of formula (Ia-IV):

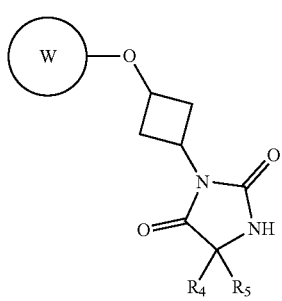

(Ia-IV)

or a pharmaceutically acceptable salt and/or solvate thereof and/or derivative thereof, wherein $R_4$, $R_5$ and W are as defined above.

In one embodiment, the compound is a compound of formula (Ib-IV):

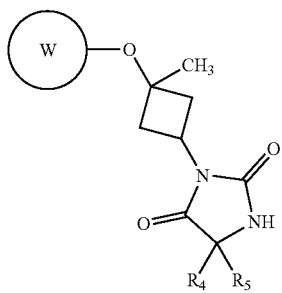

(Ib-IV)

or a pharmaceutically acceptable salt and/or solvate thereof and/or derivative thereof, wherein $R_4$, $R_5$ and W are as defined above.

In one embodiment, the compound is a compound of formula (Ic-IV):

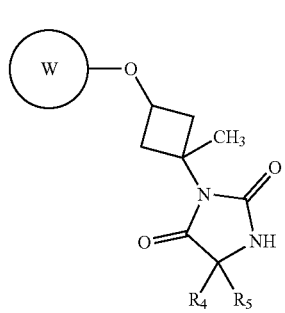

(Ic-IV)

or a pharmaceutically acceptable salt and/or solvate thereof and/or derivative thereof, wherein $R_4$, $R_5$ and W are as defined above.

In one embodiment, the compound is a compound of formula (I-V):

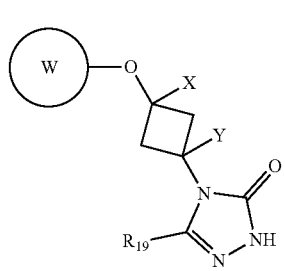

(I-V)

or a pharmaceutically acceptable salt and/or solvate thereof and/or derivative thereof, wherein $R_{19}$, X, Y and W are as defined above.

In one embodiment, the compound is a compound of formula (I-Vab):

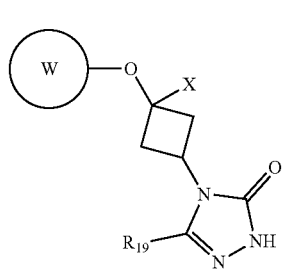

(I-Vab)

or a pharmaceutically acceptable salt and/or solvate thereof and/or derivative thereof, wherein $R_{19}$, X and W are as defined above.

In one embodiment, the compound is a compound of formula (I-Vac):

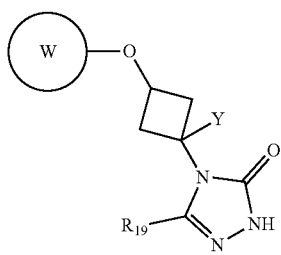

(I-Vac)

or a pharmaceutically acceptable salt and/or solvate thereof and/or derivative thereof, wherein $R_{19}$, Y and W are as defined above.

In one embodiment, the compound is a compound of formula (Ia-V):

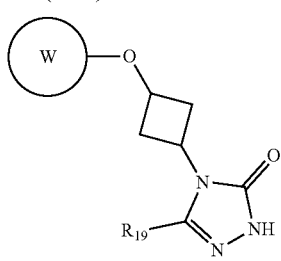

(Ia-V)

or a pharmaceutically acceptable salt and/or solvate thereof and/or derivative thereof, wherein $R_{19}$ and W are as defined above.

In one embodiment, the compound is a compound of formula (Ib-V):

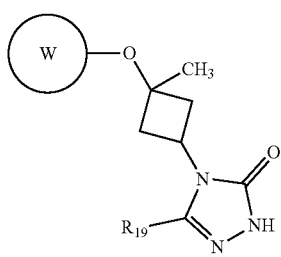

(Ib-V)

or a pharmaceutically acceptable salt and/or solvate thereof and/or derivative thereof, wherein $R_{19}$ and W are as defined above.

In one embodiment, the compound is a compound of formula (Ic-V):

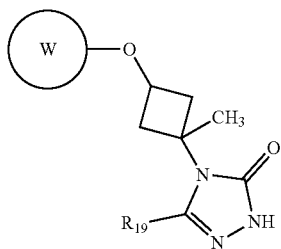

(Ic-V)

or a pharmaceutically acceptable salt and/or solvate thereof and/or derivative thereof, wherein $R_{19}$ and W are as defined above.

In one embodiment, the compound is a compound of formula I):

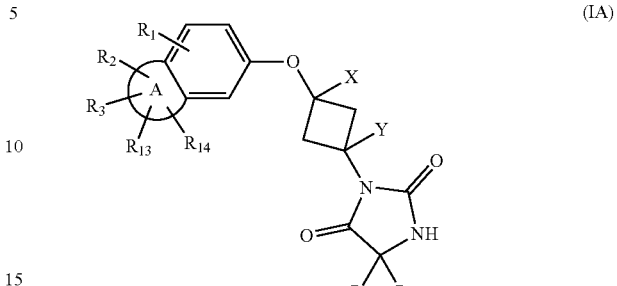

(IA)

or a pharmaceutically acceptable salt and/or solvate thereof and/or derivative thereof, wherein $R_1$, $R_2$, $R_3$, $R_{13}$, $R_{14}$, A, X, Y, $R_4$ and $R_5$ are as defined above.

In one embodiment, the compound is a compound of formula (IaA):

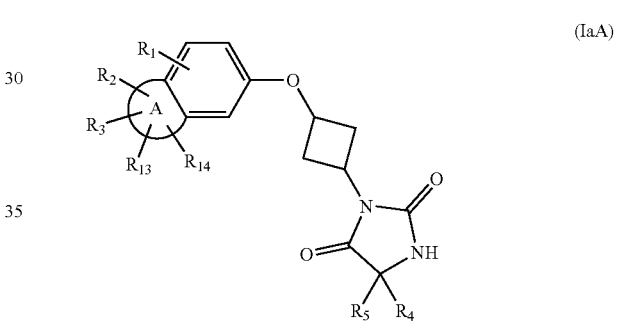

(IaA)

or a pharmaceutically acceptable salt and/or solvate thereof and/or derivative thereof, wherein $R_1$, $R_2$, $R_3$, $R_{13}$, $R_{14}$, A, $R_4$ and $R_5$ are as defined above.

In one embodiment, the compound is a compound of formula (IbA):

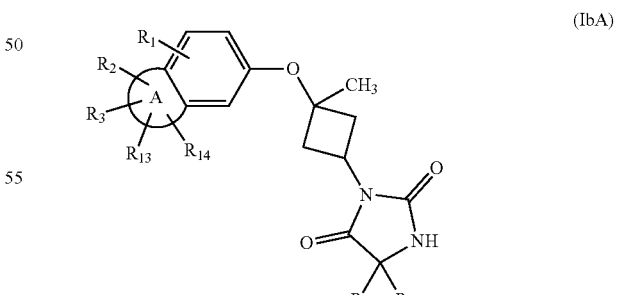

(IbA)

or a pharmaceutically acceptable salt and/or solvate thereof and/or derivative thereof, wherein $R_1$, $R_2$, $R_3$, $R_{13}$, $R_{14}$, A, $R_4$ and $R_5$ are as defined above.

In one embodiment, the compound is a compound of formula (IcA):

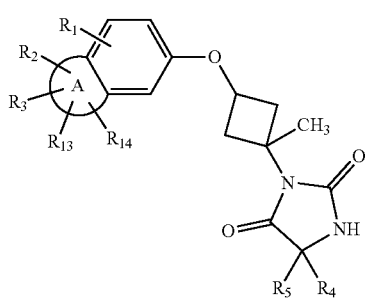

(IcA)

or a pharmaceutically acceptable salt and/or solvate thereof and/or derivative thereof, wherein $R_1$, $R_2$, $R_3$, $R_{13}$, $R_{14}$, A, $R_4$ and $R_5$ are as defined above.

In one embodiment, the compound of formula (IA) has syn configuration:

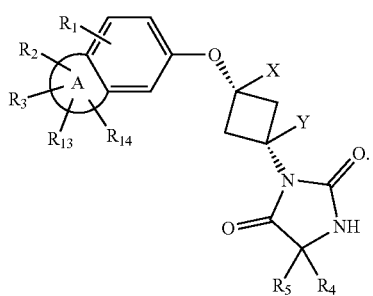

syn-(IA)

In one embodiment, the compound of formula (IA) has anti configuration:

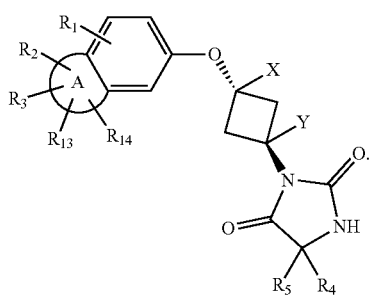

anti-(IA)

Suitably the compound of formula (IA) has anti configuration.

In one embodiment, the compound is a compound of formula (IB):

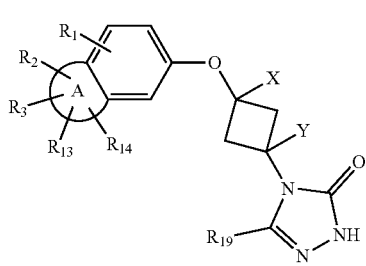

(IB)

or a pharmaceutically acceptable salt and/or solvate thereof and/or derivative thereof wherein $R_1$, $R_2$, $R_3$, $R_{13}$, $R_{14}$, A, X, Y and $R_{19}$ are as defined above.

In one embodiment, the compound is a compound of formula (IaB):

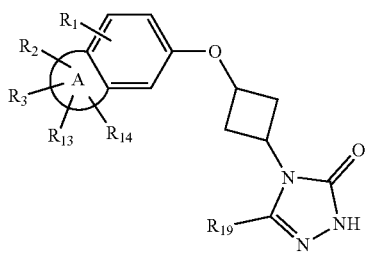

(IaB)

or a pharmaceutically acceptable salt and/or solvate thereof and/or derivative thereof wherein $R_1$, $R_2$, $R_3$, $R_{13}$, $R_{14}$, A and $R_{19}$ are as defined above.

In one embodiment, the compound is a compound of formula (IbB):

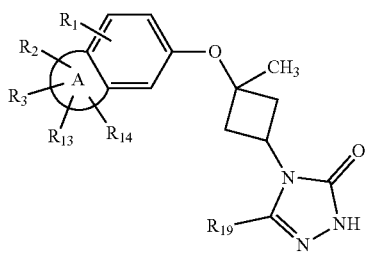

(IbB)

or a pharmaceutically acceptable salt and/or solvate thereof and/or derivative thereof wherein $R_1$, $R_2$, $R_3$, $R_{13}$, $R_{14}$, A and $R_{19}$ are as defined above.

In one embodiment, the compound is a compound of formula (IcB):

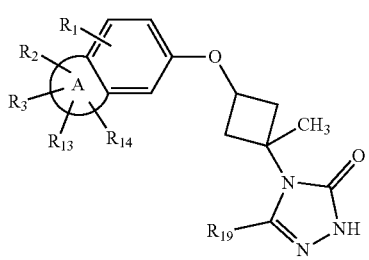

(IcB)

or a pharmaceutically acceptable salt and/or solvate thereof and/or derivative thereof wherein $R_1$, $R_2$, $R_3$, $R_{13}$, $R_{14}$, A and $R_{19}$ are as defined above.

In one embodiment, the compound of formula (IB) has syn configuration:

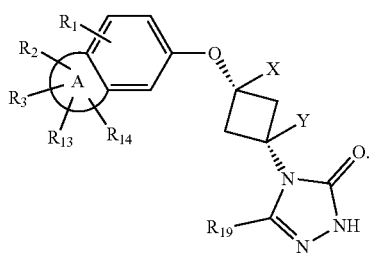

syn-(IB)

In one embodiment, the compound of formula (IB) has anti configuration:

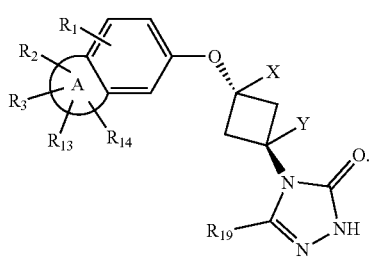

anti-(IB)

Suitably the compound of formula (IB) has anti configuration.

In one embodiment, the compound is a compound of formula (IC):

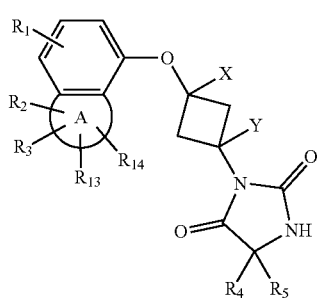

(IC)

or a pharmaceutically acceptable salt and/or solvate thereof and/or derivative thereof wherein $R_1$, $R_2$, $R_3$, $R_{13}$, $R_{14}$, A, X, Y, $R_4$ and $R_5$ are as defined above.

In one embodiment, the compound is a compound of formula (IaC):

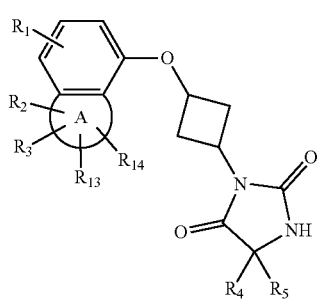

(IaC)

or a pharmaceutically acceptable salt and/or solvate thereof and/or derivative thereof wherein $R_1$, $R_2$, $R_3$, $R_{13}$, $R_{14}$, A, $R_4$ and $R_5$ are as defined above.

In one embodiment, the compound is a compound of formula (IbC):

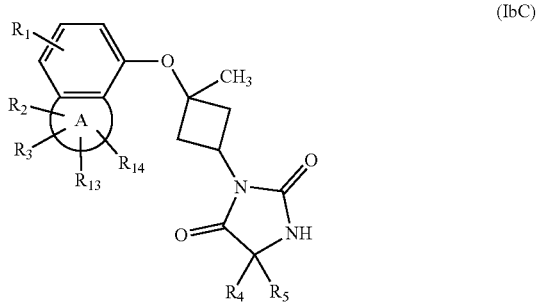

(IbC)

or a pharmaceutically acceptable salt and/or solvate thereof and/or derivative thereof wherein $R_1$, $R_2$, $R_3$, $R_{13}$, $R_{14}$, A, $R_4$ and $R_5$ are as defined above.

In one embodiment, the compound is a compound of formula (IcC):

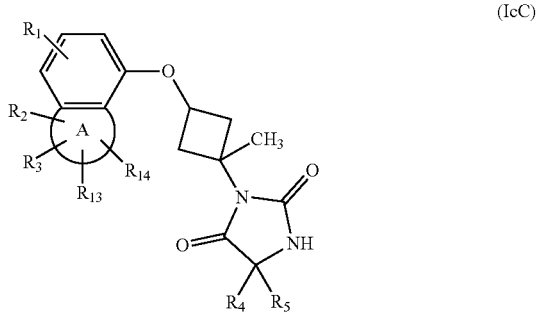

(IcC)

or a pharmaceutically acceptable salt and/or solvate thereof and/or derivative thereof wherein $R_1$, $R_2$, $R_3$, $R_{13}$, $R_{14}$, A, $R_4$ and $R_5$ are as defined above.

In one embodiment, the compound of formula (IC) has syn configuration:

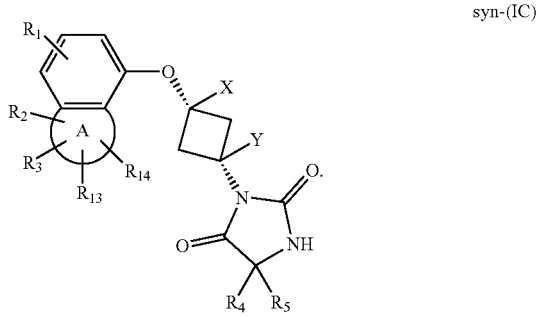

syn-(IC)

In one embodiment, the compound of formula (IC) has anti configuration:

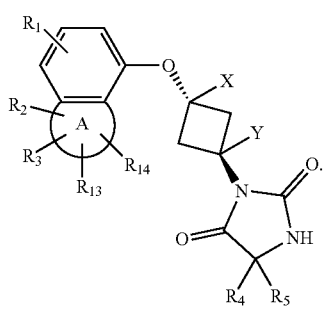

anti-(IC)

Suitably the compound of formula (IC) has anti configuration.

In one embodiment, the compound is a compound of formula (ID):

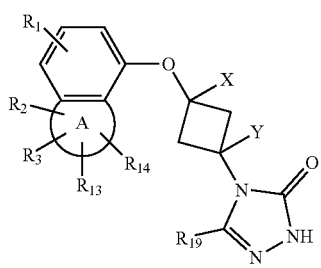

(ID)

or a pharmaceutically acceptable salt and/or solvate thereof and/or derivative thereof wherein $R_1$, $R_2$, $R_3$, $R_{13}$, $R_{14}$, A, X, Y and $R_{19}$ are as defined above.

In one embodiment, the compound is a compound of formula (IaD):

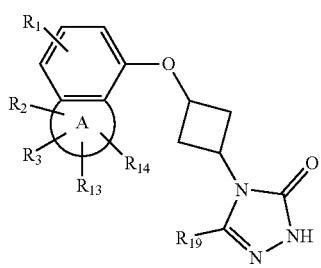

(IaD)

or a pharmaceutically acceptable salt and/or solvate thereof and/or derivative thereof wherein $R_1$, $R_2$, $R_3$, $R_{13}$, $R_{14}$, A and $R_{19}$ are as defined above.

In one embodiment, the compound is a compound of formula (IbD):

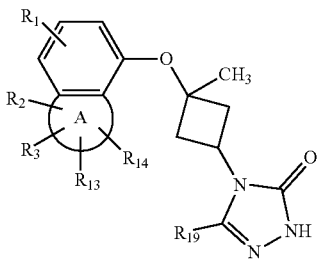

(IbD)

or a pharmaceutically acceptable salt and/or solvate thereof and/or derivative thereof wherein $R_1$, $R_2$, $R_3$, $R_{13}$, $R_{14}$, A and $R_{19}$ are as defined above.

In one embodiment, the compound is a compound of formula (IcD):

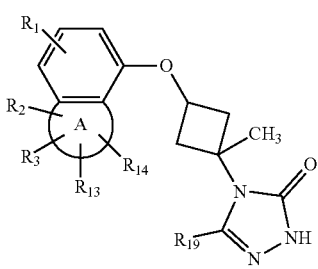

(IcD)

or a pharmaceutically acceptable salt and/or solvate thereof and/or derivative thereof wherein $R_1$, $R_2$, $R_3$, $R_{13}$, $R_{14}$, A and $R_{19}$ are as defined above.

In one embodiment, the compound of formula (ID) has syn configuration:

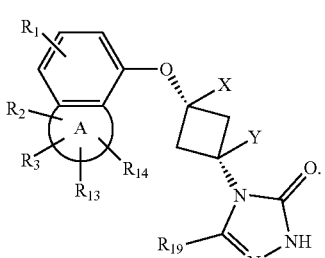

syn-(ID)

In one embodiment, the compound of formula (ID) has anti configuration:

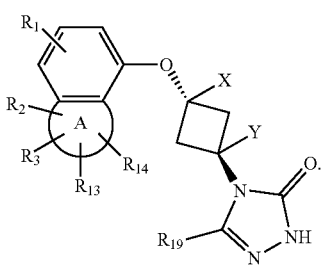

anti-(ID)

Suitably the compound of formula (ID) has anti configuration.

In one embodiment, the compound is a compound of formula (IE):

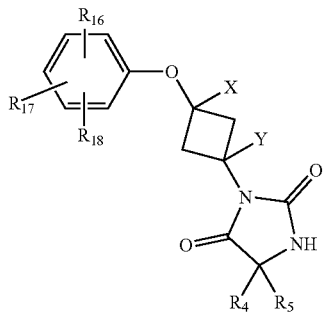

(IE)

wherein $R_{16}$, $R_{17}$, $R_{18}$, X, Y, $R_4$ and $R_5$ are as defined above.

In one embodiment, the compound is a compound of formula (IaE):

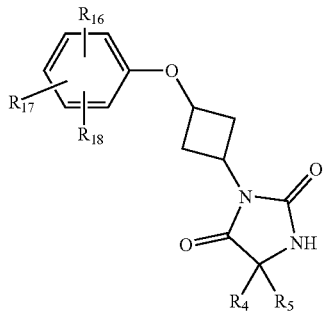

(IaE)

wherein $R_{16}$, $R_{17}$, $R_{18}$, $R_4$ and $R_5$ are as defined above.

In one embodiment, the compound is a compound of formula (IbE):

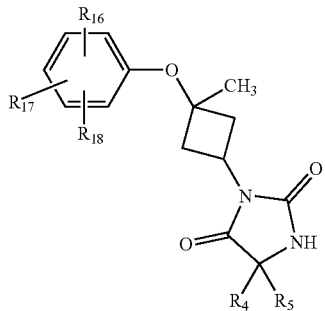

(IbE)

wherein $R_{16}$, $R_{17}$, $R_{18}$, $R_4$ and $R_5$ are as defined above.

In one embodiment, the compound is a compound of formula (IcE):

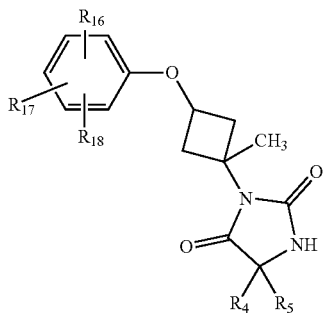

(IcE)

wherein $R_{16}$, $R_{17}$, $R_{18}$, $R_4$ and $R_5$ are as defined above.

In one embodiment, the compound of formula (IE) has syn configuration:

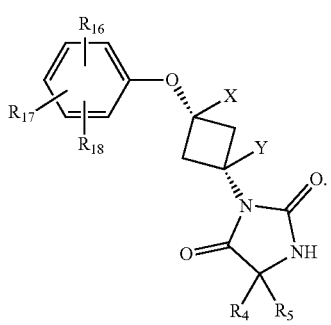

syn-(IE)

In one embodiment, the compound of formula (IE) has anti configuration:

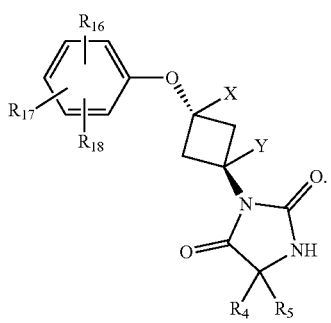

anti-(IE)

Suitably the compound of formula (IE) has anti configuration.

In one embodiment, the compound is a compound of formula (IF):

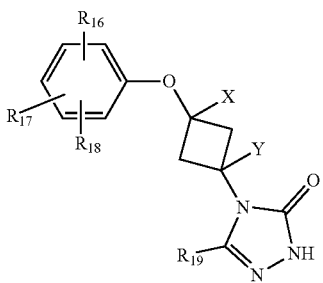

(IF)

wherein $R_{16}$, $R_{17}$, $R_{18}$, X, Y and $R_{19}$ are as defined above.

In one embodiment, the compound is a compound of formula (IaF):

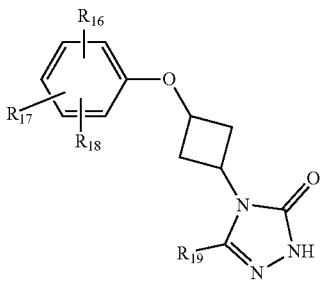

(IaF)

wherein $R_{16}$, $R_{17}$, $R_{18}$ and $R_{19}$ are as defined above.

In one embodiment, the compound is a compound of formula (IbF):

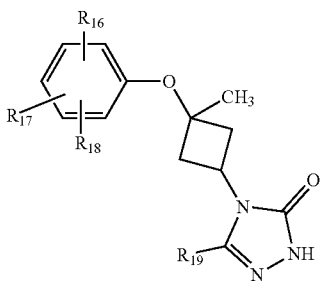

(IbF)

wherein $R_{16}$, $R_{17}$, $R_{18}$ and $R_{19}$ are as defined above.

In one embodiment, the compound is a compound of formula (IcF):

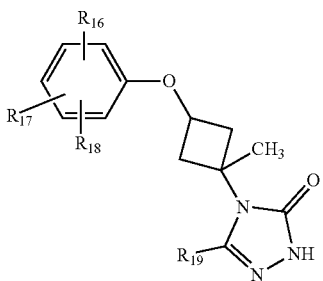

(IcF)

wherein $R_{16}$, $R_{17}$, $R_{18}$ and $R_{19}$ are as defined above.

In one embodiment, the compound of formula (IE) has syn configuration:

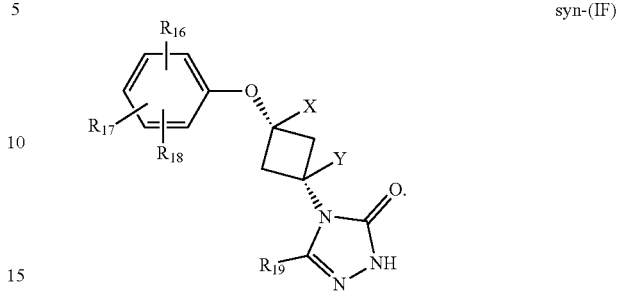

syn-(IF)

In one embodiment, the compound of formula (IF) has anti configuration:

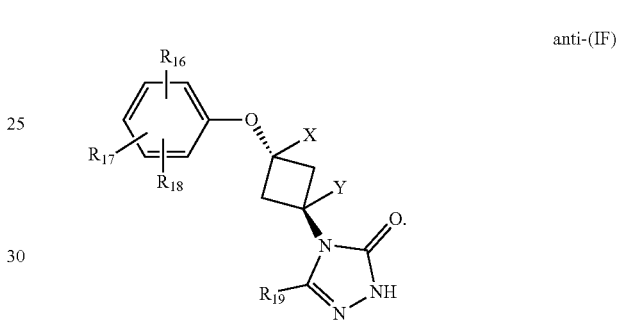

anti-(IF)

Suitably the compound of formula (IF) has anti configuration.

In one embodiment, the compound of formula (I) is selected from the group consisting of:
syn-5,5-dimethyl-3-[3-[4-methyl-3-(trifluoromethoxy)phenoxy]cyclobutyl]imidazolidine-2,4-dione (Example 1);
syn-5,5-dimethyl-3-[3-(7-methylspiro[2H-benzofuran-3,1'-cyclopropane]-4-yl)oxycyclobutyl]imidazolidine-2,4-dione (Example 2);
syn-4-[3-(4,4-dimethyl-2,5-dioxo-imidazolidin-1-yl)cyclobutoxy]-2-isopropyl-benzonitrile (Example 3);
anti-5,5-dimethyl-3-[3-[4-methyl-3-(trifluoromethoxy)phenoxy]cyclobutyl]imidazolidine-2,4-dione (Example 4);
anti-5,5-dimethyl-3-[3-(7-methylspiro[2H-benzofuran-3,1'-cyclopropane]-4-yl)oxycyclobutyl]imidazolidine-2,4-dione (Example 5);
anti-4-[3-(4,4-dimethyl-2,5-dioxo-imidazolidin-1-yl)cyclobutoxy]-2-isopropyl-benzonitrile (Example 6);
syn-5,5-dimethyl-3-[3-[3-(trifluoromethoxy)phenoxy]cyclobutyl]imidazolidine-2,4-dione (Example 7);
anti-5,5-dimethyl-3-[3-[3-(trifluoromethoxy)phenoxy]cyclobutyl]imidazolidine-2,4-dione (Example 8);
syn-3-[3-(2-tert-butylphenoxy)cyclobutyl]-5,5-dimethyl-imidazolidine-2,4-dione (Example 9);
anti-3-[3-(2-tert-butylphenoxy)cyclobutyl]-5,5-dimethyl-imidazolidine-2,4-dione (Example 10);
syn-3-tert-butyl-4-[3-(4,4-dimethyl-2,5-dioxo-imidazolidin-1-yl)cyclobutoxy]benzonitrile (Example 11);
anti-3-tert-butyl-4-[3-(4,4-dimethyl-2,5-dioxo-imidazolidin-1-yl)cyclobutoxy]benzonitrile (Example 12);
syn-4-[3-(4,4-dimethyl-2,5-dioxo-imidazolidin-1-yl)cyclobutoxy]-2-(trifluoromethoxy)benzonitrile (Example 13);

anti-4-[3-(4,4-dimethyl-2,5-dioxo-imidazolidin-1-yl)cyclobutoxy]-2-(trifluoromethoxy)benzonitrile (Example 14);
anti-5,5-dimethyl-3-(3-spiro[2H-benzofuran-3,1'-cyclopropane]-4-yloxycyclobutyl)imidazolidine-2,4-dione (Example 15);
syn-5,5-dimethyl-3-(3-spiro[2H-benzofuran-3,1'-cyclopropane]-4-yloxycyclobutyl)imidazolidine-2,4-dione (Example 16);
syn-(5R)-5-ethyl-3-[3-(7-methylspiro[2H-benzofuran-3,1'-cyclopropane]-4-yl)oxycyclobutyl]imidazolidine-2,4-dione (Example 17);
anti-(5R)-5-ethyl-3-[3-[4-methyl-3-(trifluoromethoxy)phenoxy]cyclobutyl]imidazolidine-2,4-dione (Example 18);
anti-(5R)-5-ethyl-3-[3-(7-methylspiro[2H-benzofuran-3,1'-cyclopropane]-4-yl)oxycyclobutyl]imidazolidine-2,4-dione (Example 19);
syn-(5S)-5-ethyl-3-[3-(7-methylspiro[2H-benzofuran-3,1'-cyclopropane]-4-yl)oxycyclobutyl]imidazolidine-2,4-dione (Example 20);
anti-(5S)-5-ethyl-3-[3-[4-methyl-3-(trifluoromethoxy)phenoxy]cyclobutyl]imidazolidine-2,4-dione (Example 21);
anti-(5S)-5-ethyl-3-[3-(7-methylspiro[2H-benzofuran-3,1'-cyclopropane]-4-yl)oxycyclobutyl]imidazolidine-2,4-dione (Example 22);
syn-3-methyl-4-[3-(7-methylspiro[2H-benzofuran-3,1'-cyclopropane]-4-yl)oxycyclobutyl]-1H-1,2,4-triazol-5-one (Example 23); and
anti-3-methyl-4-[3-(7-methylspiro[2H-benzofuran-3,1'-cyclopropane]-4-yl)oxycyclobutyl]-1H-1,2,4-triazol-5-one (Example 24);
or a pharmaceutically acceptable salt and/or solvate thereof and/or derivative thereof.

In a further embodiment, the compound of formula (I) is selected from the group consisting of:
4-[3-(4,4-dimethyl-2,5-dioxo-imidazolidin-1-yl)cyclobutoxy]spiro[2H-benzofuran-3,1'-cyclopropane]-7-carbonitrile (Example 25);
6-[3-(7-methylspiro[2H-benzofuran-3,1'-cyclopropane]-4-yl)oxycyclobutyl]-2-oxa-6,8-diazaspiro[3.4]octane-5,7-dione (Example 26);
3-[3-(7-methylspiro[2H-benzofuran-3,1'-cyclopropane]-4-yl)oxycyclobutyl]imidazolidine-2,4-dione (Example 27);
(5S)-5-methyl-3-[3-(7-methylspiro[2H-benzofuran-3,1'-cyclopropane]-4-yl)oxycyclobutyl]imidazolidine-2,4-dione (Example 28); and
(5R)-5-methyl-3-[3-(7-methylspiro[2H-benzofuran-3,1'-cyclopropane]-4-yl)oxycyclobutyl]imidazolidine-2,4-dione (Example 29);
or a pharmaceutically acceptable salt and/or solvate thereof and/or derivative thereof.

Other compounds of the invention include:
4-[3-[(5R)-6,8-dioxo-3-oxa-7,9-diazaspiro[4.4]nonan-7-yl]cyclobutoxy]spiro[2H-benzofuran-3,1'-cyclopropane]-7-carbonitrile;
4-[3-[(5S)-6,8-dioxo-3-oxa-7,9-diazaspiro[4.4]nonan-7-yl]cyclobutoxy]spiro[2H-benzofuran-3,1'-cyclopropane]-7-carbonitrile;
4-[3-(2,5-dioxoimidazolidin-1-yl)cyclobutoxy]spiro[2H-benzofuran-3,1'-cyclopropane]-7-carbonitrile;
4-[3-(5,7-dioxo-2-oxa-6,8-diazaspiro[3.4]octan-6-yl)cyclobutoxy]spiro[2H-benzofuran-3,1'-cyclopropane]-7-carbonitrile;
4-[3-[(4R)-4-methyl-2,5-dioxo-imidazolidin-1-yl]cyclobutoxy]spiro[2H-benzofuran-3,1'-cyclopropane]-7-carbonitrile;
4-[3-[(4S)-4-methyl-2,5-dioxo-imidazolidin-1-yl]cyclobutoxy]spiro[2H-benzofuran-3,1'-cyclopropane]-7-carbonitrile;
4-[3-[(4R)-4-ethyl-2,5-dioxo-imidazolidin-1-yl]cyclobutoxy]spiro[2H-benzofuran-3,1'-cyclopropane]-7-carbonitrile;
4-[3-[(4S)-4-ethyl-2,5-dioxo-imidazolidin-1-yl]cyclobutoxy]spiro[2H-benzofuran-3,1'-cyclopropane]-7-carbonitrile;
4-[3-[(4R)-4-ethyl-4-methyl-2,5-dioxo-imidazolidin-1-yl]cyclobutoxy]spiro[2H-benzofuran-3,1'-cyclopropane]-7-carbonitrile;
4-[3-[(4S)-4-ethyl-4-methyl-2,5-dioxo-imidazolidin-1-yl]cyclobutoxy]spiro[2H-benzofuran-3,1'-cyclopropane]-7-carbonitrile;
4-[3-(4,4-dimethyl-2,5-dioxo-imidazolidin-1-yl)cyclobutoxy]-3,3-dimethyl-2H-benzofuran-7-carbonitrile;
4-[3-[(5R)-6,8-dioxo-3-oxa-7,9-diazaspiro[4.4]nonan-7-yl]cyclobutoxy]-3,3-di methyl-2H-benzofuran-7-carbonitrile;
4-[3-[(5S)-6,8-dioxo-3-oxa-7,9-diazaspiro[4.4]nonan-7-yl]cyclobutoxy]-3,3-di methyl-2H-benzofuran-7-carbonitrile;
4-[3-(2,5-dioxoimidazolidin-1-yl)cyclobutoxy]-3,3-dimethyl-2H-benzofuran-7-carbonitrile;
4-[3-(5,7-dioxo-2-oxa-6,8-diazaspiro[3.4]octan-6-yl)cyclobutoxy]-3,3-di methyl-2H-benzofuran-7-carbonitrile;
3,3-dimethyl-4-[3-[(4R)-4-methyl-2,5-dioxo-imidazolidin-1-yl]cyclobutoxy]-2H-benzofuran-7-carbonitrile;
3,3-dimethyl-4-[3-[(4S)-4-methyl-2,5-dioxo-imidazolidin-1-yl]cyclobutoxy]-2H-benzofuran-7-carbonitrile;
4-[3-[(4R)-4-ethyl-2,5-dioxo-imidazolidin-1-yl]cyclobutoxy]-3,3-dimethyl-2H-benzofuran-7-carbonitrile;
4-[3-[(4S)-4-ethyl-2,5-dioxo-imidazolidin-1-yl]cyclobutoxy]-3,3-dimethyl-2H-benzofuran-7-carbonitrile;
4-[3-[(4R)-4-ethyl-4-methyl-2,5-dioxo-imidazolidin-1-yl]cyclobutoxy]-3,3-dimethyl-2H-benzofuran-7-carbonitrile;
4-[3-[(4S)-4-ethyl-4-methyl-2,5-dioxo-imidazolidin-1-yl]cyclobutoxy]-3,3-dimethyl-2H-benzofuran-7-carbonitrile;
4-[3-(4,4-dimethyl-2,5-dioxo-imidazolidin-1-yl)cyclobutoxy]spiro[2H-benzofuran-3,1'-cyclopropane]-6-carbonitrile;
4-[3-[(5R)-6,8-dioxo-3-oxa-7,9-diazaspiro[4.4]nonan-7-yl]cyclobutoxy]spiro[2H-benzofuran-3,1'-cyclopropane]-6-carbonitrile;
4-[3-[(5S)-6,8-dioxo-3-oxa-7,9-diazaspiro[4.4]nonan-7-yl]cyclobutoxy]spiro[2H-benzofuran-3,1'-cyclopropane]-6-carbonitrile;
4-[3-(2,5-dioxoimidazolidin-1-yl)cyclobutoxy]spiro[2H-benzofuran-3,1'-cyclopropane]-6-carbonitrile;
4-[3-(5,7-dioxo-2-oxa-6,8-diazaspiro[3.4]octan-6-yl)cyclobutoxy]spiro[2H-benzofuran-3,1'-cyclopropane]-6-carbonitrile;
4-[3-[(4S)-4-methyl-2,5-dioxo-imidazolidin-1-yl]cyclobutoxy]spiro[2H-benzofuran-3,1'-cyclopropane]-6-carbonitrile;
4-[3-[(4R)-4-methyl-2,5-dioxo-imidazolidin-1-yl]cyclobutoxy]spiro[2H-benzofuran-3,1'-cyclopropane]-6-carbonitrile;
4-[3-[(4S)-4-ethyl-2,5-dioxo-imidazolidin-1-yl]cyclobutoxy]spiro[2H-benzofuran-3,1'-cyclopropane]-6-carbonitrile;
4-[3-[(4R)-4-ethyl-2,5-dioxo-imidazolidin-1-yl]cyclobutoxy]spiro[2H-benzofuran-3,1'-cyclopropane]-6-carbonitrile;

4-[3-[(4S)-4-ethyl-4-methyl-2,5-dioxo-imidazolidin-1-yl] cyclobutoxy]spiro[2H-benzofuran-3,1'-cyclopropane]-6-carbonitrile;
4-[3-[(4R)-4-ethyl-4-methyl-2,5-dioxo-imidazolidin-1-yl] cyclobutoxy]spiro[2H-benzofuran-3,1'-cyclopropane]-6-carbonitrile;
4-[3-[(5R)-6,8-dioxo-3-oxa-7,9-diazaspiro[4.4]nonan-7-yl] cyclobutoxy]spiro[2H-benzofuran-3,1'-cyclopropane]-5-carbonitrile;
4-[3-[(5S)-6,8-dioxo-3-oxa-7,9-diazaspiro[4.4]nonan-7-yl] cyclobutoxy]spiro[2H-benzofuran-3,1'-cyclopropane]-5-carbonitrile;
4-[3-(2,5-dioxoimidazolidin-1-yl)cyclobutoxy]spiro[2H-benzofuran-3,1'-cyclopropane]-5-carbonitrile;
4-[3-(5,7-dioxo-2-oxa-6,8-diazaspiro[3.4]octan-6-yl)cyclobutoxy]spiro[2H-benzofuran-3,1'-cyclopropane]-5-carbonitrile;
4-[3-[(4S)-4-methyl-2,5-dioxo-imidazolidin-1-yl]cyclobutoxy]spiro[2H-benzofuran-3,1'-cyclopropane]-5-carbonitrile;
4-[3-[(4R)-4-methyl-2,5-dioxo-imidazolidin-1-yl]cyclobutoxy]spiro[2H-benzofuran-3,1'-cyclopropane]-5-carbonitrile;
4-[3-(4,4-dimethyl-2,5-dioxo-imidazolidin-1-yl)cyclobutoxy]spiro[2H-benzofuran-3,1'-cyclopropane]-5-carbonitrile;
4-[3-[(4R)-4-ethyl-2,5-dioxo-imidazolidin-1-yl]cyclobutoxy]spiro[2H-benzofuran-3,1'-cyclopropane]-5-carbonitrile;
4-[3-[(4S)-4-ethyl-2,5-dioxo-imidazolidin-1-yl]cyclobutoxy]spiro[2H-benzofuran-3,1'-cyclopropane]-5-carbonitrile;
4-[3-[(4R)-4-ethyl-4-methyl-2,5-dioxo-imidazolidin-1-yl] cyclobutoxy]spiro[2H-benzofuran-3,1'-cyclopropane]-5-carbonitrile;
4-[3-[(4S)-4-ethyl-4-methyl-2,5-dioxo-imidazolidin-1-yl] cyclobutoxy]spiro[2H-benzofuran-3,1'-cyclopropane]-5-carbonitrile;
(5R)-7-[3-[(3,3,7-trimethyl-2H-benzofuran-4-yl)oxy]cyclobutyl]-3-oxa-7,9-diazaspiro[4.4]nonane-6,8-dione;
(5S)-7-[3-[(3,3,7-trimethyl-2H-benzofuran-4-yl)oxy]cyclobutyl]-3-oxa-7,9-diazaspiro[4.4]nonane-6,8-dione;
3-[3-[(3,3,7-trimethyl-2H-benzofuran-4-yl)oxy]cyclobutyl] imidazolidine-2,4-dione;
6-[3-[(3,3,7-trimethyl-2H-benzofuran-4-yl)oxy]cyclobutyl]-2-oxa-6,8-diazaspiro[3.4]octane-5,7-dione;
(5R)-7-[3-(7-methylspiro[2H-benzofuran-3,1'-cyclopropane]-4-yl)oxycyclobutyl]-3-oxa-7,9-diazaspiro[4.4] nonane-6,8-dione;
(5S)-7-[3-(7-methylspiro[2H-benzofuran-3,1'-cyclopropane]-4-yl)oxycyclobutyl]-3-oxa-7,9-diazaspiro[4.4] nonane-6,8-dione;
(5R)-7-(3-spiro[2H-benzofuran-3,1'-cyclopropane]-4-yloxycyclobutyl)-3-oxa-7,9-diazaspiro[4.4]nonane-6,8-dione;
(5S)-7-(3-spiro[2H-benzofuran-3,1'-cyclopropane]-4-yloxycyclobutyl)-3-oxa-7,9-diazaspiro[4.4]nonane-6,8-dione;
3-(3-spiro[2H-benzofuran-3,1'-cyclopropane]-4-yloxycyclobutyl)imidazolidine-2,4-dione;
6-(3-spiro[2H-benzofuran-3,1'-cyclopropane]-4-yloxycyclobutyl)-2-oxa-6,8-diazaspiro[3.4]octane-5,7-dione;
(5R)-5-methyl-3-(3-spiro[2H-benzofuran-3,1'-cyclopropane]-4-yloxycyclobutyl)imidazolidine-2,4-dione;
(5S)-5-methyl-3-(3-spiro[2H-benzofuran-3,1'-cyclopropane]-4-yloxycyclobutyl)imidazolidine-2,4-dione;
(5R)-5-ethyl-3-(3-spiro[2H-benzofuran-3,1'-cyclopropane]-4-yloxycyclobutyl)imidazolidine-2,4-dione;
(5S)-5-ethyl-3-(3-spiro[2H-benzofuran-3,1'-cyclopropane]-4-yloxycyclobutyl)imidazolidine-2,4-dione;
(5R)-5-ethyl-5-methyl-3-(3-spiro[2H-benzofuran-3,1'-cyclopropane]-4-yloxycyclobutyl)imidazolidine-2,4-dione;
(5S)-5-ethyl-5-methyl-3-(3-spiro[2H-benzofuran-3,1'-cyclopropane]-4-yloxycyclobutyl)imidazolidine-2,4-dione;
(5R)-7-[3-[(3,3-dimethyl-2H-benzofuran-4-yl)oxy]cyclobutyl]-3-oxa-7,9-diazaspiro[4.4]nonane-6,8-dione;
(5S)-7-[3-[(3,3-di methyl-2H-benzofuran-4-yl)oxy]cyclobutyl]-3-oxa-7,9-diazaspiro[4.4]nonane-6,8-dione;
3-[3-[(3,3-dimethyl-2H-benzofuran-4-yl)oxy]cyclobutyl] imidazolidine-2,4-dione;
6-[3-[(3,3-dimethyl-2H-benzofuran-4-yl)oxy]cyclobutyl]-2-oxa-6,8-diazaspiro[3.4]octane-5,7-dione;
(5R)-3-[3-[(3,3-dimethyl-2H-benzofuran-4-yl)oxy]cyclobutyl]-5-methyl-imidazolidine-2,4-dione;
(5S)-3-[3-[(3,3-dimethyl-2H-benzofuran-4-yl)oxy]cyclobutyl]-5-methyl-imidazolidine-2,4-dione;
(5R)-3-[3-[(3,3-dimethyl-2H-benzofuran-4-yl)oxy]cyclobutyl]-5-ethyl-imidazolidine-2,4-dione;
(5S)-3-[3-[(3,3-dimethyl-2H-benzofuran-4-yl)oxy]cyclobutyl]-5-ethyl-imidazolidine-2,4-dione;
(5R)-3-[3-[(3,3-dimethyl-2H-benzofuran-4-yl)oxy]cyclobutyl]-5-ethyl-5-methyl-imidazolidine-2,4-dione;
(5S)-3-[3-[(3,3-dimethyl-2H-benzofuran-4-yl)oxy]cyclobutyl]-5-ethyl-5-methyl-imidazolidine-2,4-dione;
(5R)-7-[3-(6-methylspiro[2H-benzofuran-3,1'-cyclopropane]-4-yl)oxycyclobutyl]-3-oxa-7,9-diazaspiro[4.4] nonane-6,8-dione;
(5S)-7-[3-(6-methylspiro[2H-benzofuran-3,1'-cyclopropane]-4-yl)oxycyclobutyl]-3-oxa-7,9-diazaspiro[4.4] nonane-6,8-dione;
3-[3-(6-methylspiro[2H-benzofuran-3,1'-cyclopropane]-4-yl)oxycyclobutyl]imidazolidine-2,4-dione;
6-[3-(6-methylspiro[2H-benzofuran-3,1'-cyclopropane]-4-yl)oxycyclobutyl]-2-oxa-6,8-diazaspiro[3.4]octane-5,7-dione;
(5R)-7-[3-(5-methylspiro[2H-benzofuran-3,1'-cyclopropane]-4-yl)oxycyclobutyl]-3-oxa-7,9-diazaspiro[4.4] nonane-6,8-dione;
(5S)-7-[3-(5-methylspiro[2H-benzofuran-3,1'-cyclopropane]-4-yl)oxycyclobutyl]-3-oxa-7,9-diazaspiro[4.4] nonane-6,8-dione;
3-[3-(5-methylspiro[2H-benzofuran-3,1'-cyclopropane]-4-yl)oxycyclobutyl]imidazolidine-2,4-dione;
6-[3-(5-methylspiro[2H-benzofuran-3,1'-cyclopropane]-4-yl)oxycyclobutyl]-2-oxa-6,8-diazaspiro[3.4]octane-5,7-dione;
(5R)-7-[3-(5-methoxyspiro[2H-benzofuran-3,1'-cyclopropane]-4-yl)oxycyclobutyl]-3-oxa-7,9-diazaspiro[4.4] nonane-6,8-dione;
(5S)-7-[3-(5-methoxyspiro[2H-benzofuran-3,1'-cyclopropane]-4-yl)oxycyclobutyl]-3-oxa-7,9-diazaspiro[4.4] nonane-6,8-dione;
3-[3-(5-methoxyspiro[2H-benzofuran-3,1'-cyclopropane]-4-yl)oxycyclobutyl]imidazolidine-2,4-dione;
6-[3-(5-methoxyspiro[2H-benzofuran-3,1'-cyclopropane]-4-yl)oxycyclobutyl]-2-oxa-6,8-diazaspiro[3.4]octane-5,7-dione;
3-[3-(5-methoxyspiro[2H-benzofuran-3,1'-cyclopropane]-4-yl)oxycyclobutyl]-5,5-di methyl-imidazolidine-2,4-dione;
(5S)-3-[3-(5-methoxyspiro[2H-benzofuran-3,1'-cyclopropane]-4-yl)oxycyclobutyl]-5-methyl-imidazolidine-2,4-dione;

(5R)-3-[3-(5-methoxyspiro[2H-benzofuran-3,1'-cyclopropane]-4-yl)oxycyclobutyl]-5-methyl-imidazolidine-2,4-dione;
(5S)-5-ethyl-3-[3-(5-methoxyspiro[2H-benzofuran-3,1'-cyclopropane]-4-yl)oxycyclobutyl]imidazolidine-2,4-dione;
(5R)-5-ethyl-3-[3-(5-methoxyspiro[2H-benzofuran-3,1'-cyclopropane]-4-yl)oxycyclobutyl]imidazolidine-2,4-dione;
(5S)-5-ethyl-3-[3-(5-methoxyspiro[2H-benzofuran-3,1'-cyclopropane]-4-yl)oxycyclobutyl]-5-methyl-imidazolidine-2,4-dione (5R)-5-ethyl-3-[3-(5-methoxyspiro[2H-benzofuran-3,1'-cyclopropane]-4-yl)oxycyclobutyl]-5-methyl-imidazolidine-2,4-dione;
(5R)-7-[3-(6-methoxyspiro[2H-benzofuran-3,1'-cyclopropane]-4-yl)oxycyclobutyl]-3-oxa-7,9-diazaspiro[4.4]nonane-6,8-dione;
(5S)-7-[3-(6-methoxyspiro[2H-benzofuran-3,1'-cyclopropane]-4-yl)oxycyclobutyl]-3-oxa-7,9-diazaspiro[4.4]nonane-6,8-dione;
3-[3-(6-methoxyspiro[2H-benzofuran-3,1'-cyclopropane]-4-yl)oxycyclobutyl]imidazolidine-2,4-dione;
6-[3-(6-methoxyspiro[2H-benzofuran-3,1'-cyclopropane]-4-yl)oxycyclobutyl]-2-oxa-6,8-diazaspiro[3.4]octane-5,7-dione;
3-[3-(6-methoxyspiro[2H-benzofuran-3,1'-cyclopropane]-4-yl)oxycyclobutyl]-5,5-di methyl-imidazolidine-2,4-dione;
(5S)-3-[3-(6-methoxyspiro[2H-benzofuran-3,1'-cyclopropane]-4-yl)oxycyclobutyl]-5-methyl-imidazolidine-2,4-dione;
(5R)-3-[3-(6-methoxyspiro[2H-benzofuran-3,1'-cyclopropane]-4-yl)oxycyclobutyl]-5-methyl-imidazolidine-2,4-dione;
(5S)-5-ethyl-3-[3-(6-methoxyspiro[2H-benzofuran-3,1'-cyclopropane]-4-yl)oxycyclobutyl]imidazolidine-2,4-dione;
(5R)-5-ethyl-3-[3-(6-methoxyspiro[2H-benzofuran-3,1'-cyclopropane]-4-yl)oxycyclobutyl]imidazolidine-2,4-dione;
(5S)-5-ethyl-3-[3-(6-methoxyspiro[2H-benzofuran-3,1'-cyclopropane]-4-yl)oxycyclobutyl]-5-methyl-imidazolidine-2,4-dione;
(5R)-5-ethyl-3-[3-(6-methoxyspiro[2H-benzofuran-3,1'-cyclopropane]-4-yl)oxycyclobutyl]-5-methyl-imidazolidine-2,4-dione;
(5R)-7-[3-(7-methoxyspiro[2H-benzofuran-3,1'-cyclopropane]-4-yl)oxycyclobutyl]-3-oxa-7,9-diazaspiro[4.4]nonane-6,8-dione;
(5S)-7-[3-(7-methoxyspiro[2H-benzofuran-3,1'-cyclopropane]-4-yl)oxycyclobutyl]-3-oxa-7,9-diazaspiro[4.4]nonane-6,8-dione;
3-[3-(7-methoxyspiro[2H-benzofuran-3,1'-cyclopropane]-4-yl)oxycyclobutyl]imidazolidine-2,4-dione;
6-[3-(7-methoxyspiro[2H-benzofuran-3,1'-cyclopropane]-4-yl)oxycyclobutyl]-2-oxa-6,8-diazaspiro[3.4]octane-5,7-dione;
3-[3-(7-methoxyspiro[2H-benzofuran-3,1'-cyclopropane]-4-yl)oxycyclobutyl]-5,5-di methyl-imidazolidine-2,4-dione;
(5S)-3-[3-(7-methoxyspiro[2H-benzofuran-3,1-cyclopropane]-4-yl)oxycyclobutyl]-5-methyl-imidazolidine-2,4-dione;
(5R)-3-[3-(7-methoxyspiro[2H-benzofuran-3,1'-cyclopropane]-4-yl)oxycyclobutyl]-5-methyl-imidazolidine-2,4-dione;
(5S)-5-ethyl-3-[3-(7-methoxyspiro[2H-benzofuran-3,1'-cyclopropane]-4-yl)oxycyclobutyl]imidazolidine-2,4-dione;
(5R)-5-ethyl-3-[3-(7-methoxyspiro[2H-benzofuran-3,1'-cyclopropane]-4-yl)oxycyclobutyl]imidazolidine-2,4-dione;
(5S)-5-ethyl-3-[3-(7-methoxyspiro[2H-benzofuran-3,1'-cyclopropane]-4-yl)oxycyclobutyl]-5-methyl-imidazolidine-2,4-dione;
(5R)-5-ethyl-3-[3-(7-methoxyspiro[2H-benzofuran-3,1-cyclopropane]-4-yl)oxycyclobutyl]-5-methyl-imidazolidine-2,4-dione;
4-[3-(1,3-dioxo-8-oxa-2,4-diazaspiro[4.5]decan-2-yl)cyclobutoxy]spiro[2H-benzofuran-3,1'-cyclopropane]-7-carbonitrile;
4-[3-(1,3-dioxo-8-oxa-2,4-diazaspiro[4.5]decan-2-yl)cyclobutoxy]spiro[2H-benzofuran-3,1'-cyclopropane]-6-carbonitrile; and
4-[3-(1,3-dioxo-8-oxa-2,4-diazaspiro[4.5]decan-2-yl)cyclobutoxy]spiro[2H-benzofuran-3,1'-cyclopropane]-5-carbonitrile;
or a pharmaceutically acceptable salt and/or solvate thereof and/or derivative thereof.

The term 'halo' or 'halogen' as used herein, refers to a fluorine, chlorine, bromine or iodine atom. Particular examples of halo are fluorine and chlorine, especially fluorine.

When the compound contains a $C_{1-4}$alkyl group, whether alone or forming part of a larger group, e.g. $C_{1-4}$alkoxy, the alkyl group may be straight chain, branched, cyclic, or a combination thereof. Examples of $C_{1-4}$alkyl are methyl, ethyl, n-propyl, isopropyl, cyclopropyl, n-butyl, isobutyl, sec-butyl, tert-butyl, and cyclobutyl. Reference to "propyl" includes n-propyl, isopropyl and cyclopropyl, and reference to "butyl" includes n-butyl, isobutyl, sec-butyl, tert-butyl and cyclobutyl. A particular group of exemplary $C_{1-4}$alkyl groups are methyl, ethyl, n-propyl, isopropyl, cyclopropyl, n-butyl, isobutyl, sec-butyl and tert-butyl. Examples of $C_{1-4}$alkoxy include methoxy, ethoxy, propoxy (which includes n-propoxy, isopropoxy and cyclopropoxy) and butoxy.

The term "$C_{1-4}$alkoxy" also extends to embodiments in which the oxygen atom is located within the alkyl chain, for example —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example —$OC_{1-4}$alkyl.

The term 'halo$C_{1-4}$alkyl' as used herein, includes straight chain, branched chain or cyclic alkyl groups containing 1 to 4 carbon atoms substituted by one or more halo atoms, for example fluoromethyl, difluoromethyl and trifluoromethyl. A particular group of exemplary halo$C_{1-4}$ alkyl include methyl and ethyl groups substituted with one to three halo atoms, in particular one to three fluoro atoms, such as trifluoromethyl or 2,2,2-trifluoroethyl.

The term 'halo$C_{1-4}$alkoxy' as used herein, includes straight chain, branched chain or cyclic alkoxy groups containing 1 to 4 carbon atoms substituted by one or more halo atoms, for example fluoromethoxy, difluoromethoxy and trifluoromethoxy. A particular group of exemplary halo$C_{1-4}$ alkyl include methoxy and ethoxy groups substituted with one to three halo atoms, in particular one to three fluoro atoms.

The term '$C_{3-5}$ spiro carbocyclyl' as used herein means a cyclic ring system containing 3 to 5 carbon atoms, for example, a cyclopropyl, cyclobutyl or cyclopentyl group, wherein the cyclic ring system is attached to a secondary carbon via a spirocentre such that the secondary carbon is one of the 3 to 5 carbon atoms in the cyclic ring as follows:

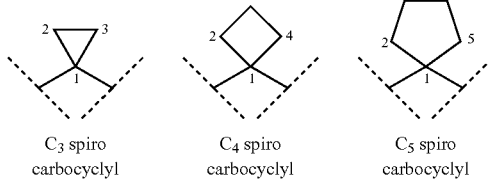

C₃ spiro carbocyclyl      C₄ spiro carbocyclyl      C₅ spiro carbocyclyl

The term 'C$_{2-4}$ spiro heterocyclyl' as used herein means a heterocyclic ring system containing 2 to 4 carbon atoms and at least 1 heteroatom (for example independently O, N or S) wherein the heterocyclic ring system is attached to a secondary carbon via a spirocentre such that the secondary carbon is one of the 2 to 4 carbon atoms in the cyclic ring. Example heterocyclic rings include:

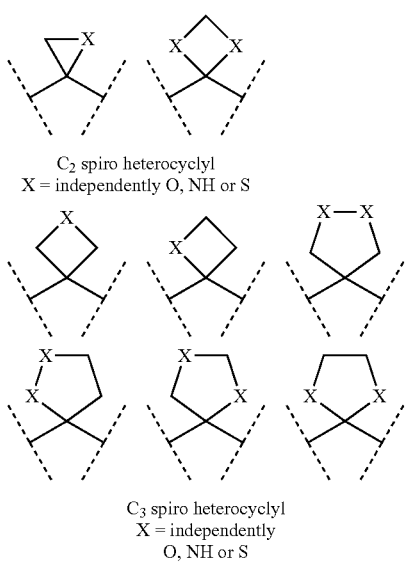

C₂ spiro heterocyclyl
X = independently O, NH or S

C₃ spiro heterocyclyl
X = independently O, NH or S

C₄ spiro heterocyclyl
X = O, NH or S

Similarly, the term 'C$_{2-5}$ spiro heterocyclyl' or 'C$_{3-5}$ spiro heterocyclyl' as used herein means a heterocyclic ring system containing 2 to 5 or 3 to 5 carbon atoms respectively and at least 1 heteroatom (for example independently O, N or S) wherein the heterocyclic ring system is attached to a secondary carbon via a spirocentre such that the secondary carbon is one of the 2 to 5 or 3 to 5 carbon atoms in the cyclic ring. In addition to the rings disclosed above, example heterocyclic rings include:

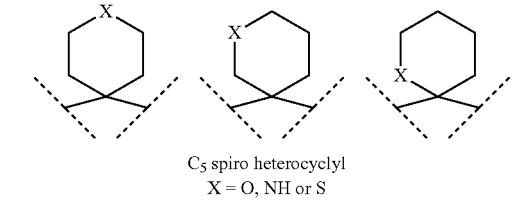

C₅ spiro heterocyclyl
X = O, NH or S

Suitably, the heterocyclic ring system has one heteroatom, such as:

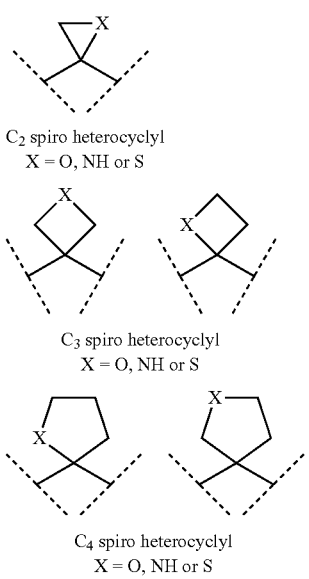

C₂ spiro heterocyclyl
X = O, NH or S

C₃ spiro heterocyclyl
X = O, NH or S

C₄ spiro heterocyclyl
X = O, NH or S

Suitably the C$_{2-4}$ spiro heterocyclyl has one heteroatom, wherein it may also be referred to as a 3-5 membered heterocyclyl.

Suitably the C$_{2-5}$ spiro heterocyclyl has one heteroatom, wherein it may also be referred to as a 3-6 membered heterocyclyl.

Suitably the C$_{2-5}$ spiro heterocyclyl is oxetane, tetrahydrofuran or tetrahydropyran, thereby forming compounds which include the following moieties:

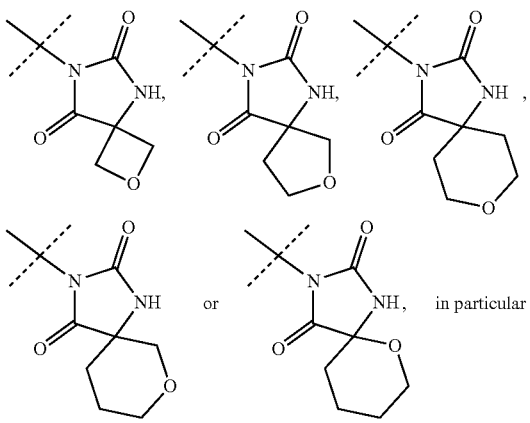

or                    , in particular

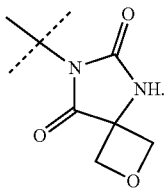

Suitably, the C$_{2-5}$ spiro heterocyclyl is tetrahydropyran and (Za) has the following stereochemistry:

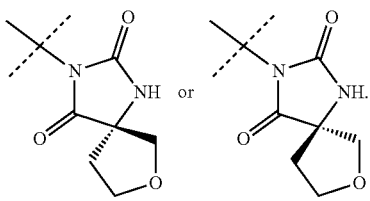

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge et al. (1977). Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

Suitably, a pharmaceutically acceptable prodrug is formed by functionalising the secondary nitrogen of the hydantoin, or the secondary nitrogen of the triazolone, for example with a group "L" as illustrated below:

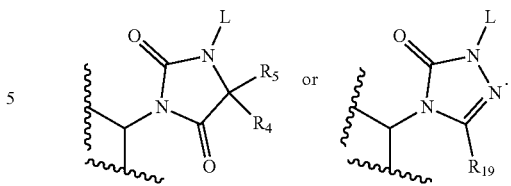

In one embodiment of the invention, a compound of formula (I) is functionalised via the secondary nitrogen of the hydantoin or via the secondary nitrogen of the triazolone with a group L as illustrated directly above, wherein L is selected from:
a) —PO(OH)O—.M+, wherein M+ is a pharmaceutically acceptable monovalent counterion,
b) —PO(O—)$_2$.2M+,
c) —PO(O—)$_2$.D2+, wherein D2+ is a pharmaceutically acceptable divalent counterion,
d) —CH(RX)—PO(OH)O-.M+, wherein RX is hydrogen or C$_{1-3}$ alkyl,
e) —CH(RX)—PO(O—)$_2$.2M+,
f) —CH(RX)—PO(O—)$_2$.D2+,
g) —SO$_3$-.M+,
h) —CH(RX)—SO$_3$-.M+, and
i) —CO—CH$_2$CH$_2$—CO$_2$.M+.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject invention also includes isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as $^2$H (deuterium), $^3$H, $^{11}$C, $^{13}$C, $^{14}$C, $^{18}$F, $^{123}$I or $^{125}$I (e.g. $^3$H, $^{11}$C, $^{14}$C, $^{18}$F, $^{123}$I or $^{125}$I), which may be naturally occurring or non-naturally occurring isotopes.

Compounds of the present invention and pharmaceutically acceptable salts of said compounds that contain the aforementioned isotopes and/or other isotopes of other atoms are within the scope of the present invention. Isotopically labelled compounds of the present invention, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Suitably the compounds of the invention are provided in the form of the free base.

In general, the compounds of formula (I) may be made according to the organic synthesis techniques known to those skilled in this field, as well as by the representative methods set forth below, those in the Examples, and modifications thereof.

Patent applications WO2011/069951, WO2012/076877, WO2012/168710 and WO2013/175215 provide methods for the synthesis of intermediates which may be of use in the production of compounds of the present invention. WO2017/103604 provides methods for the synthesis of intermediates which may be of use in the production of compounds of the present invention.

In the following description, the groups A, R', R'', $R_1$, $R_2$, $R_3$, $R_4$, $R_5$, $R_{13}$, $R_{14}$, $R_{16}$, $R_{17}$, $R_{18}$, $R_{19}$, $R_{20}$, $R_{21}$, $R_{22}$, $R_{23}$, $R_{24}$, $R_{30}$, $R_{31}$ and W, (Wa), (Wb), (Wc), (Wc-a), (Wc-b), Z, (Za) and (Zb) have the meanings as previously defined for compounds of formula (I) unless otherwise stated.

General Synthesis Schemes

The following schemes detail synthetic routes to compounds of the invention and intermediates in the synthesis of such compounds. In the following schemes reactive groups can be protected with protecting groups and deprotected according to established techniques well known to the skilled person. In the following schemes X and Y are both H.

Preparation of Compounds of Formula (I-IV) (Wherein Z is Group (Za)—Hydantoin)

Scheme 1a

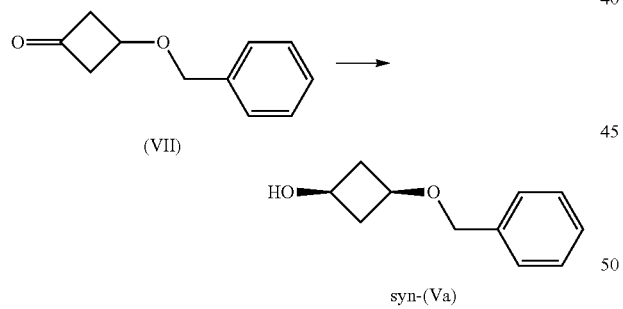

Alcohols of syn configuration of formula (Va) can be obtained via reduction of the commercially available ketone of formula (VII) using sodium borohydride in a solvent such as methanol at 0° C. (Mitchell, 2015).

Scheme 1b

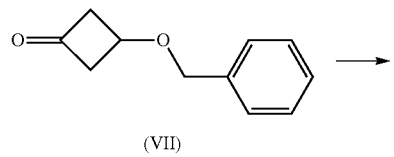

-continued

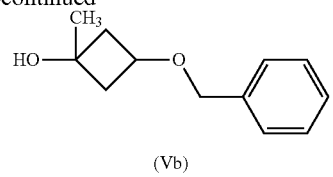

Alcohols of formula (Vb) can be obtained by reacting the commercially available ketone of formula (VII) with a suitable source of "$CH_3^-$" for example a methyl Grignard reagent such as methyl magnesium bromide.

Scheme 2

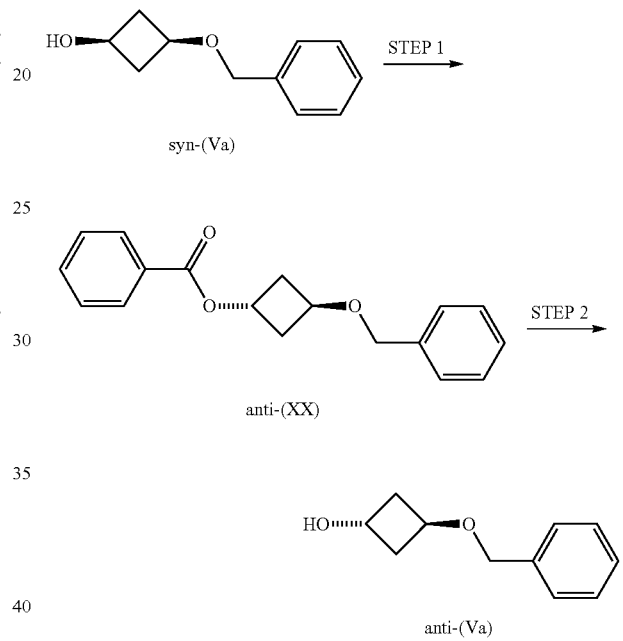

Step 1

Esters of anti configuration of formula (XX) can be obtained via Mitsunobu reaction by reacting the alcohol of formula syn-(Va) and benzoic acid using DIAD or DEAD and a phosphine such as triphenylphosphine in a solvent such as THF at a temperature ranging from 0° C. to reflux.

Step 2

Alcohols of anti configuration of formula (Va) can be obtained via hydrolysis of esters of formula anti-(XX) by using a hydroxide such as LiOH, NaOH or KOH in a solvent such as MeOH or water or THF or a mixture thereof, at a temperature ranging from 0° C. to reflux.

Scheme 3a

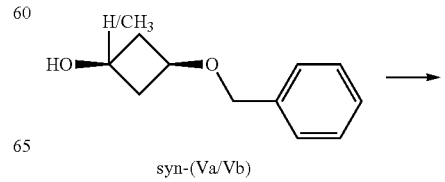

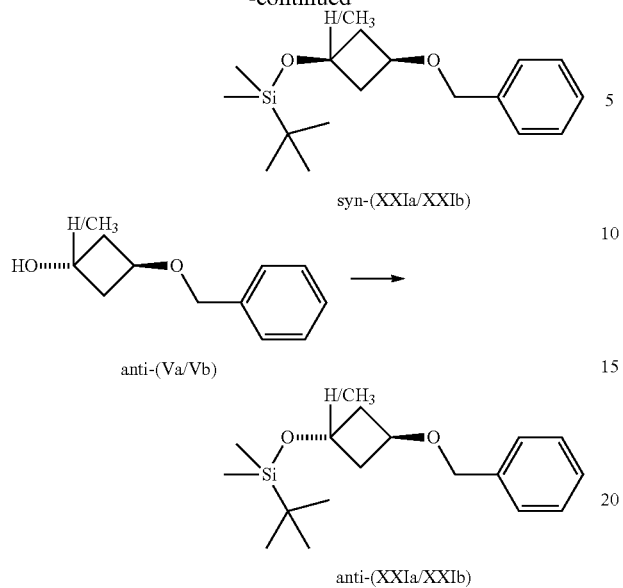

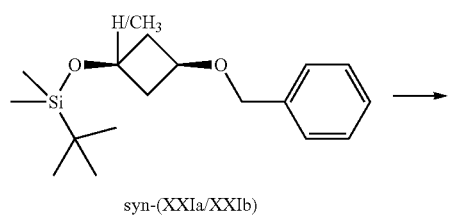

Silylated compounds of formulae (XXIa) and (XXIb) can be obtained by reacting alcohols of formulae (Va) and (Vb) with tert-butyldimethylsilyl chloride in a solvent such as DCM in the presence of a base such as imidazole at temperature ranging from 0° C. to r.t.

Alcohols of formulae (XXIIa) and (XXIIb) can be obtained via debenzylation of ethers of formulae (XXIa) and (XXIb) using H$_2$ in the presence of a catalyst such as Pd/C in a solvent such as MeOH or EtOH at a temperature ranging from r.t. to reflux.

Alternatively alcohols of formulae (XXIIa) and (XXIIb) can be obtained via debenzylation of ethers of formulae (XXIa) and (XXIb) using ammonium formate in the presence of a catalyst such as Pd/C in a solvent such as MeOH or EtOH at a temperature ranging from r.t. to reflux.

Scheme 4a

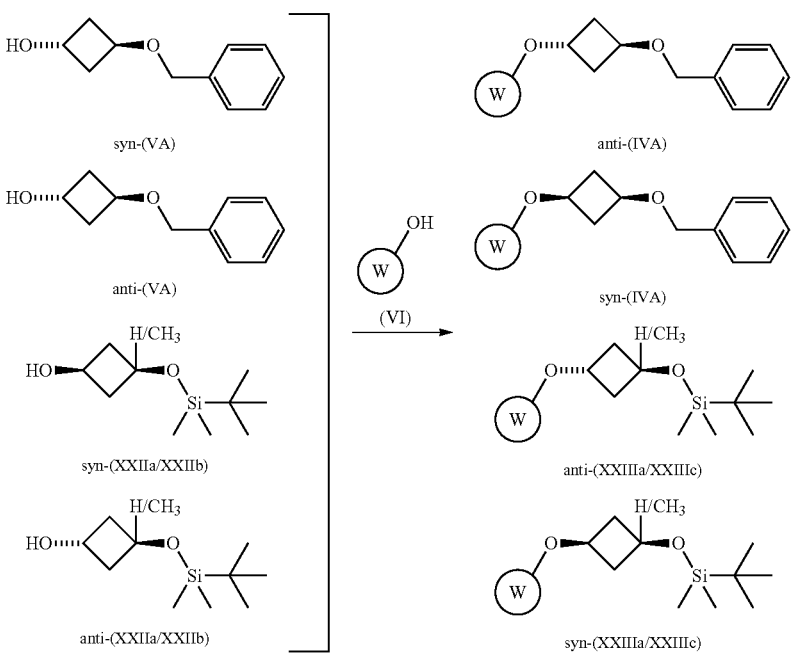

Ethers of formulae (IVa), (XXIIIa) and (XXIIc) can be obtained via Mitsunobu reaction by reacting an alcohol of formulae (Va), (XXIIa) or (XXIIIb), respectively, and a phenol of formula (VI) using diisopropyl azodicarboxylate (DIAD) or diethyl azodicarboxylate (DEAD) and a phosphine such as triphenylphosphine in a solvent such as Et$_2$O, toluene or THF at a temperature ranging from 0° C. to reflux.

Scheme 4b

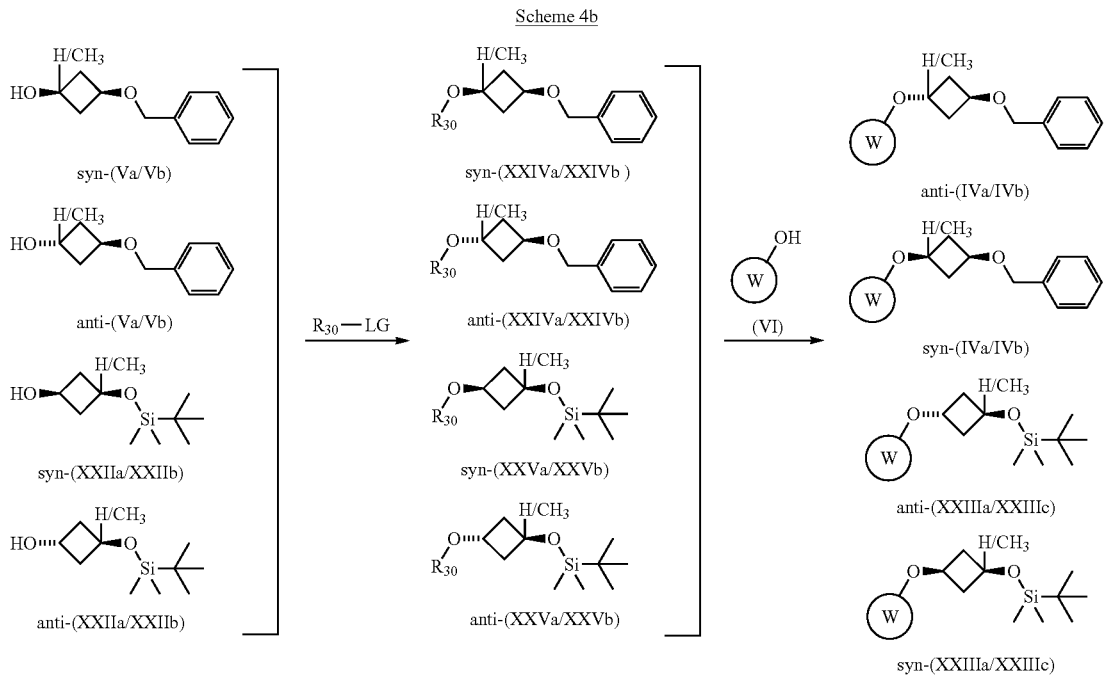

Alternatively ethers of formulae (IVa), (IVb), (XXIIIa) and (XXIIc) can be obtained by reacting an alcohol of formulae (Va), (Vb), (XXIIa) or (XXIIb), respectively, with R$_{30}$-LG, wherein LG is a leaving group e.g. Cl and R$_{30}$ is a suitable group which renders —OR$_{30}$ a leaving group (e.g. R$_{30}$-LG is mesyl chloride or tosyl chloride) in presence of a base such as trimethylamine in a solvent such as DCM at a temperature ranging from 0° C. to r.t. and further reacting the compound of formulae (XXIV) or (XXVa) with a phenol of formula (VI) in presence of a base such as potassium carbonate or Cesium carbonate in a solvent such as acetonitrile or DMF at a temperature ranging from 0° C. to reflux.

Scheme 5a

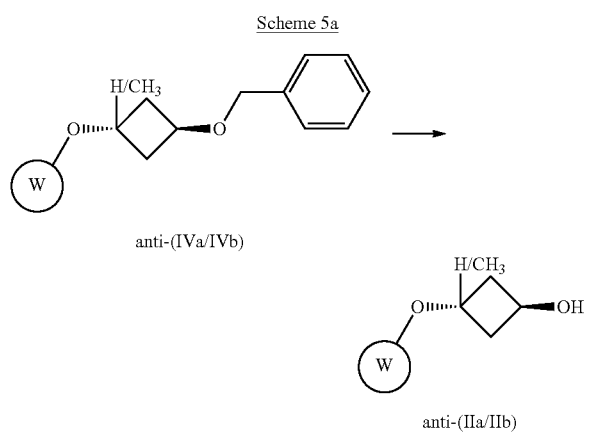

-continued

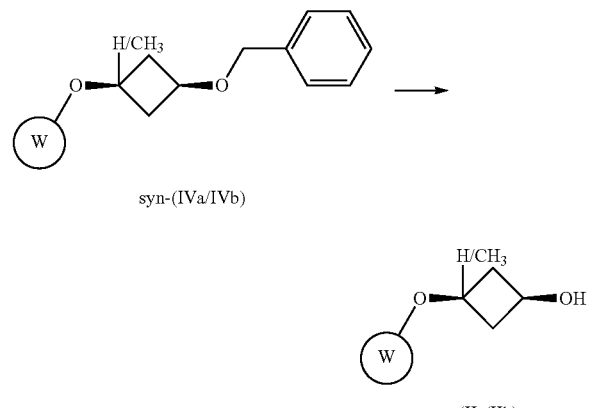

Alcohols of formula (IIa) and formula (IIb) can be obtained via debenzylation of ethers of formulae (IVa) and (IVb) using H$_2$ in the presence of a catalyst such as Pd/C in a solvent such as MeOH or EtOH at a temperature ranging from r.t. to reflux.

Alternatively alcohols of formula (IIa) and formula (IIb) can be obtained via debenzylation of ethers of formulae (IVa) and (IVb) using ammonium formate in presence of a catalyst such as Pd/C in a solvent such as MeOH or EtOH at a temperature ranging from r.t. to reflux.

Scheme 5b

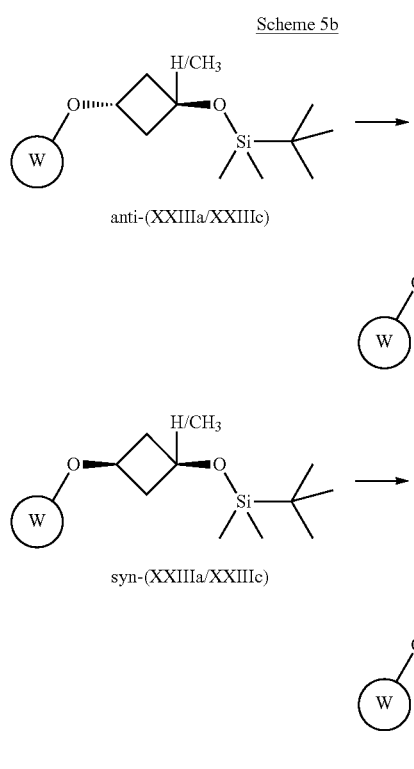

anti-(XXIIIa/XXIIIc)

anti-(IIa/IIc)

syn-(XXIIIa/XXIIIc)

syn-(IIa/IIc)

Alcohols of formula (IIa) and formula (IIc) can be obtained via desilylating ethers of formulae (XXIIIa) and (XXIIIc) in presence of a fluoride such as tetrabutylammonium fluoride or cesium fluoride in a solvent such as THF or acetonitrile at a temperature ranging from 0° C. to reflux.

Scheme 6

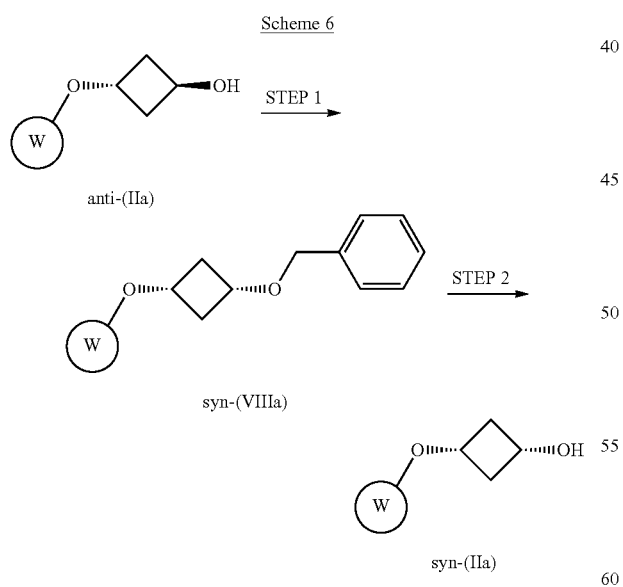

anti-(IIa)

syn-(VIIIa)

syn-(IIa)

Step 1

Esters of syn configuration of formula (VIIIa) can be obtained via Mitsunobu reaction by reacting the alcohol of formula anti-(IIa) and benzoic acid using DIAD or DEAD and a phosphine such as triphenylphosphine in a solvent such as THF at a temperature ranging from 0° C. to reflux.

Step 2

Alcohols of syn configuration of formula (IIa) can be obtained via hydrolysis of esters of formula syn-(VIIIa) by using a hydroxide such as LiOH, NaOH or KOH in a solvent such as MeOH or water or THF or a mixture thereof, at a temperature ranging from 0° C. to reflux.

Scheme 7

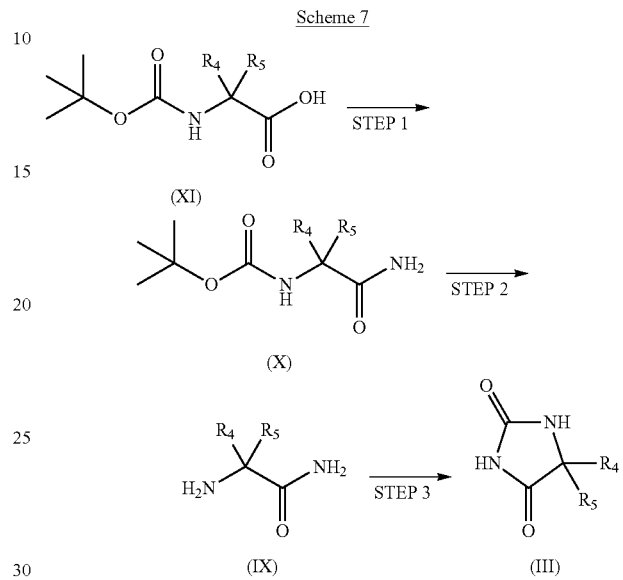

(XI)

(X)

(IX)

(III)

Step 1

Boc-protected aminoamides of formula (X) can be prepared from commercially available Boc-protected aminoacids of formula (XI) using HMDS in presence of a coupling agent such as TBTU and a base such as DIPEA in a solvent such as DCM or DMF or a mixture thereof, at r.t.

Step 2

Aminoamides of formula (IX) (isolated as free bases or trifluoroacetate salts) can be prepared from the relative Boc-protected aminoamides of formula (X) by using TFA in a solvent such as DCM at a temperature ranging from 0° C. to r.t.

Step 3

Hydantoins of formula (III), if not commercially available, can be prepared from aminoamides of formula (IX) using a carbonylating agent such as triphosgene in presence of a base such as DIPEA in a solvent such as DCM at a temperature ranging from 0° C. to r.t.

Scheme 8a anti-(IIa/IIb)

(III)

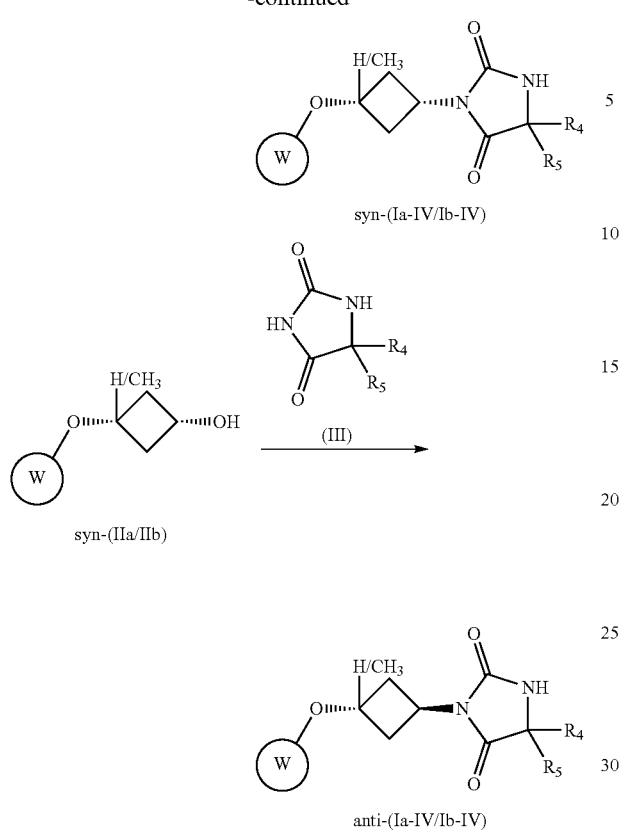

syn-(Ia-IV/Ib-IV)

syn-(IIa/IIb)

anti-(Ia-IV/Ib-IV)

Compounds of formula (Ia-IV) and formula (Ib-IV) can be obtained via Mitsunobu reaction by reacting the alcohol of formulae (IIa) or (IIb) with the hydantoin of formula (III) using DIAD or DEAD and a phosphine such as tiphenylphosphine in a solvent such as THF at a temperature ranging from 0° C. to reflux.

Scheme 8b

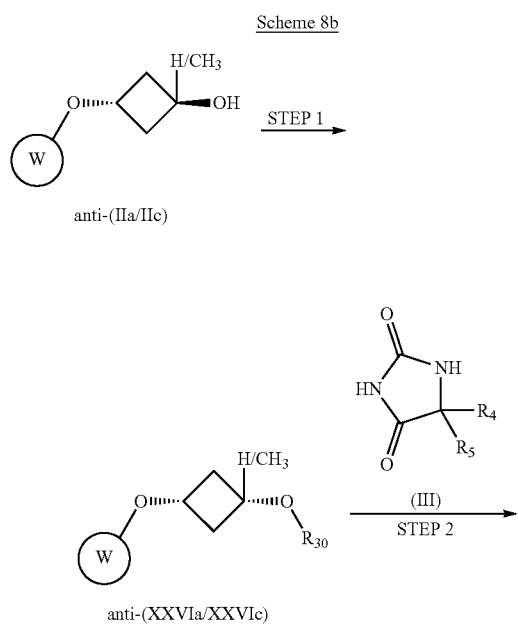

anti-(IIa/IIc)

anti-(XXVIa/XXVIc)

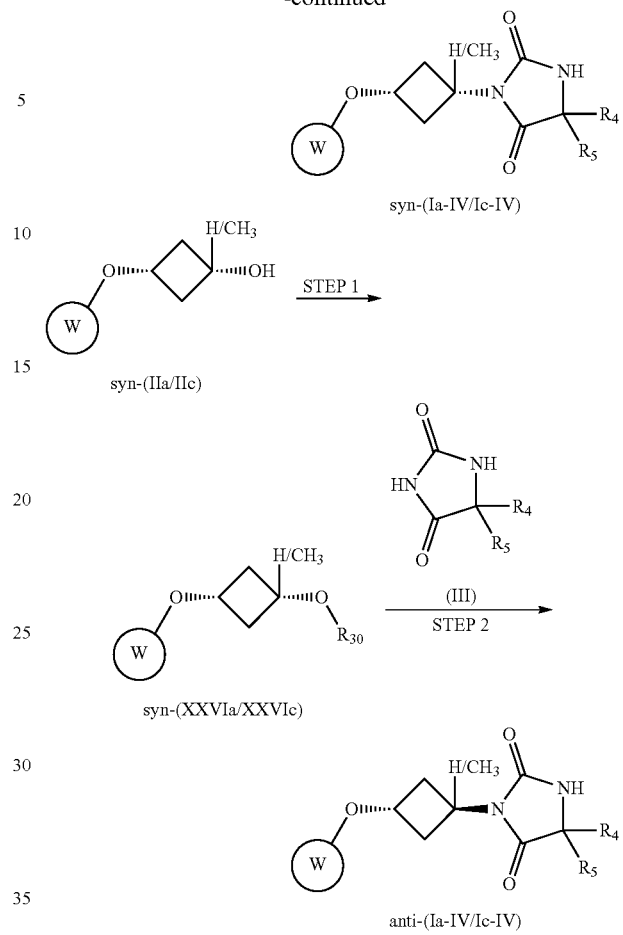

syn-(Ia-IV/Ic-IV)

syn-(IIa/IIc)

syn-(XXVIa/XXVIc)

anti-(Ia-IV/Ic-IV)

Compounds of formula (Ia-IV) and formula (Ic-IV) can be obtained by reacting an alcohol of formulae (IIa) or (IIc) with $R_{30}$-LG, wherein LG is a leaving group e.g. Cl and $R_{30}$ is a suitable group which renders —$OR_{30}$ a leaving group (e.g. $R_{30}$-LG is mesyl chloride or tosyl chloride) in the presence of a base such as trimethylamine in a solvent such as DCM at a temperature ranging from 0° C. to r.t. to form a compound of formula (XXVI) (STEP 1). The compound of formulae (XXVIa/c) is then reacted with hydantoin of formula (III) in the presence of a base such as sodium hydride in a solvent such as tetrahydrofuran or DMF at a temperature ranging from 0° C. to reflux or a base such as potassium carbonate in a solvent such as acetonitrile or DMF at a temperature ranging from 0° C. to reflux (STEP 2).

Alternatively, compounds of formula (Ia-IV) can be made via a Mitsonobu reaction of the alcohols of (XXVIIIa) with a phenol of formula (VI).

Scheme 9

Step 1

Hydantoine derivatives of formula (XXVIIIa) can be obtained via Mitsunobu reaction by reacting the alcohol of formulae (XXIIa) with the hydantoin of formula (III) using DIAD or DEAD and a phosphine such as tiphenylphosphine in a solvent such as THF at a temperature ranging from 0° C. to reflux.

Step 2

Alcohols of formula (XXVIIIa) can be obtained desilylating hydantoin derivatives of formula (XXVIIIa) in presence of a fluoride such as tetrabutylammonium fluoride or cesium fluoride in a solvent such as THF or acetonitrile at a temperature ranging from 0° C. to reflux.

Step 3

Compounds of formulae (Ia-IV) can be obtained via Mitsunobu reaction by reacting an alcohol of formulae (XXVIIIa) and a phenol of formula (VI) using diisopropyl azodicarboxylate (DIAD) or diethyl azodicarboxylate (DEAD) and a phosphine such as triphenylphosphine in a solvent such as Et$_2$O, toluene or THF at a temperature ranging from 0° C. to reflux.

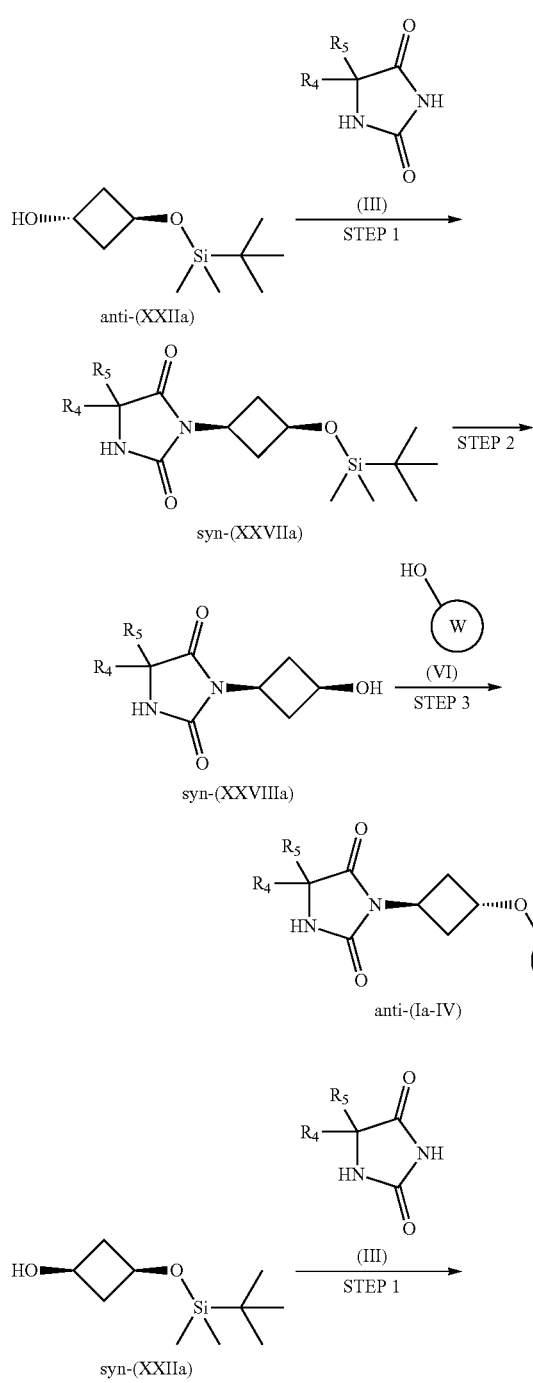

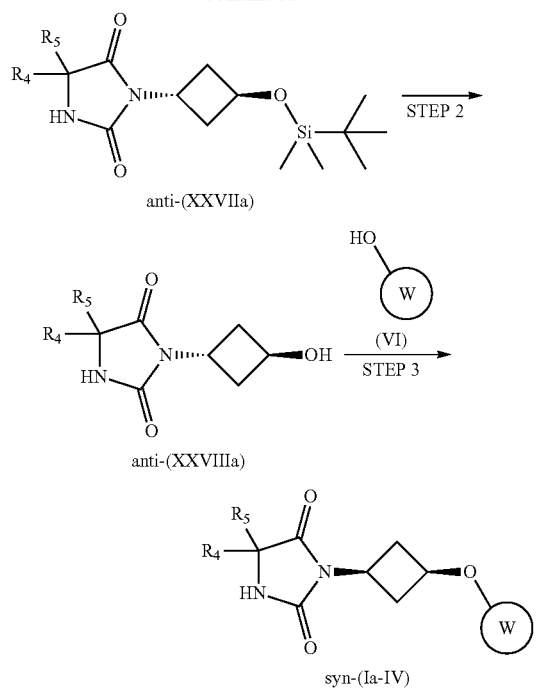

Alternatively, compounds of formula (I-IVa), (I-IVb) and (I-IVc) can be made via a coupling reaction between amines of formula (XIIa) and protected amino-acids, followed by a deprotection and cyclisation step.

Scheme 10

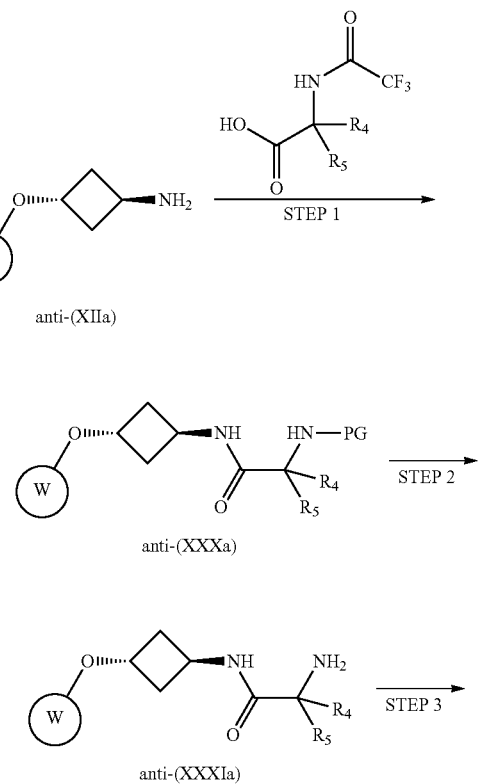

Preparation of Compounds of Formula (I-V) (Wherein Z is Group (Zb)—Triazolone)

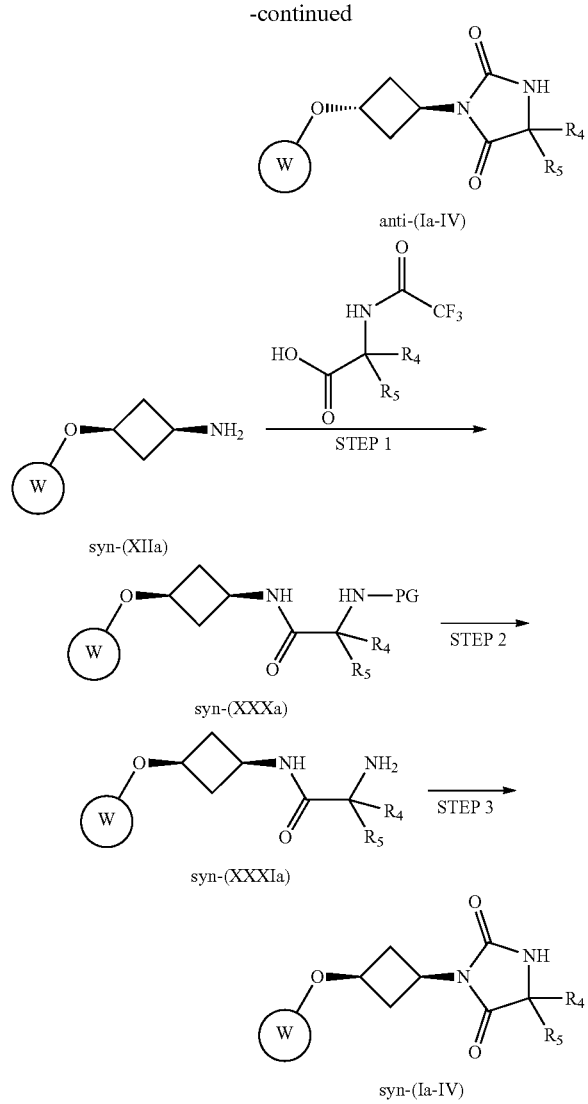

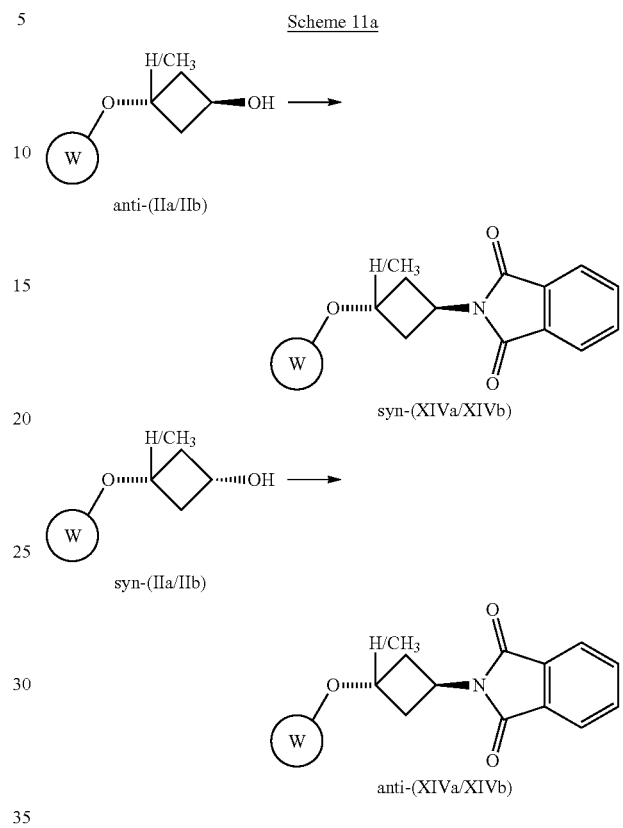

Step 1

Amides of formula (XXXa) can be obtained by reacting amines of formula (XIIa) and CF₃CO—N-protected amino acids in presence of a coupling agent such as TBTU and a base such as DIPEA in a solvent such as DCM or DMF or a mixture thereof, at r.t. or PPh₃ in presence of a base such as DIPEA or TEA in a solvent such as Ethyl Acetate or Acetonitrile or a mixture thereof at a temperature ranging from 0° C. to room temperature.

Step 2

Amines of formula (XXXIa) can be obtained by cleavage of the CF₃CO— protecting group using an hydroxide such as Lithium hydroxide in a mixture of solvents such as Methanol/water or THF/water or Methanol/THF/water at a temperature ranging from 0° C. to reflux.

Step 3

Compounds of formula (Ia-IV) can be prepared from amines of formula (XXXI) using a carbonylating agent such as triphosgene in presence of a base such as triethylamine in a solvent such as DCM at a temperature ranging from 0° C. to room temperature.

Phthalimide derivatives of formula (XIVa) and formula (XIVb) can be obtained via Mitsunobu reaction by reacting the alcohol of formulae (IIa) or (IIb) with phthalimide using DIAD or DEAD and a phosphine such as triphenylphosphine in a solvent such as THF at a temperature ranging from 0° C. to reflux.

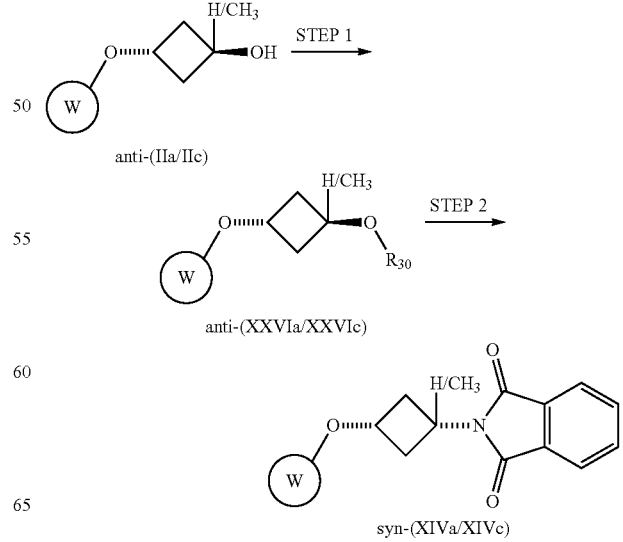

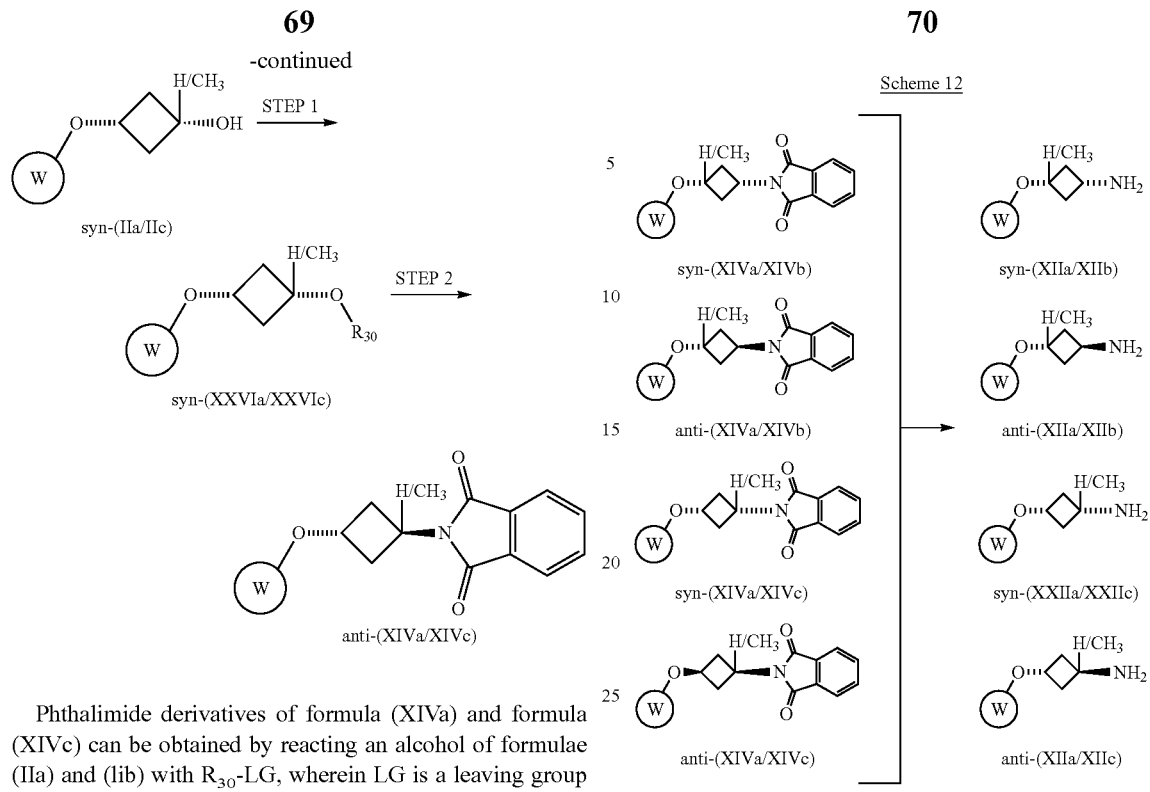

Phthalimide derivatives of formula (XIVa) and formula (XIVc) can be obtained by reacting an alcohol of formulae (IIa) and (IIb) with $R_{30}$-LG, wherein LG is a leaving group e.g. Cl and $R_{30}$ is a suitable group which renders —$OR_{30}$ a leaving group (e.g. $R_{30}$-LG is mesyl chloride or tosyl chloride) in presence of a base such as trimethylamine in a solvent such as DCM at a temperature ranging from 0° C. to r.t. to form a compound of formula (XXVIa) or formula (XXVIc) (STEP 1). The compound of formulae (XXVIa) or (XXVIc) is then reacted with phthalimide in the presence of a base such as sodium hydride in a solvent such as tetrahydrofuran or DMF at a temperature ranging from 0° C. to reflux to give compounds of formulae (XIVa) and (XIVc).

Amines of formulae (XIIa), (XIIb) and (XIIc) can be obtained from phthalimide derivatives of formulae (XIVa), (XIVb) and (XIVc) by reaction with hydrazine in a solvent such as MeOH or EtOH at temperature ranging from 0° C. to reflux.

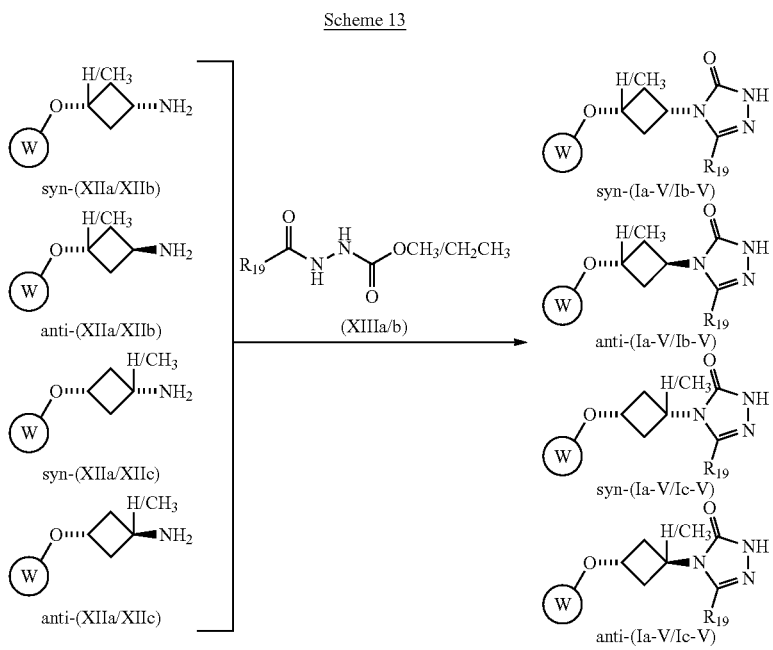

Compounds of formulae (Ia-V), (Ib-V) and (Ic-V) can be obtained from amines of formulae (XIIa), (XIIb) and (XIIc) by reacting with a compound of formula (XIIIa/b) in a solvent such as MeOH at reflux with optional addition of an acid catalyst such as PTSA.

Preparation of Phenols of Formula Wa, Wb and Wc
Phenols of Formula Wa

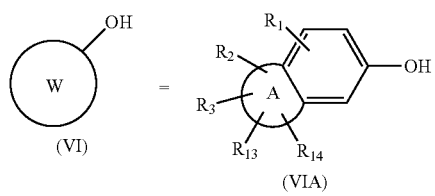

Phenols of formula (VIA) can be prepared accordingly to procedures described into patent application WO2012/168710 which is incorporated by reference for the purpose of providing methods for the synthesis of phenols of formula (VIA).

Phenols of Formula Wb

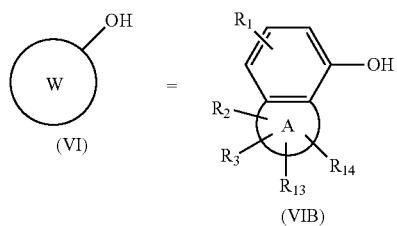

Phenols of formula (VIB) can be prepared accordingly to procedures described into patent application WO2012/076877 which is incorporated by reference for the purpose of providing methods for the synthesis of phenols of formula (VIB).

Alternatively, phenols of formula (VIB) wherein $R_1$ is CN can be made by the synthetic route in Scheme 14.

Step 1
Silylated phenol of formula (VIB-b) can be obtained by reacting phenols of formula (VIB-a) with a TDBMS-Cl in presence of a base such as imidazole in a solvent such as DCM at temperature ranging from 0° C. to room temperature.

Step 2
Brominated compound of formula (VIB-c) can be obtained by treating silylated phenols of formula (VIB-b) with a brominating agent such as NBS in a solvent such THF at temperature ranging from 0° C. to room temperature.

Step 3
Aldehyde of formula (VIB-d) can be obtained by treating brominated compound of formula (VIB-c) with butyllithium and quenching the carbanion intermediate with a carbonyl source such as DMF in a solvent such as dry THF or dry hexane or a mixture thereof at temperature ranging from −78° C. to room temperature. The TBDMS protecting group is removed by using a fluoride such as tetrabutylammonium fluoride or cesium fluoride in a solvent such as THF or acetonitrile at a temperature ranging from 0° C. to reflux.

Step 4
Oxime of formula (VIB-e) can be prepared by treating aldehydes of formula (VIB-d) with hydroxylamine. HCl in presence of a base such as potassium carbonate in a solvent such as methanol at a temperature ranging from 0° C. to reflux.

Step 5
Compound of formula (VIB-f) can be prepared by refluxing oxime of formula (VIB-e) in acetic anhydride.

Step 6
Phenol of formula (VIB-g) can be prepared by hydrolyzing the esters of formula (VIB-f) with a hydroxide such as sodium hydroxide in a mixture of solvents such as methanol/water or THF/water or methanol/THF/water at a temperature ranging from 0° C. to reflux.

Phenols of Formula Wc

Scheme 14

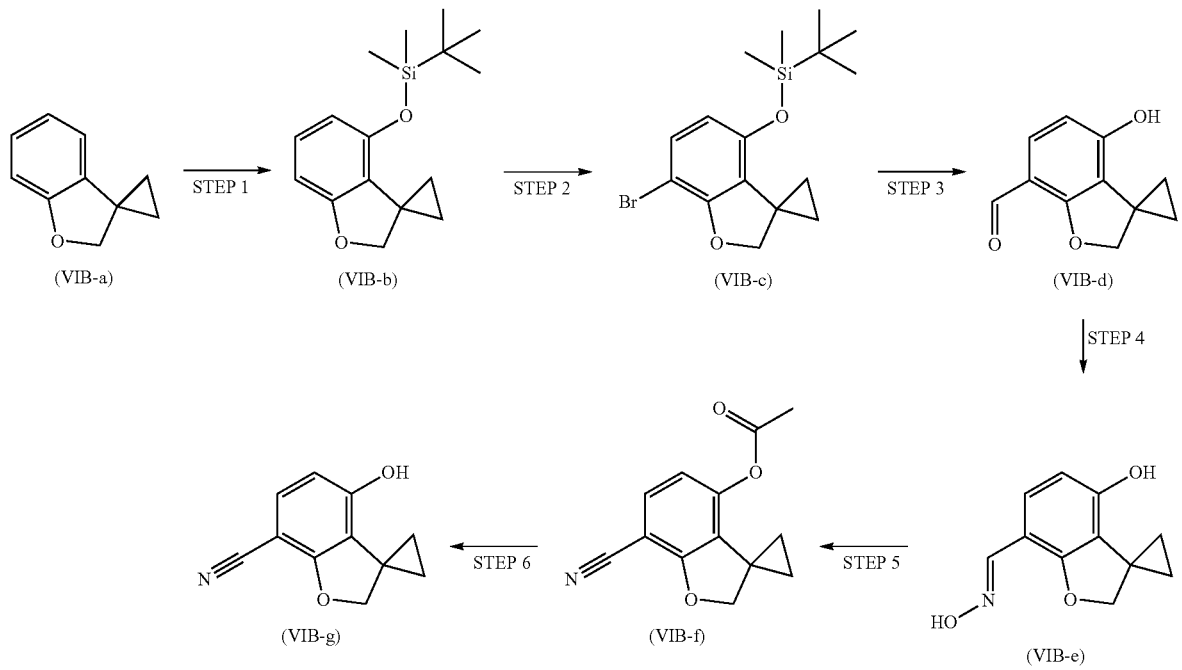

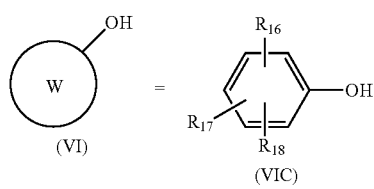

Phenols of formula (VIC), if not commercially available, can be prepared accordingly to procedures described into patent application WO2011/069951 which is incorporated by reference for the purpose of providing methods for the synthesis of phenols of formula (VIC).

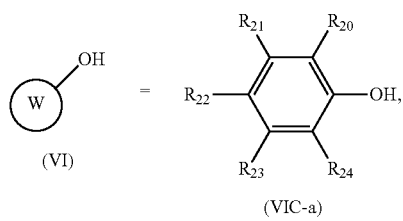

Phenols of formula (VIC-a), if not commercially available, can be prepared accordingly to procedures described into patent application WO2013/175215 which is incorporated by reference for the purpose of providing methods for the synthesis of phenols of formula (VIC-a).

Processes of the Invention

According to further aspects of the present invention are provided processes for the preparation of compounds of formula (I) and derivatives thereof, as well as processes for preparing intermediates in the synthesis of compounds of formula (I).

In one embodiment is provided a process comprising reacting a compound of formula (XVac) with a compound of formula (VI) under Mitsunobu conditions to give a compound of formula (XVIac):

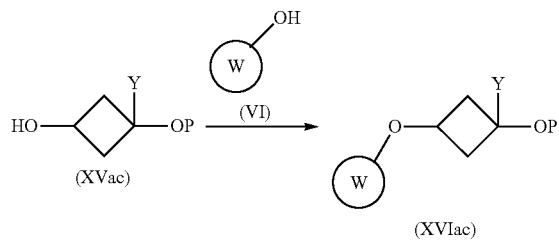

wherein groups W and Y are as defined above, P is a suitable protecting group, and wherein compounds of formulae (XVac) and (XVIac) have the opposite relative stereochemistry.

Suitably, this process comprises reacting a compound of formula syn-(XVac) with a compound of formula (VI) under Mitsunobu conditions to give a compound of formula anti-(XVIac):

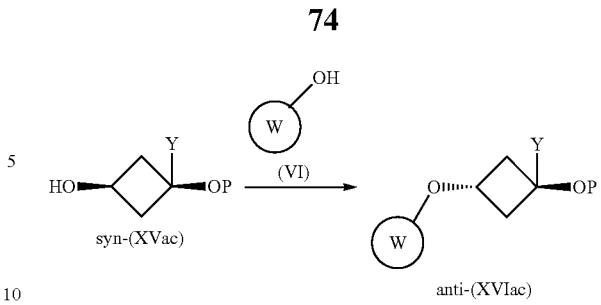

wherein groups W and Y are as defined above, and P is a suitable protecting group.

In one embodiment is provided a process comprising reacting a compound of formula (XV) with $R_{30}$-LG under suitable conditions to form a compound of formula (XXIX), followed by reaction with compound of formula (VI) under basic conditions to give a compound of formula (XVI):

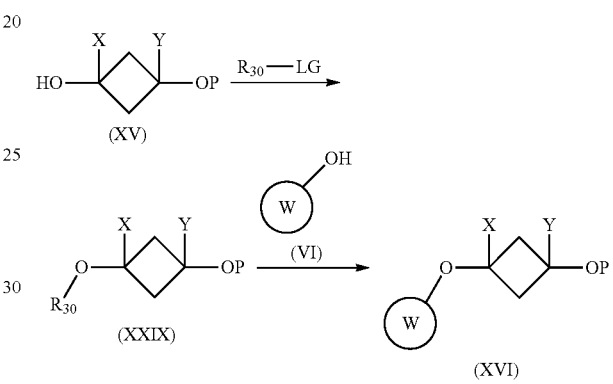

wherein groups W, X and Y are as defined above, P is a suitable protecting group, LG is a leaving group and $R_{30}$ is a suitable group which renders $—OR_{30}$ a leaving group, and wherein compounds of formulae (XV) and (XVI) have the opposite relative stereochemistry.

Suitably this process comprises reacting a compound of formula syn-(XV) with $R_{30}$-LG under suitable conditions to form a compound of formula syn-(XXIX), followed by reaction with a compound of formula (VI) under basic conditions to give a compound of formula anti-(XVI):

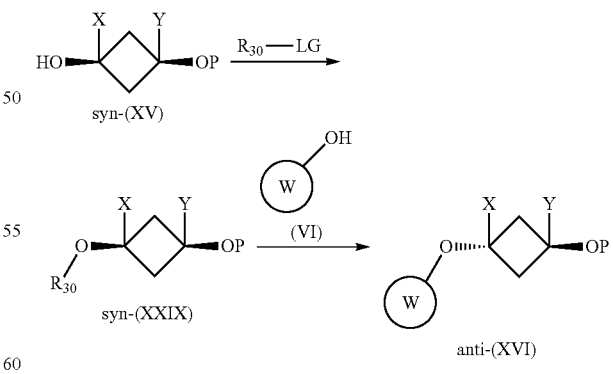

wherein groups W, X and Y are as defined above, LG is a leaving group, P is a suitable protecting group and $R_{30}$ is a suitable group which renders $—OR_{30}$ a leaving group.

In one embodiment is provided a process comprising deprotecting a compound of formula (XVI) under suitable conditions to give a compound of formula II):

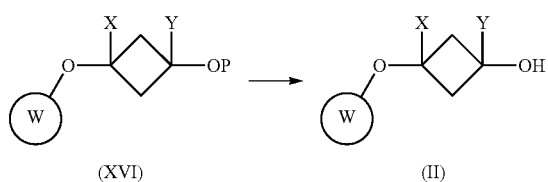

(XVI) → (II)

wherein groups W, X and Y are as defined above, and P is a suitable protecting group.

Suitably, this process comprises deprotecting a compound of general formula anti-(XVI) under suitable conditions to give a compound of formula anti-(II):

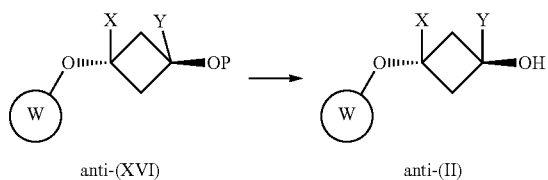

anti-(XVI)  anti-(II)

wherein groups W, X and Y are as defined above, and P is a suitable protecting group.

In one embodiment is provided a process comprising reacting a compound of formula (IIab) under Mitsunobu conditions to give a compound of formula (XVIIab) with the opposite stereochemistry, followed by hydrolysis to give a compound of formula (IIab) with retention of stereochemistry (overall giving a compound of formula (IIab) with opposite stereochemistry relative to the starting compound of formula (IIab)):

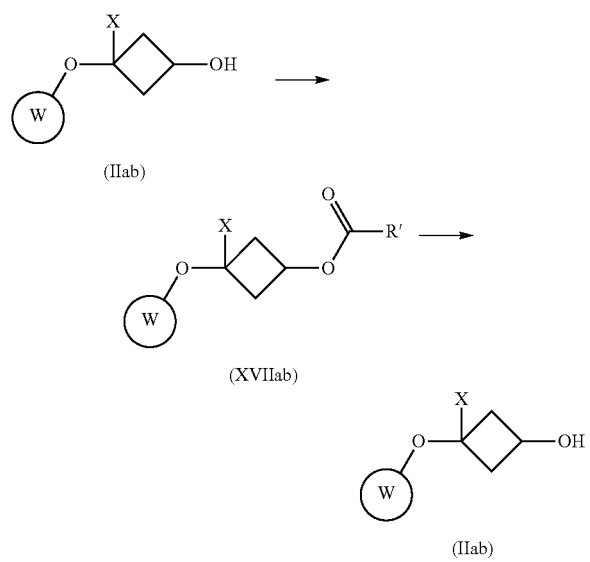

wherein groups W and X are as defined above and R' is a substituted or unsubstituted alkyl, substituted or unsubstituted phenyl or substituted or unsubstituted benzyl group, and is suitably phenyl.

In this embodiment, the compound of formula (IIab) is epimerized i.e. the stereochemistry of the hydroxyl group not bearing group W is reversed during the Mitsunobu reaction. Suitably this process comprises reacting a compound of formula anti-(IIab) under Mitsunobu conditions to give an ester of formula syn-(XVIIab), followed by hydrolysis to give a compound of formula syn-(IIab):

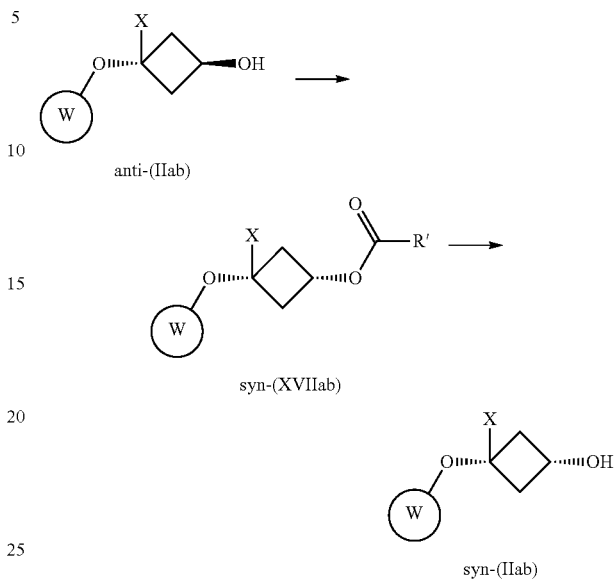

wherein groups W and X are as defined above and R' is a substituted or unsubstituted alkyl, substituted or unsubstituted phenyl or substituted or unsubstituted benzyl group, and is suitably phenyl.

In one embodiment is provided a process comprising reacting a compound of formula (II) to give a compound of formula (I):

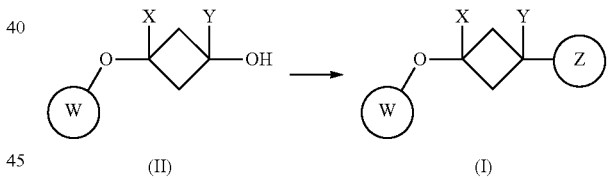

(II) → (I)

wherein W and Z are as defined above.

In one embodiment is provided a process comprising reacting a compound of formula (IIab) with hydantoin (III) under Mitsunobu conditions to give a compound of formula (I-IVab):

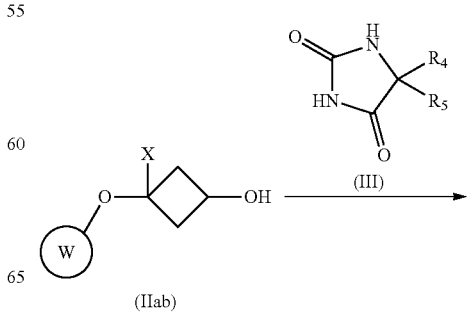

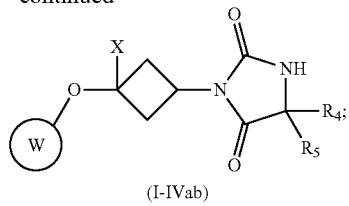

(I-IVab)

wherein groups W, X, $R^4$ and $R^5$ are as defined above, and wherein the compound of formula (IIab) and compound of formula (I-IVab) have the opposite relative stereochemistry.

Suitably this process comprises reacting a compound of formula syn-(IIab) with hydantoin (III) under Mitsunobu conditions to give a compound of formula anti-(I-IVab):

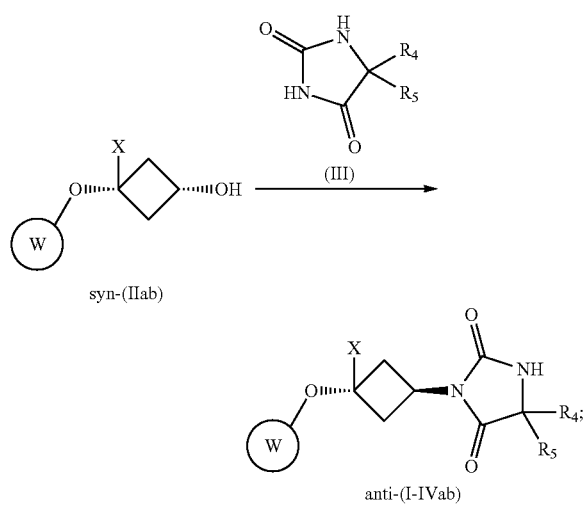

syn-(IIab)

(III)

anti-(I-IVab)

wherein groups W, X, $R^4$ and $R^5$ are as defined above.

In one embodiment is provided a process comprising reacting a compound of formula (II) with $R_{30}$-LG under suitable conditions to give a compound of formula (XXVI):

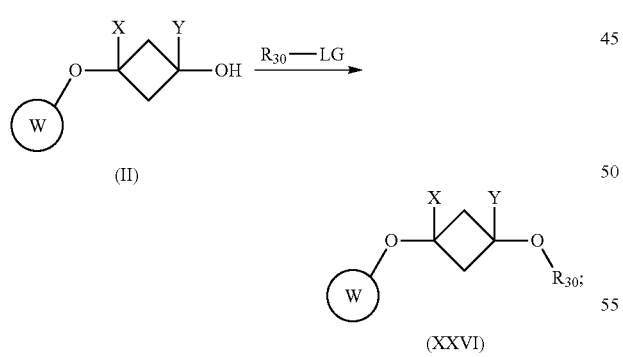

(II)

(XXVI)

wherein groups W, X and Y are as defined above, LG is a leaving group, $R_{30}$ is a suitable group which renders —$OR_{30}$ a leaving group and wherein the compound of formula (II) and compound of formula (XXVI) have the same relative stereochemistry.

In one embodiment is provided a process comprising reacting a compound of formula (XXVI) with hydantoin (III) under suitable conditions to give a compound of formula (I-IV):

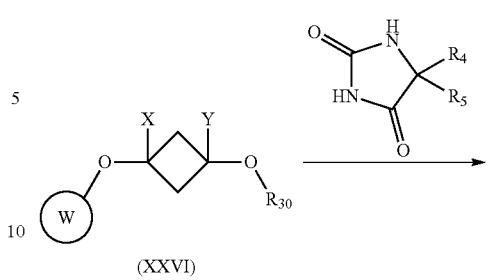

(XXVI)

(I-IV)

wherein groups W, X, Y, $R^4$ and $R^5$ are as defined above, —$OR_{30}$ is a leaving group, and wherein the compound of formula (XXVI) and compound of formula (I-IV) have the opposite relative stereochemistry.

In one embodiment is provided a process comprising reacting a compound of formula (IIab) under Mitsunobu conditions with phthalimide, to give a phthalidmide compound of formula (XIVab):

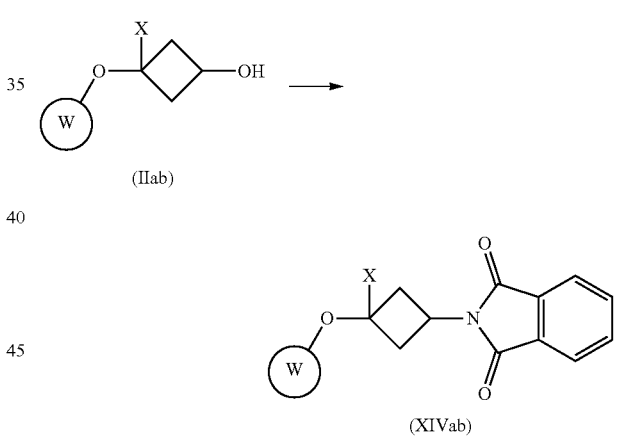

(IIab)

(XIVab)

wherein groups W and X are as defined above; and wherein the compound of formula (IIab), and compound of formula (XIVab) have the opposite relative stereochemistry.

Suitably this process comprises reacting a compound of general formula syn-(IIab) under Mitsunobu conditions with phthalimide, to give phthalimide compound of formula anti-(XIVab):

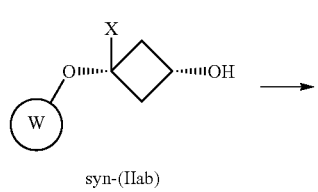

syn-(IIab)

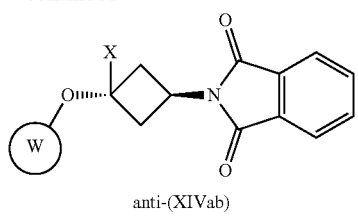

anti-(XIVab)

wherein groups W and X are as defined above.

In one embodiment is provided a process comprising reacting a compound of formula (XXVI) with phthalimide under suitable conditions to give a compound of formula (XIV):

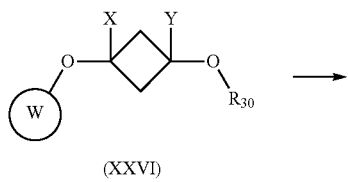

(XXVI)

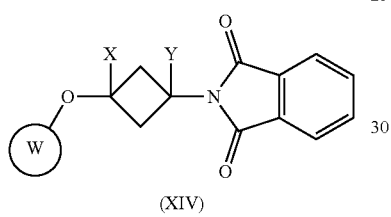

(XIV)

wherein groups W, X and Y are as defined above, and $OR_{30}$ is a leaving group, and wherein the compound of formula (XXVI) and compound of formula (XIV) have the opposite relative stereochemistry.

In one embodiment is provided a process comprising reacting a compound of formula (XIV) with hydrazine to give a compound of formula (XII):

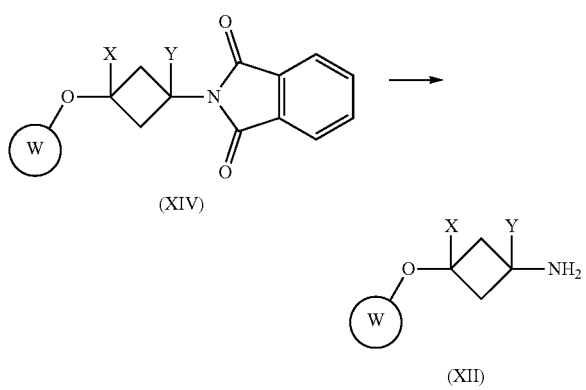

(XIV)

(XII)

wherein groups W, X and Y are as defined above; and wherein the compound of formula (XIV), and compound of formula (XII) have the same relative stereochemistry.

In one embodiment is provided a process comprising reacting a compound of formula (XII) with a compound of formula (XIII) to give a compound of formula (I-V):

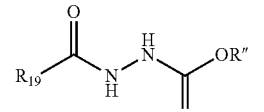

(XII)

(I-V)

wherein group W and $R^{19}$ are as defined above, and R" is $C_{1-4}$alkyl such as methyl or ethyl.

Suitably this process comprises reacting a compound of formula anti-(XII) with a compound of formula (XIII) to give a compound of formula anti-(I-V):

anti-(XII)

anti-(I-V)

wherein group W and $R^{19}$ are as defined above, and R" is $C_{1-4}$ alkyl such as methyl or ethyl.

Combinations of the above processes are also envisaged as embodiments of the invention.

In all of the above process embodiments, where two molecules/formulae are described as having the "opposite relative stereochemistry" this means that the relative stereochemistry is reversed during the reaction, such that if the starting material has syn-configuration then the reaction product will have anti-configuration, and conversely if the starting material has anti-configuration then the reaction product will have syn-configuration. Where the relative stereochemistry of the starting material and reaction product is not specified, then it should be assumed that the relative stereochemistry of the starting material is maintained in the reaction product.

In the above processes involving Mitsunobu reactions, the reaction is suitably carried out using a phosphine such as triphenylphosphine ($PPh_3$) or a derivative thereof (e.g. 4-(diphenylphosphino)benzoic acid) or trimethylphosphine (PMe₃); and an azodicarboxylate such as DEAD or DIAD, together with the appropriate nucleophile e.g. a phenol of formula (VI), a hydantoin of formula (III), a carboxylic acid of formula R'CO₂H or phthalimide. Where a carboxylic acid of formula R'CO₂H is used as nucleophile, R' is a substituted or unsubstituted alkyl, substituted or unsubstituted phenyl or substituted or unsubstituted benzyl group. Suitable carboxylic acids are well known to the skilled person. Suitably R' is phenyl and the acid is benzoic acid. The Mitsunobu reaction is suitably carried out in a solvent such as Et₂O, toluene, THF, acetonitrile, CH₂Cl₂ or mixtures thereof. Suitably the reaction is carried out in the temperature range of 0° C.-reflux. Where the Mitsunobu reaction is carried out using carboxylic acid R'CO₂H as nucleophile, the resulting ester is hydrolysed to give a hydroxyl group. The hydrolysis reaction proceeds with retention of configuration, while the Mitsunobu reaction leads to a reversal of configuration. Suitable bases for the hydrolysis include LiOH, NaOH or KOH. The hydrolysis is suitably carried out in a solvent such as MeOH, EtOH, THF, water, or a mixture thereof, suitably in the temperature range of 0° C.-reflux.

In the above processes, hydroxyl protecting group 'P' is used. Suitable hydroxyl protecting groups are well known to the skilled person (see Greene, 2006) and include benzyl, substituted benzyl (e.g. substituted by one or more C₁₋₄alkoxy such as OMe), methoxymethyl (MOM), tetrahydropyranyl (THP), C₁₋₄ alkyl (e.g. tert-butyl), C₂₋₄ alkene (e.g. allyl), silyl (e.g. tert-butyldimethylsilyl or tert-butyldiphenylsilyl), acyl (e.g. C(O)CH₃; or C(O)phenyl or C(O)benzyl (either of which may be substituted)) or the hydroxyl group forms an acetal group, which may be cyclic.

In the above processes, the hydroxyl group of a compound of formula (XV) can be reacted to form —OR₃₀ (XXIX) by reaction with R₃₀-LG, wherein LG is suitably halo such as Cl or Br. Suitably R₃₀ is SO₂R₃₁, wherein R₃₁ is C₁₋₄alkyl, C₁₋₄haloalkyl or phenyl optionally substituted with C₁₋₄alkyl. Suitably R₃₀-LG is mesyl chloride (CH₃SO₂Cl), tosyl chloride (4-toluenesulfonyl chloride, CH₃C₆H₄SO₂Cl) or trifluormethanesulfonyl chloride (ClSO₂CF₃). The group —OR₃₀, when reacted with a compound of formula (VI) under basic conditions (suitable bases include K₂CO₃, Cs₂CO₃, Na₂CO₃, NEt₃, DIPEA, DMAP or pyridine) is displaced, typically in an S$_N$2-type reaction, thereby reversing the stereochemistry of the starting compound.

Alternatively, a compound of formula (XV) could be reacted under suitable conditions to replace the unprotected hydroxyl group with a halogen such as Cl or Br, which can then be reacted with a compound of formula (VI).

The skilled person can select suitable deprotection conditions depending on the particular protecting group used. Where the protecting group is benzyl or substituted benzyl, suitable deprotection conditions include hydrogenolysis using H₂ in the presence of a catalyst e.g. Pd/C.

Such a hydrogenolysis reaction is suitably carried out in a solvent such as MeOH or EtOH, suitably in the temperature range of 0° C.-reflux. Where the protecting group is benzyl or substituted benzyl, transfer hydrogenation may be used as an alternative to using H₂, for example using ammonium formate in the presence of a catalyst such as Pd/C. Such a reaction is suitably carried out in a solvent such as MeOH or EtOH, suitably in the temperature range of 0° C.-reflux.

In the above processes where a triazolone is formed by reaction with a compound of formula (XIII), the reaction is suitably carried out in a solvent such as MeOH, or EtOH. However, any solvent or mixture of solvents in which the compounds of formula (XII) and (XIII) are soluble are potentially suitable. Suitably the reaction is carried out at reflux. An acid catalyst such as PTSA may optionally be added.

Intermediates of the Invention

The present invention also relates to novel intermediates in the synthesis of compounds of formula (I).

In one embodiment is provided a compound of formula (II):

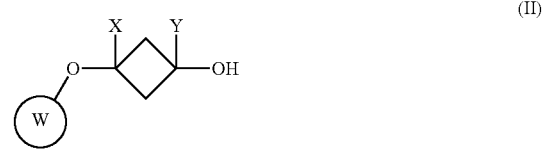

(II)

wherein:
X is H or CH₃;
Y is H or CH₃;
wherein at least one of X and Y is H;
W is group (Wa) or group (Wb):
wherein group (Wa) and group (Wb) are:

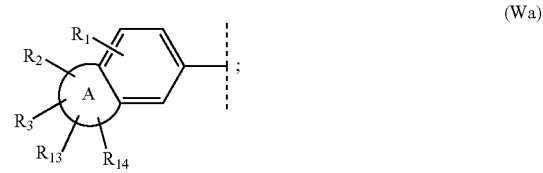

(Wa)

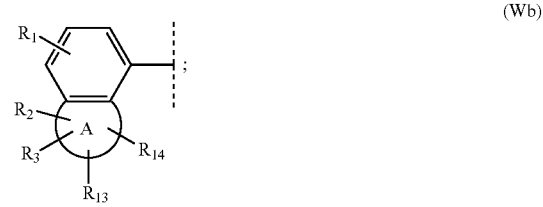

(Wb)

wherein:
R₁ is H, C₁₋₄alkyl, halo, haloC₁₋₄alkyl, CN, C₁₋₄alkoxy or haloC₁₋₄alkoxy;
R₂ is H, C₁₋₄alkyl, C₃₋₅ spiro carbocyclyl, haloC₁₋₄alkyl or halo;
R₃ is H, C₁₋₄alkyl, haloC₁₋₄alkyl, halo; or R₃ is absent;
R₁₃ is H, C₁₋₄alkyl, haloC₁₋₄alkyl, halo; or R₁₃ is absent;
R₁₄ is H, C₁₋₄alkyl, haloC₁₋₄alkyl, halo; or R₁₄ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
wherein R₂ and R₃ may be attached to the same or a different ring atom; R₂ may be attached to a fused ring atom; and wherein R₁₃ and R₁₄ may be attached to the same or a different ring atom;
or a salt and/or solvate thereof,
wherein the compound of formula (II) may have syn or anti configuration.

In one embodiment is provided a compound of formula (IIa):

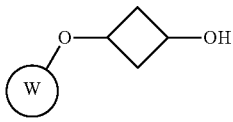

(IIa)

wherein:
W is group (Wa) or group (Wb):
wherein group (Wa) and group (Wb) are:

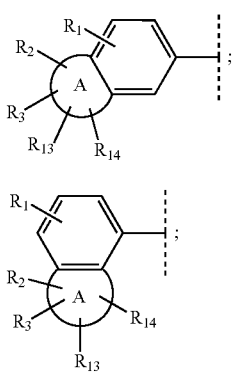

(Wa)

(Wb)

wherein:
R$_1$ is H, C$_{1-4}$alkyl, halo, haloC$_{1-4}$alkyl, CN, C$_{1-4}$alkoxy or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;
or a salt and/or solvate thereof,
wherein the compound of formula (IIa) may have syn or anti configuration.

In one embodiment is provided a compound of formula (II):

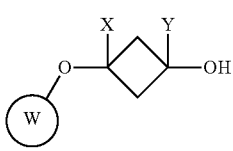

(II)

wherein:
X is H or CH$_3$;
Y is H or CH$_3$;
wherein at least one of X and Y is H;
W is group (Wc):
wherein group (Wc) is:

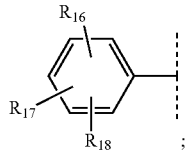

(Wc)

wherein:
R$_{16}$ is halo, C$_{1-4}$alkyl, C$_{1-4}$alkoxy, haloC$_{1-4}$alkyl, haloC$_{1-4}$alkoxy or CN;
R$_{17}$ is H, halo, CN, C$_{1-4}$alkyl, C$_{1-4}$alkoxy or haloC$_{1-4}$alkoxy;
R$_{18}$ is H, halo, CN, C$_{1-4}$alkyl or C$_{1-4}$alkoxy;
or a salt and/or solvate thereof,
wherein the compound of formula (II) may have syn or anti configuration.

In one embodiment is provided a compound of formula (II):

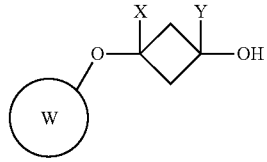

(II)

wherein:
X is H or CH$_3$;
Y is H or CH$_3$;
wherein at least one of X and Y is H;
W is group (Wc):

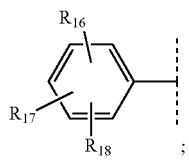

(Wc)

wherein:
R$_{16}$ is CN;
R$_{17}$ is H, halo, CN, C$_{1-4}$alkyl, C$_{1-4}$alkoxy or haloC$_{1-4}$alkoxy;
R$_{18}$ is H, halo, CN, C$_{1-4}$alkyl or C$_{1-4}$alkoxy;
or,
W is group (Wc-b):

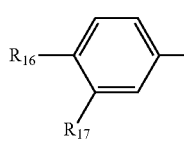

(Wc-b)

wherein:
R$_{16}$ is C$_{1-4}$alkyl; and
R$_{17}$ is C$_{1-4}$alkoxy or haloC$_{1-4}$alkoxy;
or a salt and/or solvate thereof,
wherein the compound of formula (II) may have syn or anti configuration.

In one embodiment is provided a compound of formula (IIa):

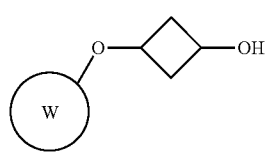
(IIa)

wherein:
W is group (Wc):

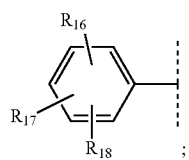
(Wc)

wherein:
R$_{16}$ is CN;
R$_{17}$ is H, halo, CN, C$_{1-4}$alkyl, C$_{1-4}$alkoxy or halo C$_{1-4}$alkoxy;
R$_{18}$ is H, halo, CN, C$_{1-4}$alkyl or C$_{1-4}$alkoxy;
or,
W is group (Wc-b):

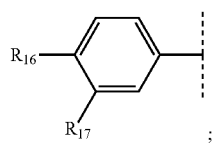
(Wc-b)

wherein:
R$_{16}$ is C$_{1-4}$alkyl; and
R$_{17}$ is C$_{1-4}$alkoxy or haloC$_{1-4}$alkoxy;
or a salt and/or solvate thereof,
wherein the compound of formula (IIa) may have syn or anti configuration.

In these embodiments, when W is group (Wc), suitably R$_{16}$ is at the para-position.

In one embodiment is provided a compound of formula (XII):

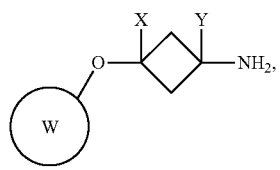
(XII)

wherein:
X is H or CH$_3$;
Y is H or CH$_3$;
wherein at least one of X and Y is H;
W is group (Wa) or group (Wb):
wherein group (Wa) and group (Wb) are:

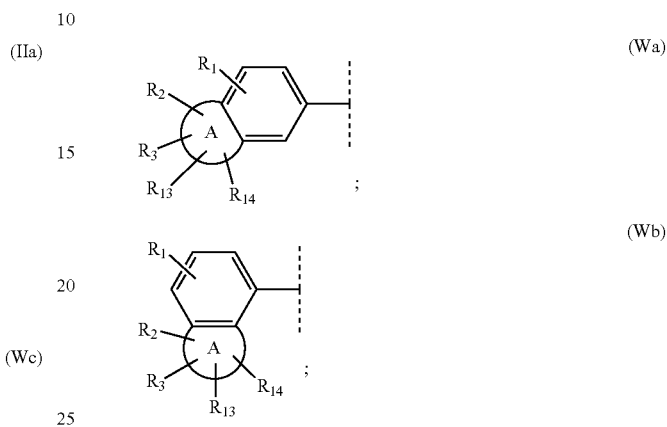
(Wa)

(Wb)

wherein:
R$_1$ is H, C$_{1-4}$alkyl, halo, haloC$_{1-4}$alkyl, CN, C$_{1-4}$alkoxy or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;
or a salt and/or solvate thereof,
wherein the compound of formula (XII) may have syn or anti configuration.

In one embodiment is provided a compound of formula (XIIa):

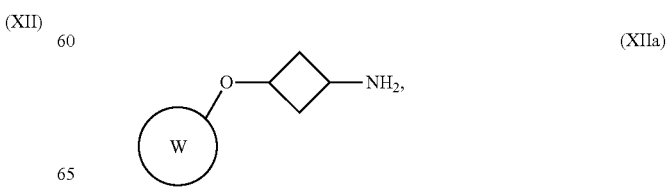
(XIIa)

wherein:
W is group (Wa) or group (Wb):
  wherein group (Wa) and group (Wb) are:

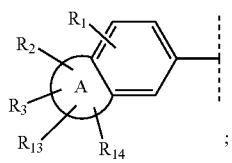
(Wa)

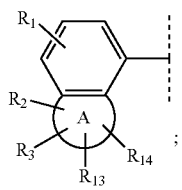
(Wb)

wherein:
  $R_1$ is H, $C_{1-4}$alkyl, halo, haloC$_{1-4}$alkyl, CN, $C_{1-4}$alkoxy or haloC$_{1-4}$alkoxy;
  $R_2$ is H, $C_{1-4}$alkyl, $C_{3-5}$ spiro carbocyclyl, haloC$_{1-4}$alkyl or halo;
  $R_3$ is H, $C_{1-4}$alkyl, haloC$_{1-4}$alkyl, halo; or $R_3$ is absent;
  $R_{13}$ is H, $C_{1-4}$alkyl, haloC$_{1-4}$alkyl, halo; or $R_{13}$ is absent;
  $R_{14}$ is H, $C_{1-4}$alkyl, haloC$_{1-4}$alkyl, halo; or $R_{14}$ is absent; A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
  wherein $R_2$ and $R_3$ may be attached to the same or a different ring atom; $R_2$ may be attached to a fused ring atom; and wherein $R_{13}$ and $R_{14}$ may be attached to the same or a different ring atom;
or a salt and/or solvate thereof,
wherein the compound of formula (XIIa) may have syn or anti configuration.

In one embodiment is provided a compound of formula (XII):

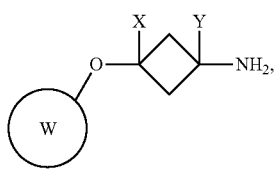
(XII)

wherein:
X is H or CH$_3$;
Y is H or CH$_3$;

wherein at least one of X and Y is H;
W is group (Wc-b):

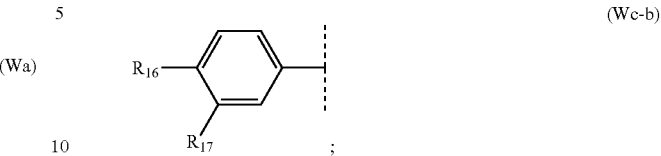
(Wc-b)

wherein:
  $R_{16}$ is CN or $C_{1-4}$alkyl; and
  $R_{17}$ is $C_{1-4}$alkoxy or haloC$_{1-4}$alkoxy;
or a salt and/or solvate thereof,
wherein the compound of formula (XII) may have syn or anti configuration.

In one embodiment is provided a compound of formula (XIIa):

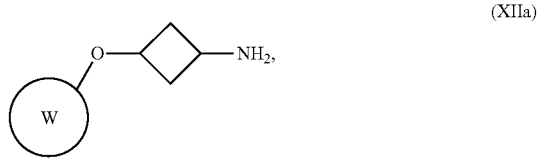
(XIIa)

wherein:
W is group (Wc-b):

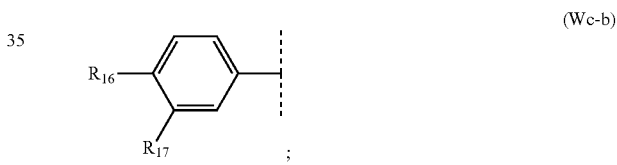
(Wc-b)

wherein:
  $R_{16}$ is CN or $C_{1-4}$alkyl; and
  $R_{17}$ is $C_{1-4}$alkoxy or haloC$_{1-4}$alkoxy;
or a salt and/or solvate thereof,
wherein the compound of formula (XIIa) may have syn or anti configuration.

In these embodiments, suitably the compound of formula (II) or formula (XII) has (Wb) as group W.

Particular intermediates of interest are:

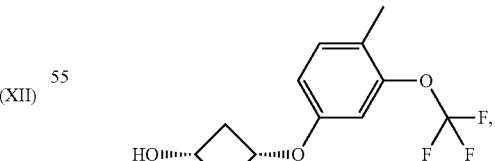

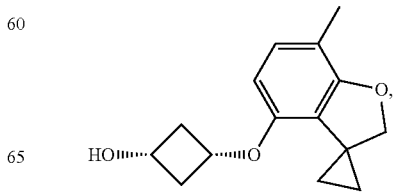

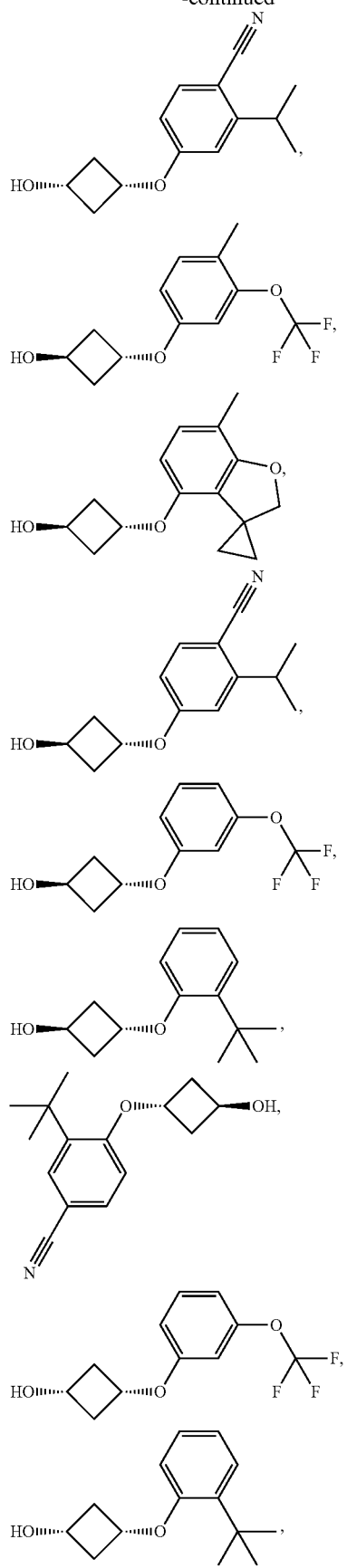
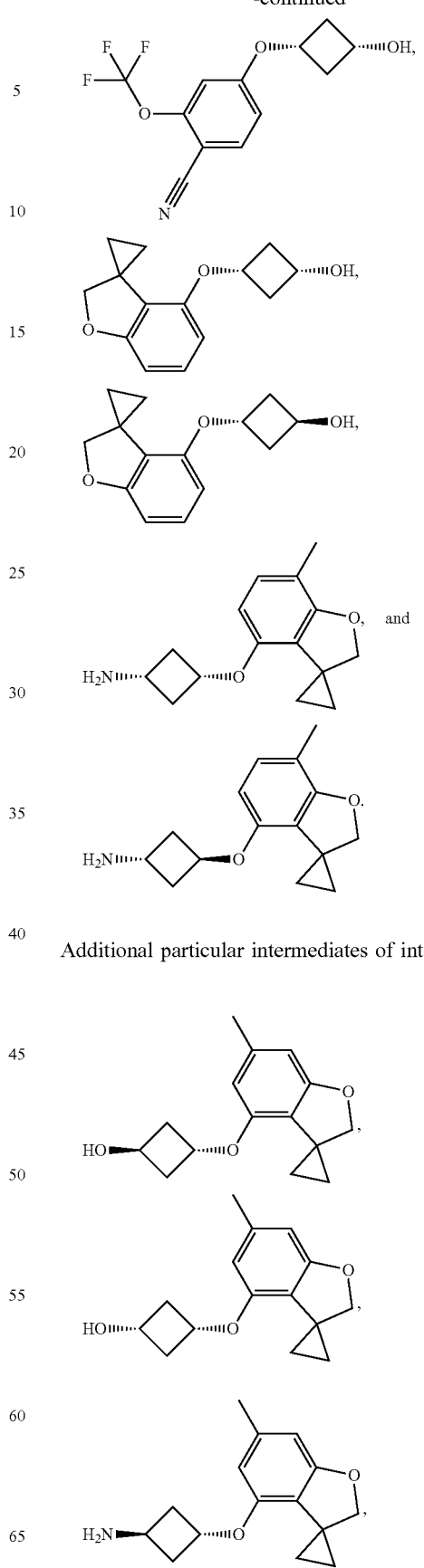
Additional particular intermediates of interest are:

Additional particular intermediates of interest are:
Additional particular intermediates of interest are:
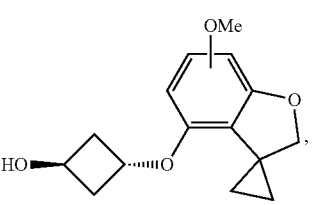

-continued

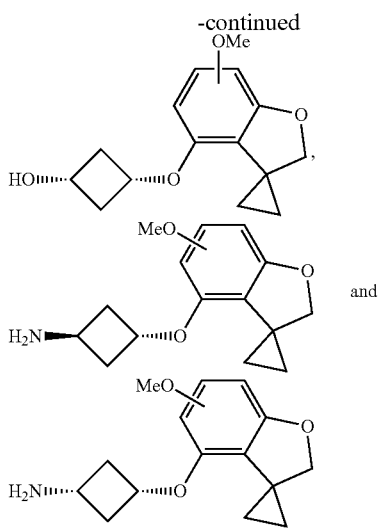

and wherein the substituent on the phenyl ring may be in the ortho, meta or para position relative to the —OCyclobutyl ring.

Kv3.1, Kv3.2 and/or Kv3.3 Modulation

Compounds of formula (I) of the present invention are modulators of Kv3.1. Compounds of formula (I) may also be modulators of Kv3.2 and/or Kv3.3. Compounds of the invention may be tested in the assay of Biological Example 1 to determine their modulatory properties for Kv3.1 and/or Kv3.2 and/or Kv3.3 channels.

A 'modulator' as used herein refers to a compound which is capable of producing at least 10% potentiation, and suitably at least 20% potentiation of whole-cell currents mediated by human Kv3.1 and/or human Kv3.2 and/or human Kv3.3 channels recombinantly expressed in mammalian cells.

The term 'Kv3.1, Kv3.2 and/or Kv3.3' shall be taken to mean the same as 'Kv3.1 and/or Kv3.2 and/or Kv3.3' and may also be referred to as 'Kv3.1/Kv3.2/Kv3.3'.

In one embodiment the modulator is capable of producing at least 10% potentiation and suitably at least 20% potentiation of whole-cell currents mediated by human Kv3.1 channels recombinantly expressed in mammalian cells. Suitably the $pEC_{50}$ of the modulator is in the range of 4-7 (such as 5-6.5).

In one embodiment the modulator is capable of producing at least 10% potentiation and suitably at least 20% potentiation of whole-cell currents mediated by human Kv3.2 channels recombinantly expressed in mammalian cells. Suitably the $pEC_{50}$ of the modulator is in the range of 4-7 (such as 5-6.5).

In one embodiment the modulator is capable of producing at least 10% potentiation and suitably at least 20% potentiation of whole-cell currents mediated by human Kv3.3 channels recombinantly expressed in mammalian cells. Suitably the $pEC_{50}$ of the modulator is in the range of 4-7 (such as 5-6.5).

In another embodiment the modulator is capable of producing at least 10% potentiation and suitably at least 20% potentiation of whole-cell currents mediated by human Kv3.1 and Kv3.2 channels recombinantly expressed in mammalian cells.

In another embodiment the modulator is capable of producing at least 10% potentiation and suitably at least 20% potentiation of whole-cell currents mediated by human Kv3.1 and Kv3.3 channels recombinantly expressed in mammalian cells.

In another embodiment the modulator is capable of producing at least 10% potentiation and suitably at least 20% potentiation of whole-cell currents mediated by human Kv3.2 and Kv3.3 channels recombinantly expressed in mammalian cells.

In a further embodiment the modulator is capable of producing at least 10% potentiation and suitably at least 20% potentiation of whole-cell currents mediated by human Kv3.1, Kv3.2 and Kv3.3 channels recombinantly expressed in mammalian cells.

The compounds of formula (I) or their pharmaceutically acceptable salts and/or solvates and/or derivatives may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv3.1 and Kv3.2 is a compound which alters the properties of these channels, either positively or negatively. In a particular aspect of the invention, the compound of formula (I) is a positive modulator. Compounds of the invention may be tested in the assay of Biological Example 1 to determine their modulatory properties.

In one embodiment of the invention the compounds of formula (I) or their pharmaceutically acceptable salts and/or solvates and/or derivatives thereof are selective for modulation of Kv3.1 channels over modulation of Kv3.2 channels. By selective, is meant that compounds demonstrate, for example, at least a 2 fold, 5 fold or 10 fold activity for Kv3.1 channels than for Kv3.2 channels. The activity of a compound is suitably quantified by its potency as indicated by an Ec50 value.

In another embodiment of the invention, the compounds of formula (I) or their pharmaceutically acceptable salts and/or solvates and/or derivatives thereof are selective for modulation of Kv3.2 channels over modulation of Kv3.1 channels. Once again, by selective is meant that compounds demonstrate, for example at least a 2 fold, 5 fold or 10 fold activity for Kv3.2 channels than for Kv3.1 channels.

In a particular embodiment of the invention the compounds of formula (I) or their pharmaceutically acceptable salts and/or solvates and/or derivatives thereof demonstrate comparable activity between modulation of Kv3.1 and Kv3.2 channels, for example the activity for one channel is less than 2 fold that for the other channel, such as less than 1.5 fold or less than 1.2 fold.

In certain disorders it may be of benefit to utilise a modulator of Kv3.3 or Kv3.1, or Kv3.3 and Kv3.1 which demonstrates a particular selectivity profile between the two channels. For example a compound may be selective for modulation of Kv3.3 channels over modulation of Kv3.1 channels demonstrating, for example, at least a 2 fold, 5 fold or 10 fold activity for Kv3.3 channels than for Kv3.1 channels.

In another embodiment of the invention, the compounds of formula (I) or their pharmaceutically acceptable salts and/or solvates and/or derivatives thereof are selective for modulation of Kv3.1 channels over modulation of Kv3.3 channels. Once again, by selective is meant that compounds demonstrate, for example at least a 2 fold, 5 fold or 10 fold activity for Kv3.1 channels than for Kv3.3 channels.

In a particular embodiment of the invention, a compound may demonstrate comparable activity between modulation of Kv3.3 and Kv3.1 channels, for example the activity for each channel is less than 2 fold that for the other channel, such as less than 1.5 fold or less than 1.2 fold.

In certain disorders it may be of benefit to utilise a modulator of Kv3.3 or Kv3.2, or Kv3.3 and Kv3.2 which demonstrates a particular selectivity profile between the two channels. A compound may be selective for modulation of Kv3.3 channels over modulation of Kv3.2 channels demonstrating, for example, at least a 2 fold, 5 fold or 10 fold activity for Kv3.3 channels than for Kv3.2 channels.

In another embodiment of the invention, the compounds of formula (I) or their pharmaceutically acceptable salts and/or solvates and/or derivatives thereof are selective for modulation of Kv3.2 channels over modulation of Kv3.3 channels. Once again, by selective is meant that compounds demonstrate, for example at least a 2 fold, 5 fold or 10 fold activity for Kv3.2 channels than for Kv3.3 channels.

In another particular embodiment a compound may demonstrate comparable activity between modulation of Kv3.3 and Kv3.2 channels, for example the activity for each channel is less than 2 fold that for the other channel, such as less than 1.5 fold or less than 1.2 fold.

In a yet further particular embodiment of the invention a compound may demonstrate comparable activity between modulation of Kv3.3, Kv3.2 and Kv3.1 channels, for example the activity for each channel is less than 2 fold that for any other channel, such as less than 1.5 fold or less than 1.2 fold. The activity of a compound is suitably quantified by its potency as indicated by an EC50 value.

Therapeutic Methods

The invention also provides a compound of formula (I), or a pharmaceutically acceptable salt and/or solvate (e.g. salt) and/or derivative thereof, for use in the treatment or prophylaxis of a disease or disorder where a modulator of Kv3.1, Kv3.2 and/or Kv3.3 is required, for example those diseases and disorders mentioned herein below.

The invention provides a method of treating or preventing a disease or disorder where a modulator of Kv3.1, Kv3.2 and/or Kv3.3 is required, for example those diseases and disorders mentioned herein below, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the treatment or prophylaxis of a disease or disorder where a modulator of Kv3.1, Kv3.2 and/or Kv3.3 is required, for example those diseases and disorders mentioned herein below.

In one embodiment is provided a compound of formula (I) or a pharmaceutically acceptable salt and/or solvate thereof and/or derivative thereof for use as a medicament.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

Diseases or disorders that may be mediated by modulation of Kv3.1 and/or Kv3.2 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

In one embodiment of the invention, the compounds of formula (I) or their pharmaceutically acceptable salts and/or solvates and/or derivatives may be of use for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Ménière's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In one embodiment of the invention, the compounds of formula (I) or their pharmaceutically acceptable salts and/or solvates and/or derivatives may be of use for the treatment or prophylaxis of a disease or disorder selected from the group consisting of hearing disorders including hearing loss and tinnitus, schizophrenia, substance abuse disorders, pain such as neuropathic pain, inflammatory pain and miscellaneous pain, Lewy body dementia and Parkinson's disease.

In one embodiment of the invention, the compounds of formula (I) or their pharmaceutically acceptable salts and/or solvates and/or derivatives may be of use for the treatment or prophylaxis of a disease or disorder selected from the group consisting of Fragile-X, Rett's Disorder and Alzheimer's disease.

The invention provides a method for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Meniere's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative thereof, in the manufacture of a medicament for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Meniere's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In a particular embodiment of the invention, there is provided a compound of formula (I) or their pharmaceutically acceptable salts and/or solvates (e.g. salts) and/or derivatives thereof for use in the treatment of prophylaxis of hearing disorders. Hearing disorders include auditory neuropathy, auditory processing disorder, hearing loss, which includes sudden hearing loss, noise induced hearing loss, substance-induced hearing loss, and hearing loss in adults over 60, over 65, over 70 or over 75 years of age (presbycusis), and tinnitus.

The compounds of formula (I) or their pharmaceutically acceptable salts and/or solvates (e.g. salts) and/or derivatives thereof may be of use for the treatment or prophylaxis of Meniere's disease, disorders of balance, and disorders of the inner ear.

In a particular embodiment of the invention, there is provided a compound of formula (I) or their pharmaceutically acceptable salts and/or solvates (e.g. salts) and/or derivatives thereof for use in the treatment or prophylaxis of schizophrenia. Schizophrenia includes the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts and/or solvates (e.g. salts) and/or derivatives thereof may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90); Seasonal affective disorder.

The compounds of formula (I) or their pharmaceutically acceptable salts and/or solvates (e.g. salts) and/or derivatives thereof may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomolies associated with seizures or epilepsy such as Partial monosomy (15Q)/Angelman syndrome).

The compounds of formula (I) or their pharmaceutically acceptable salts and/or solvates (e.g. salts) and/or derivatives thereof may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); *Cannabis*-Related Disorders such as *Cannabis* Dependence (304.30), *Cannabis* Abuse (305.20), *Cannabis* Intoxication (292.89), *Cannabis* Intoxication Delirium, *Cannabis*-Induced Psychotic Disorder, *Cannabis*-Induced Anxiety Disorder and *Cannabis*-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks)

(292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) or their pharmaceutically acceptable salts and/or solvates (e.g. salts) and/or derivatives thereof may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

The compounds of formula (I) or their pharmaceutically acceptable salts and/or solvates (e.g. salts) and/or derivatives thereof may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The compounds of formula (I) or their pharmaceutically acceptable salts and/or solvates (e.g. salts) and/or derivatives thereof may be of use for the treatment or prophylaxis of hyperacusis and disturbances of loudness perception, including Fragile-X syndrome and autism.

The compounds of formula (I) or their pharmaceutically acceptable salts and/or solvates (e.g. salts) and/or derivatives thereof may be of use for the treatment or prophylaxis of Impulse control disorder including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts and/or solvates (e.g. salts) and/or derivatives thereof may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts and/or solvates (e.g. salts) and/or derivatives thereof may be of use for the treatment or prophylaxis of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts and/or solvates (e.g. salts) and/or derivatives thereof may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) or their pharmaceutically acceptable salts and/or solvates (e.g. salts) and/or derivatives thereof may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts and/or solvates (e.g. salts) and/or derivatives thereof may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

The compounds of formula (I) or their pharmaceutically acceptable salts and/or solvates (e.g. salts) and/or derivatives thereof may be of use for the enhancement of cognition including the treatment of cognition impairment in other diseases such as schizophrenia, bipolar disorder, depression, other psychiatric disorders and psychotic conditions associated with cognitive impairment, e.g. Alzheimer's disease. Alternatively, the compounds of formula (I) or their pharmaceutically acceptable salts and/or solvates thereof may be of use for the prophylaxis of cognition impairment, such as may be associated with in diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts and/or solvates (e.g. salts) and/or derivatives thereof may be of use for the treatment or prophylaxis of ataxia including ataxia, in particular spinocerebellar ataxia, especially ataxia associated with R420H, R423H or F448L mutations.

The compounds of formula (I) or their pharmaceutically acceptable salts and/or solvates (e.g. salts) and/or derivatives thereof may be of use for the treatment or prophylaxis of pain including nociceptive, neuropathic, inflammatory or miscellaneous pain.

Nociceptive pain represents the normal response to noxious insult or injury of tissues such as skin, muscles, visceral organs, joints, tendons, or bones. Examples of nociceptive pain which form part of the invention include somatic pain: musculoskeletal (joint pain, myofascial pain) or cutaneous, which is often well localized; or visceral pain: hollow organs or smooth muscle.

Neuropathic pain is pain initiated or caused by a primary lesion or disease in the somatosensory nervous system. Sensory abnormalities range from deficits perceived as paraesthesia (numbness) to hypersensitivity (hyperalgesia or allodynia), and dysaesthesia (tingling and other sensations). Examples of neuropathic pain which form part of the invention include, but are not limited to, diabetic neuropathy, post-herpetic neuralgia, spinal cord injury pain, phantom limb (post-amputation) pain, and post-stroke central pain. Other causes of neuropathic pain include trauma, chemotherapy and heavy metal exposure.

Inflammatory pain occurs as a result of activation and sensitization of the nociceptive pain pathway by a variety of mediators released at a site of tissue inflammation. Mediators that have been implicated as key players in inflammatory pain are pro-inflammatory cytokines such IL-1-alpha, IL-1-beta, IL-6 and TNF-alpha, chemokines, reactive oxygen species, vasoactive amines, lipids, ATP, acid, and other factors released by infiltrating leukocytes, vascular endothelial cells, or tissue resident mast cells. Examples causes of inflammatory pain which form part of the invention include appendicitis, rheumatoid arthritis, inflammatory bowel disease, and herpes zoster.

Miscellaneous pain refers to pain conditions or disorders which are not easily classifiable. The current understanding of their underlying mechanisms is still rudimentary though specific therapies for those disorders are well known; they include cancer pain, migraine and other primary headaches and wide-spread pain of the fibromyalgia type.

Suitably, specific pain indications that may be mediated by a modulator of Kv3.1 and/or Kv3.2 and/or Kv3.3 channels are neuropathic pain and/or inflammatory pain.

Pain is a subjective condition and in a clinical setting tends to be measured by a patient's self-assessment. Therefore it can be difficult to measure and quantify pain threshold. For chronic pain, typically a subjective 11-point rating scale is used where 0 is no pain and 10 is the worst pain imaginable. Subjects generally record their worst pain over a given period, usually a day. A minimum mean baseline score is also recorded and response to the medication is measured relative to the baseline, for example, a reduction of at least 10%, 20%, 30%, 40% or 50% in pain from the baseline score may be observed.

Since individual responses to medicaments may vary, not all individuals may experience a reduction in pain from the baseline score. Consequently, suitably a reduction is observed in at least at least 10%, 20%, 30%, 40%, 50%, 60%, 70%, 80%, 90% or all individuals tested.

Therefore, in one embodiment of the invention, a reduction of at least 10%, 20%, 30%, 40% or 50% in pain from the baseline score is observed upon administration of a Kv3.1/Kv3.2/Kv3.3 modulator, such as a compound of formula (I) or a pharmaceutically acceptable salt, solvate and/or derivative thereof to a subject in need thereof.

Administration of a Kv3.1/Kv3.2/Kv3.3 modulator can occur before an anticipated onset of pain or after the onset of pain. In cases where it is anticipated that development of a disease or disorder may lead to an increase in pain experienced by the subject, a Kv3.1/Kv3.2/Kv3.3 modulator, such as a compound of formula (I) or a pharmaceutically acceptable salt, solvate and/or derivative thereof can be administered. In cases where a subject is already experiencing pain, a Kv3.1/Kv3.2/Kv3.3 modulator, such as a compound of formula (I) or a pharmaceutically acceptable salt, solvate and/or derivative thereof may be administered to a subject in need thereof.

Treatment of the subject in need thereof may continue for as long as treatment is required, for example, 1 day, 1 week, 2 weeks, 3 weeks, 1 month, 6 months, 1 year, more than 1 year more than 2 years, more than 5 years or more than 10 years. Therefore in one embodiment of the invention, a therapeutically effective amount of a Kv3.1/Kv3.2/Kv3.3 modulator, such as a compound of formula (I) or a pharmaceutically acceptable salt, solvate and/or derivative thereof, is administered to a subject in need thereof for 1 day to 1 month, 1 week to 3 months, 1 month to 6 months, 3 months to 1 year or more than 1 year.

Reduction in pain in a subject can be measured by assessing the response to an external stimuli such as mechanical or thermal (e.g. cold) stimuli (such as described in the Experimental section). The reduction can either be considered as a percentage reversal (calculated by measuring the pre- and post-dose thresholds of the affected pain site with a non-affected pain site, such as described in more detail under Data Analysis in the Experimental Section) or by measuring withdrawal thresholds of the affected pain site. Preferably, the percentage reversal calculation is used.

Therefore, in one embodiment of the invention, the sensitivity to pain (such as neuropathic pain or inflammatory pain) is reversed by more than 20%, more than 30%, more than 40%, more than 50%, more than 60%, more than 70%, more than 80% or more than 90%, upon administration of a therapeutically effective amount of a Kv3.1/Kv3.2/Kv3.3 modulator, such as a compound of formula (I) or a pharmaceutically acceptable salt, solvate and/or derivative thereof. Suitably, the sensitivity to pain is reversed by more than 80% or more than 90%.

Subjects receiving the Kv3.1/Kv3.2/Kv3.3 modulator may experience secondary benefits, such as one or more of improved function, mood, sleep, quality of life, reduced time off work.

In a particular embodiment, the compounds of formula (I) or their pharmaceutically acceptable salts and/or solvates (e.g. salts) and/or derivatives thereof may be of use for the treatment or prophylaxis of neuropathic pain.

In a particular embodiment, the compounds of formula (I) or their pharmaceutically acceptable salts and/or solvates (e.g. salts) and/or derivatives thereof may be of use for the treatment or prophylaxis of inflammatory pain.

In a particular embodiment, the compounds of formula (I) or their pharmaceutically acceptable salts and/or solvates (e.g. salts) and/or derivatives thereof may be of use for the treatment or prophylaxis of miscellaneous pain.

In one embodiment is provided a compound of formula (I) for use in the prophylaxis of acute noise-induced hearing loss.

In one embodiment is provided a method for the prophylaxis of acute noise-induced hearing loss, comprising administering to a subject in need thereof a compound of formula (I).

In one embodiment is provided the use of a compound of formula (I) in the manufacture of a medicament for the prophylaxis of acute noise-induced hearing loss.

Acute noise-induced hearing loss may be caused by events such as exposure to loud noise or a blast. In these cases, where it is anticipated that a future event may result in acute noise-induced hearing loss, the compound of formula (I) or a pharmaceutically acceptable salt, solvate and/or derivative thereof may be administered before the event in order to prevent or reduce acute noise-induced hearing loss.

The administration of compound (I) or a pharmaceutically acceptable salt, solvate and/or derivative thereof may prevent any acute noise-induced hearing loss, or may reduce the severity of the acute noise-induced hearing loss or may mitigate other symptoms arising from acute noise-induced hearing loss, such as tinnitus. "Acute hearing loss" is defined as hearing loss which occurs rapidly over a period of hours or days. For example, hearing loss may occur over a period of minutes, hours or days (for example over a period of up to 1 day, such as up to 2 days, 3 days, 4 days, 5 days, 6 days or 7 days). Acute hearing loss will typically be caused by exposure to loud sound or blast. Hearing loss caused by exposure to loud sound or blast is referred to herein as "noise-induced induced hearing loss". "Acute noise induced hearing loss" is therefore hearing loss which occurs rapidly over a period of hours or days caused by exposure to loud sound or blast.

Important symptoms of acute hearing loss include:
1. a shift in the auditory threshold, i.e. an increase in the minimum sound level of a pure tone that can be heard with no other sound present;
2. tinnitus; and
3. degradation in central auditory processing, for example impaired auditory temporal processing and/or speech understanding.

A "loud" noise or blast may be at least 90 dB, for example, at least 100 dB, at least 110 dB, at least 120 dB or at least 130 dB.

In one embodiment, administration of the compound of formula (I) or a pharmaceutically acceptable salt, solvate and/or derivative thereof is initiated before an event which is anticipated to cause noise-induced acute hearing loss. For example, administration of the compound of formula (I) or a pharmaceutically acceptable salt, solvate and/or derivative thereof may be initiated up to 2 weeks in advance, such as up to 1 week, 6 days, 5 days, 4 days, 3 days, 2 days, 24 h, 12 h, 6 h, 5 h, 4 h, 3 h, 2 h, 1 h, 30 minutes or up to 15 minutes in advance of an event which is anticipated to cause noise-induced acute hearing loss. The compound of formula (I) or a pharmaceutically acceptable salt, solvate and/or derivative thereof may be administered on multiple occasions before event which is anticipated to cause noise-induced acute hearing loss.

In one embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of permanent tinnitus; for preventing or reducing the development of a permanent shift in auditory thresholds; or for preventing or reducing the development of permanently degraded central auditory processing, including for example auditory temporal processing and/or speech understanding.

It will be appreciated that administration in advance may be in circumstances where the subject is considered to be at risk of exposure to a noise or blast which is anticipated to cause acute noise-induced hearing loss and is not limited to those circumstances where such exposure ultimately occurs.

In one embodiment, administration of the compound of formula (I) or a pharmaceutically acceptable salt, solvate and/or derivative thereof is initiated during an event which is anticipated to cause noise-induced acute hearing loss. The compound of formula (I) or a pharmaceutically acceptable salt, solvate and/or derivative thereof may be administered on multiple occasions during an event which is anticipated to cause noise-induced acute hearing loss.

In one embodiment, a compound of formula (I) or a pharmaceutically acceptable salt, solvate and/or derivative thereof is initially administered during a noise or blast which is anticipated to cause acute noise-induced hearing loss, for preventing or reducing the development of permanent tinnitus; for preventing or reducing the development of a permanent shift in the auditory threshold; or for preventing or reducing the development of permanently degraded central auditory processing, including for example auditory temporal processing and/or speech understanding.

In one embodiment, administration of the compound of formula (I) or a pharmaceutically acceptable salt, solvate and/or derivative thereof is initiated after an event which is anticipated to cause acute noise-induced hearing loss.

Thus, in one embodiment, a compound of formula (I) or a pharmaceutically acceptable salt, solvate and/or derivative thereof is initially administered after a noise or blast which is anticipated to cause acute noise-induced hearing loss, for preventing or reducing the development of permanent tinnitus; for preventing or reducing the development of a permanent shift in the auditory threshold; or for preventing or reducing the development of permanently degraded central auditory processing, including for example auditory temporal processing and/or speech understanding.

When the compound of formula (I) is administered after an event which is anticipated to cause acute noise-induced hearing loss, such administration is normally undertaken during the "acute phase" i.e. before the hearing loss has become established.

In one embodiment, administration of the compound of formula (I) or a pharmaceutically acceptable salt, solvate and/or derivative thereof may be initiated up to 2 months after an event which is anticipated to cause noise-induced acute hearing loss, such as up to 1 month, 2 weeks, 1 week, 6 days, 5 days, 4 days, 3 days, 2 days, 24 h, 12 h, 6 h, 5 h, 4 h, 3 h, 2 h, 1 h, 30 minutes or up to 15 minutes after an event which is anticipated to cause acute noise-induced hearing loss. The compound of formula (I) or a pharmaceutically acceptable salt, solvate and/or derivative thereof may be administered on multiple occasions after an event which is anticipated to cause noise-induced acute hearing loss.

The compound of formula (I) or a pharmaceutically acceptable salt, solvate and/or derivative thereof may be administered over a period of up to 7 days (for example, up to 1 day, up to 2 days, up to 3 days, up to 4 days, up to 5 days, up to 6 days or up to 7 days), for 1-2 weeks (for example, 7-8 days, 7-9 days, 7-10 days, 7-11 days, 7-12 days, 7-13 days or 7-14 days), for 2-4 weeks (for example, 2-3 weeks or 2-4 weeks) or for 1-2 months (for example, 4-6 weeks or 4-8 weeks).

The compound of formula (I) or a pharmaceutically acceptable salt, solvate and/or derivative thereof may initially be administered up to 1 day in advance, such as up to 2 days in advance, up to 3 days in advance, up to 5 days in advance, up to 1 week in advance, up to 2 weeks in advance or up to 1 month in advance of a noise or blast which is anticipated to cause acute noise-induced hearing loss, administration which is initiated at any point in advance exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

In one embodiment is provided a compound of formula (I) or a pharmaceutically acceptable salt, solvate and/or derivative thereof for use in preventing or reducing the development of a permanent shift in the auditory threshold, wherein the permanent shift in auditory threshold is reduced by at least 10 dB, such as at least 15 dB, at least 20 dB, at least 30 dB, at least 40 dB, or completely.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) and/or derivative thereof, and a pharmaceutically acceptable carrier or excipient.

In one embodiment, there is provided a pharmaceutical composition comprising a compound of formula (I), or a pharmaceutically acceptable salt and/or solvate (e.g. salt) and/or derivative thereof, for use in the treatment or prevention of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Meniere's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease. In a further embodiment, there is provided a method for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Meniere's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease, which comprises administering to a subject in need thereof an effective amount of a pharmaceutical composition comprising a compound of formula (I) or a pharmaceutically acceptable salt and/or solvate (e.g. salt) and/or derivative thereof.

The invention also provides the use of a pharmaceutical composition comprising a compound of formula (I), or a pharmaceutically acceptable salt and/or solvate thereof (e.g. salt) and/or derivative thereof, in the manufacture of a medicament for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Meniere's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

The compounds of formula (I) or their pharmaceutically acceptable salts and/or solvates and/or derivatives thereof may be administered by any convenient method, e.g. by oral, parenteral, buccal, sublingual, nasal, rectal or transdermal administration, and the pharmaceutical compositions adapted accordingly. Other possible routes of administration include intratympanic and intracochlear.

The compounds of formula (I) or their pharmaceutically acceptable salts and/or solvates and/or derivatives thereof which are active when given orally can be formulated as liquids or solids, e.g. as syrups, suspensions, emulsions, tablets, capsules or lozenges.

A liquid formulation will generally consist of a suspension or solution of the active ingredient (such as a compound of formula (I) or a pharmaceutically acceptable salt and/or solvate (e.g. salt) and/or derivative thereof) in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient (such as a compound of formula (I) or a pharmaceutically acceptable salt and/or solvate (e.g. salt) and/or derivative thereof) can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient (such as a compound of formula (I) or a pharmaceutically acceptable salt and/or solvate (e.g. salt) and/or derivative thereof) in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluoro-chloro-hydro-carbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. In one embodiment the composition is in unit dose form such as a tablet, capsule or ampoule. The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 mg to 1000 mg, more suitably 1.0 mg to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further pharmaceutically acceptable active ingredient or ingredients.

The invention provides a compound of formula (I), for use in combination with a further pharmaceutically acceptable active ingredient or ingredients.

When the compounds are used in combination with other therapeutic agents, the compounds may be administered either sequentially or simultaneously by any convenient route. Alternatively, the compounds may be administered separately.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

EXPERIMENTAL

The invention is illustrated by the compounds described below. The following examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. This invention is meant to include such equivalents.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities, ranging from for example 85% to 99%. Calculations of number of moles and yield are in some cases adjusted for this.

HPLC-Mass spectra (HPLC-MS) were taken on an Agilent 1100 Series LC/MSD Mass Spectrometer coupled with HPLC instrument Agilent 1100 Series, operating in positive electrospray ionization mode and in acidic gradient conditions.

Quality Control (8 Minutes Method):
LC/MS-ES+ under acidic conditions was performed on a Phenomenex Luna C18 column (3 μm 2×50 mm). Mobile phase: A: ($H_2O$+0.05% TFA by vol.)/B: ($CH_3CN$+0.05% TFA by vol). Gradient: t=0 min 0% (B). From 0 to 95% (B) in 8 min. 95% (B) for 0.5 min. From 95 to 100% (B) in 0.5 min. 100% (B) for 0.5 min. From 100% to 0% (B) in 0.1 min. Stop time 11 min. Column T=40° C. Flow rate: 1.0 ml/min. Mass range ES+: (100-1000 amu, F=60). UV detection wavelengths: DAD 1A=220.8, DAD 1B=254.8. The use of this methodology is indicated by "LC/MS: QC_8_MIN" in the analytic characterization of the described compounds.

Quality Control (3 Minutes Method):
LC/MS-ES+ under acidic conditions was performed on a Zorbax SB C18 column (1.8 μm 3×50 mm). Mobile phase: A: ($H_2O$+0.05% TFA by vol.)/B: ($CH_3CN$+0.05% TFA by vol). Gradient: t=0 min 0% (B), from 0 to 95% (B) in 2.5 min, 95% (B) for 0.2 min, from 95 to 100% (B) in 0.2 min, 100% (B) for 0.4 min, from 100% to 0% (B) in 0.1 min. Stop time 4 min. Column T=60° C. Flow rate: 1.5 ml/min. Mass range ES+: (100-1000 amu, F=60). UV detection wavelengths: DAD 1A=220.8, DAD 1B=254.8. The use of this methodology is indicated by "LC/MS: QC_3_MIN" in the analytic characterization of the described compounds.

Proton Magnetic Resonance (NMR) spectra were recorded either on Varian instruments at 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 60° C.

2D NMR NOESY experiments were acquired with a mixing time of 500 ms using a spectral width of 3355 Hz in both f1 and f2. A total of 256 increments were collected, processed to 1 K with linear prediction, 8 scans each. Data were processed with sine bell shift in both dimensions and with lb=0.3 Hz in f1.

Direct infusion Mass spectra (MS) were run on an Agilent 1100 Series LC/MSD Mass Spectrometer, operating in ES (+) and ES (−) ionization mode [ES (+): Mass range: 100-1000 amu. Infusion solvent: water+0.1% $HCO_2H$/$CH_3CN$ 50/50. ES (−): Mass range: 100-1000 amu. Infusion solvent: water+0.05% $NH_4OH$/$CH_3CN$ 50/50]. The use of this methodology is indicated by "MS_1 (ESI)" in the analytic characterization of the described compounds.

HPLC-Mass spectra (HPLC-MS) were taken on an Agilent 1100 Series LC/MSD Mass Spectrometer coupled with HPLC instrument Agilent 1100 Series, operating in positive electrospray ionization mode and in acidic gradient conditions.

In a number of preparations, purification was performed using manual flash chromatography, semi-automatic flash chromatography (Biotage Flash Master Personal) or automatic flash chromatography (Biotage SP1 and SP4).

Flash chromatographies on silica gel were carried out on pre-packed Biotage silica cartridges (e.g. Biotage SNAP cartridge KP-Sil). Reverse phase C18 Flash Chromatographies were carried out using VARIAN MEGA BE-C18 cartridges, or pre-packed Biotage C18 cartridges (e.g. Biotage SNAP cartridge KP-C18-HS).

Abbreviations cHex cyclohexane
DCM dichloromethane
DEAD diethyl azodicarboxylate
DIPEA N,N-diisopropylethylamine
DIAD diisopropyl azodicarboxylate
DMAP 4-dimethylaminopyridine
DMF N,N-dimethylformamide
DMSO dimethylsulfoxide
DMSO-$d_6$ deutrated dimethylsulfoxide
EGTA (ethylene glycol-bis(β-aminoethyl ether)-N,N,N',N'-tetraacetic acid)
$Et_2O$ diethyl ether
EtOAc ethyl acetate
EtOH ethanol
h hours
$H_2$ gaseous hydrogen
HBTU O-(benzotriazol-1-yl)-N,N,N',N'-tetramethyluronium tetrafluoroborate
HCl hydrochloric acid
HEPES 4-(2-hydroxyethyl)-1-piperazineethanesulfonic acid
HMDS hexamethyldisilazane
KOH potassium hydroxide
LiOH lithium hydroxide
MeOH methanol
MTBE tert-butyl methyl ether
NaCl sodium chloride
$NaHCO_3$ sodium hydrogen carbonate
$Na_2SO_4$ sodium sulfate
NMR nuclear magnetic resonance
NaOH sodium hydroxide
Pd/C palladium on charcoal
PTSA p-toluenesulfonic acid
r.t. room temperature
ss saturated solution
TBS-Cl tert-butyldimethylsilyl chloride
TBTU O-(benzotriazol-1-yl)-N,N,N',N'-tetramethyluronium tetrafluoroborate
TEA triethylamine
TFA trifluoroacetic acid
THF tetrahydrofuran Compound Examples Intermediate 1: syn-3-benzyloxycyclobutanol

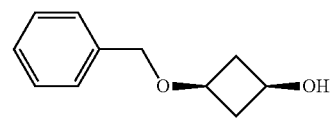

$NaBH_4$ (1.29 g, 34 mmol, 1.2 eq) was added portionwise at 0° C. to a stirred solution of commercially available 3-benzyloxycyclobutanone (5 g, 28.4 mmol) in MeOH (50 mL). The reaction was stirred at 0° C. for 40 minutes, then $NH_4Cl$ aq (ss) was added. EtOAc was added and phases separated. The organic phase was washed with brine, dried over Na$_2$SO$_4$, filtered and concentrated. The crude was purified by flash chromatography (Biotage system) on silica gel using a SNAP 100 g as column and cHex/EtOAc as eluent from 8:2 to 4:6 affording 3.79 g of the title compound as colourless oil. HPLC 3 min: Rt=1.99 min, [M+H+]=196 (−17)

Intermediate 2: anti-(3-benzyloxycyclobutyl) benzoate

In a flask containing syn-3-benzyloxycyclobutanol (100 mg, 0.561 mmol, Intermediate 1) solubilized in THF (10 mL), benzoic acid (103 mg, 0.842 mmol), triphenylphosphine (221 mg, 0.84 mmol) and DIAD (122 μl, 0.62 mmol) were added. The reaction was stirred at r.t. overnight. Further triphenyl phosphine (221 mg, 0.84 mmol) and DIAD (122 μl, 0.62 mmol) were added and the reaction was stirred at 50° C. for 3 h. Volatiles were evaporated under reduced pressure and the residue purified by flash chromatography (Biotage system) on silica gel using a SNAP 2×10 g as columns and cHex/EtOAC from 100:0 to 80:20 as eluent, affording the title compound (155 mg). HPLC-MS 3 minutes, Rt=2.715, MS=300 [M+18].

Intermediate 3: anti-3-benzyloxycyclobutanol

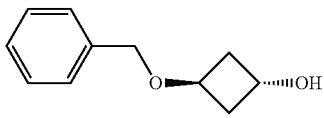 [SMILES: O[C@H]1C[C@H](OCc2ccccc2)C1]

Anti-(3-benzyloxycyclobutyl) benzoate (155 mg, 0.549 mmol, Intermediate 2) was solubilized in MeOH (3 mL) and THF (3 mL). Then a 1 M solution of NaOH (corresponding to 1.10 mmol) was added and the reaction was stirred at 45° C. for 1 h. The mixture was concentrated to dryness and the residue was taken up in MTBE (30 mL) and washed with water (3×5 mL). The organic layer was separated and dried over Na$_2$SO$_4$ before concentration to dryness. The crude was purified by flash chromatography (Biotage system) on silica gel using a SNAP 25 g as column and cHex/EtOAc from 95:5 to 20:80 as eluent, affording the title compound (90 mg). HPLC-MS 3 minutes, RT=1.846, MS=196 [M+18].

Intermediate 4: anti-4-(3-benzyloxycyclobutoxy)-1-methyl-2-(trifluoromethoxy)benzene

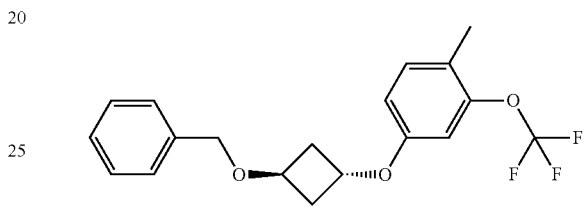

DIAD (600 uL, 3.08 mmol) was added to a stirred solution of syn-3-benzyloxycyclobutanol (500 mg, 2.8 mmol, Intermediate 1), 4-methyl-3-(trifluoromethoxy)phenol (710 mg, 3.37 mmol), triphenylphosphine (880 mg, 3.37 mmol) in THF (30 mL). The reaction mixture was stirred overnight at r.t., then 4-methyl-3-(trifluoromethoxy)phenol (1 mmol), triphenylphosphine (1 mmol) and DIAD (0.92 mmol) were added. The reaction mixture was stirred at r.t. for 5 h, then concentrated. The crude was purified by flash chromatography (Biotage system) on silica gel using a SNAP 100 g as column and cHex/EtOAc as eluent from 10:0 to 7:3 affording 830 mg of the title compound as yellow oil. HPLC 3 min: Rt=2.91 min, [M+H+]=339

The following intermediates have been prepared by using the same foregoing methodology replacing 4-methyl-3-(trifluoromethoxy)phenol with the appropriate phenol:

| Int | Structure | Phenol | LC-MS |
| --- | --- | --- | --- |
| 5 | 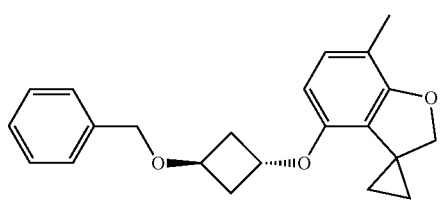<br>anti-4-(3-benzyloxycyclobutoxy)-7-methyl-spiro[2H-benzofuran-3,1'-cyclopropane] | 7-methylspiro[2H-benzofuran-3,1'-cyclopropane]-4-ol | 3 min<br>RT: 3.12 min<br>[M + H$^+$]: 337 |

| Int | Structure | Phenol | LC-MS |
|---|---|---|---|
| 6 | anti-4-(3-benzyloxycyclobutoxy)-2-isopropyl-benzonitrile | 4-hydroxy-2-isopropyl-benzonitrile | 3 min RT: 2.9 min [M + H$^+$]: 332 |
| 7 | anti-1-(3-benzyloxycyclobutoxy)-3-(trifluoromethoxy)benzene | 3-(trifluoromethoxy) phenol | 3 min RT: 2.94, [M + H$^+$]: 339 |
| 8 | anti-1-(3-benzyloxycyclobutoxy)-2-tert-butyl-benzene | 2-tert-butylphenol | 3 min RT: 3.10, [M + H$^+$]: 311 |

The following compounds have been obtained using the same methodology described for Intermediate 4 replacing syn-3-benzyloxycyclobutanol (Intermediate 1) with anti-3-benzyloxycyclobutanol (Intermediate 3) and 4-methyl-3-(trifluoromethoxy)phenol with the appropriate phenol.

| Int | Structure | Phenol | LC-MS |
|---|---|---|---|
| 9 | syn-1-(3-benzyloxycyclobutoxy)-3-(trifluoromethoxy)benzene | 3-(trifluoromethoxy) phenol | 3 min RT: 2.90, [M + H$^+$]: 339 |
| 10 | syn-1-(3-benzyloxycyclobutoxy)-2-tert-butyl-benzene | 2-tert-butylphenol | 3 min RT: 3.07, [M + H$^+$]: 311 |

Intermediate 11: anti-3-[4-methyl-3-(trifluoromethoxy)phenoxy]cyclobutanol

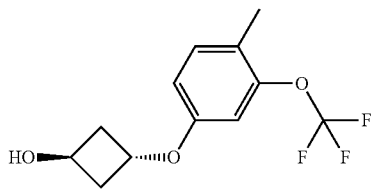 [SMILES: Cc1ccc(O[C@H]2C[C@H](O)C2)cc1OC(F)(F)F]

Ammonium formate (2976 mg, 47.2 mmol) was added portionwise (4 portions) in 4 h to a stirred solution of anti-4-(3-benzyloxycyclobutoxy)-1-methyl-2-(trifluoromethoxy)benzene (830 mg, 2.45 mmol, Intermediate 4) and Pd/C (10% w/w, 250 mg) in MeOH (60 mL). The reaction mixture was refluxed for a total of 6 h, then filtered through a pad of cellulose microcrystalline and washed with EtOAc. Solvent was evaporated, then water and EtOAc were added. Phases were separated and the organic phase dried over sodium sulfate, filtered and concentrated. The crude was purified by flash chromatography (Biotage system) on silica gel using a SNAP 50 g as column and cHex/EtOAc as eluent from 8:2 to 1:1 affording 400 mg of the title compound as colourless oil. HPLC 3 min: Rt=2.4 min, [M+H+]=263.

The following intermediates have been prepared by using the same foregoing methodology replacing 4-(3-benzyloxycyclobutoxy)-1-methyl-2-(trifluoromethoxy)benzene (intermediate 4) with the appropriate benzyloxy intermediate:

| Int | Structure | Benzyloxy Int. | LC-MS |
|---|---|---|---|
| 12 | anti-3-(7-methylspiro[2H-benzofuran-3,1'-cyclopropane]-4-yl)oxycyclobutanol | anti-4-(3-benzyloxycyclobutoxy)-7-methyl-spiro[2H-benzofuran-3,1'-cyclopropane], Intermediate 5 | 3 min RT: 2.4 min [M + H+]: 247 |
| 13 | anti-4-(3-hydroxycyclobutoxy)-2-isopropyl-benzonitrile | anti-4-(3-benzyloxycyclobutoxy)-2-isopropyl-benzonitrile, Intermediate 6 | 3 min RT: 2.21 min [M + H+]: 232 |
| 14 | anti-3-[3-(trifluoromethoxy)phenoxy]cyclobutanol | anti-1-(3-benzyloxycyclobutoxy)-3-(trifluoromethoxy)benzene, Intermediate 7 | 3 min RT: 2.32 min [M + H+]: 249 |
| 15 | anti-3-(2-tert-butylphenoxy)cyclobutanol | anti-1-(3-benzyloxycyclobutoxy)-2-tert-butyl-benzene, Intermediate 8 | 3 min RT: 2.53 min [M − H2O]: 203 |

| Int | Structure | Benzyloxy Int. | LC-MS |
|---|---|---|---|
| 16 | syn-3-[3-(trifluoromethoxy)phenoxy]cyclobutanol | syn-1-(3-benzyloxycyclobutoxy)-3-(trifluoromethoxy)benzene, Intermediate 9 | 3 min RT: 2.32 min [M + H⁺]: 249 |
| 17 | syn-3-(2-tert-butylphenoxy)cyclobutanol | Syn-1-(3-benzyloxycyclobutoxy)-2-tert-butyl-benzene, Intermediate 10 | 3 min RT: 2.53 min [M − H2O]: 203 |

Intermediate 18: syn-[3-[4-methyl-3-(trifluoromethoxy)phenoxy]cyclobutyl]benzoate

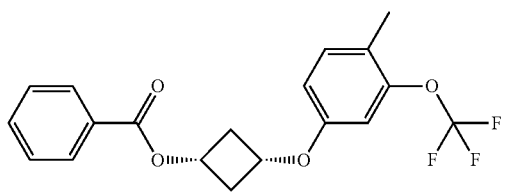 [SMILES: Cc1ccc(O[C@H]2C[C@@H](OC(=O)c3ccccc3)C2)cc1OC(F)(F)F]

DIAD (165 µl, 0.83 mmol) was added to a mixture of anti-3-[4-methyl-3-(trifluoromethoxy)phenoxy]cyclobutanol (200 mg, 0.76 mmol, Intermediate 11), triphenyl phosphine (300 mg, 1.14 mmol) and benzoic acid (140 mg, 1.14 mmol) in THF (10 mL). The reaction mixture was stirred at r.t. for 2 h, then concentrated. The crude was purified by flash chromatography (Biotage system) on silica gel using a SNAP 50 g as column and cHex/EtOAc as eluent from 8:2 to 1:1 affording the title compound (260 mg) as yellow oil. HPLC 3 min: Rt=3.019 min, [M+H+]=367.

The following intermediates have been prepared by using the same foregoing methodology replacing anti-3-[4-methyl-3-(trifluoromethoxy)phenoxy]cyclobutanol (Intermediate 11) with the appropriate alcohol:

| Int | Structure | Alcohol Intermediate | LC-MS |
|---|---|---|---|
| 19 | syn-[3-(7-methylspiro[2H-benzofuran-3,1'-cyclopropane]-4-yl)oxycyclobutyl]benzoate | anti-3-(7-methylspiro[2H-benzofuran-3,1'-cyclopropane]-4-yl)oxycyclobutanol, Intermediate 12 | 3 min RT: 2.98 min [M + H⁺]: 351 |
| 20 | syn-[3-(4-cyano-3-isopropyl-phenoxy)cyclobutyl]benzoate | anti-4-(3-hydroxycyclobutoxy)-2-isopropyl-benzonitrile, Intermediate 13 | 3 min RT: 2.86 min [M + H⁺]: 336 |

Intermediate 21: syn-3-[4-methyl-3-(trifluoromethoxy)phenoxy]cyclobutanol

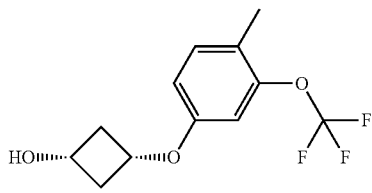 [SMILES: Cc1ccc(O[C@H]2C[C@@H](O)C2)cc1OC(F)(F)F]

A solution of NaOH 2M (57 mg, 1.42 mmol) was added to a solution of syn-[3-[4-methyl-3-(trifluoromethoxy)phenoxy]cyclobutyl] benzoate (260 mg, 0.71 mmol, Intermediate 18) in MeOH (2.5 mL) and THF (2.5 mL). The reaction mixture was stirred at 45° C. for 2 h, then water and MTBE were added. Phases were separated and the organic phase dried over $Na_2SO_4$, filtered and concentrated. The crude was purified by flash chromatography (Biotage system) on silica gel using a SNAP 25 g as column and cHex/EtOAc as eluent from 9:1 to 4:6 affording the title compound (135 mg, 0.51 mmol) as a white solid. HPLC 3 min: Rt=2.38 min, [M+H+]=263.

The following intermediates have been prepared by using the same foregoing methodology replacing syn-[3-[4-methyl-3-(trifluoromethoxy)phenoxy]cyclobutyl] benzoate (intermediate 18) with the appropriate ester intermediate:

Intermediate 24: syn-(3-benzyloxycyclobutoxy)-tert-butyl-dimethyl-silane

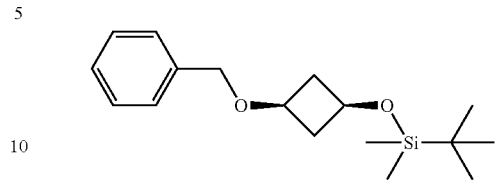

To a solution of syn-3-benzyloxycyclobutanol (150 mg, 0.8416 mmol, Intermediate 1) in DCM (3 mL), imidazole (85.9 mg, 1.26 mmol) was added. Then the reaction was cooled to 0° C. and TBS-Cl was added. The reaction mixture was stirred at room temperature for 4 h, then an aqueous saturated solution of $NH_4Cl$ (10 mL) and DCM (15 mL) were added. The organic layer was dried over $Na_2SO_4$, filtered and concentrated under reduced pressure. The crude was purified by flash chromatography (Biotage system) on silica gel using a SNAP 25 g as column and cHex/EtOAc from 100:0 to 70:30 as eluent, affording the title compound (229 mg) as a colourless oil. HPLC 3 min RT: 3.03 min [M+H+]: 293.

The following intermediate has been prepared by using the same foregoing methodology replacing syn-3-benzyloxycyclobutanol (Intermediate 1) with anti-3-benzyloxycyclobutanol (Intermediate 3):

| Int | Structure | Ester intermediate | LC-MS |
|---|---|---|---|
| 22 | syn-3-(7-methylspiro[2H-benzofuran-3,1'-cyclopropane]-4-yl)oxycyclobutanol | syn-[3-(7-methylspiro[2H-benzofuran-3,1'-cyclopropane]-4-yl)oxycyclobutyl] benzoate, Intermediate 19 | 3 min RT: 2.18 min [M + H+]: 246 |
| 23 | syn-4-(3-hydroxycyclobutoxy)-2-isopropyl-benzonitrile | syn-[3-(4-cyano-3-isopropyl-phenoxy)cyclobutyl] benzoate, Intermediate 20 | 3 min RT: 2.18 min [M + H+]: 232 |

| Int | Structure | LC-MS |
|---|---|---|
| 25 | anti-(3-benzyloxycyclobutoxy)-tert-butyl-dimethyl-silane | 3 min<br>RT: 3.12 min<br>[M + H⁺]: 293 |

Intermediate 26: syn-3-[tert-butyl(dimethyl)silyl]oxycyclobutanol

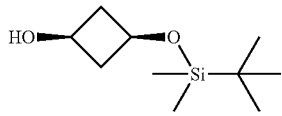

To a solution of syn-(3-benzyloxycyclobutoxy)-tert-butyl-dimethyl-silane (225 mg, 0.77 mmol, Intermediate 24) in EtOH (20 mL), palladium (16 mg, 0.15 mmol) and ammonium formate (477 mg, 7.7 mmol) were added. The suspension was stirred at reflux for 5 h and at r.t. overnight. Then, further palladium (16 mg, 0.15 mmol) and ammonia formate (477 mg, 7.7 mmol) were added and the reaction heated at 80° C. for 7 h and at r.t. for the weekend. The suspension was filtered through cellulose microcrystalline and concentrated under reduced pressure. The crude was purified by flash chromatography (Biotage system) on silica gel using a SNAP 25 g as column and cHex/EtOAc from 99:1 to 50:50 as eluent, affording the title compound syn-3-[tert-butyl(dimethyl)silyl]oxycyclobutanol (88 mg) as a colourless oil. HPLC 3 min RT: 2.35 min [M+H⁺]: 203.

The following intermediate has been prepared by using the same foregoing methodology replacing syn-(3-benzyloxycyclobutoxy)-tert-butyl-dimethyl-silane (Intermediate 24) with anti-(3-benzyloxycyclobutoxy)-tert-butyl-dimethyl-silane (Intermediate 25):

| Int | Structure | LC-MS |
|---|---|---|
| 27 | anti-3-[tert-butyl(dimethyl)silyl]oxycyclobutanol | 3 min<br>RT: 2.37 min<br>[M + H⁺]: 203 |

Intermediate 28: anti-3-tert-butyl-4-[3-[tert-butyl(dimethyl)silyl]oxycyclobutoxy] benzonitrile

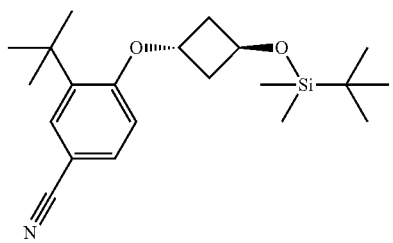 [SMILES: CC(C)(C)c1cc(C#N)ccc1O[C@H]1C[C@@H](O[Si](C)(C)C(C)(C)C)C1]

To a solution of syn-3-[tert-butyl(dimethyl)silyl]oxycyclobutanol (85 mg, 0.42 mmol, Intermediate 26) in THF (5 mL), 3-tert-butyl-4-hydroxy-benzonitrile (88 mg, 0.50 mmol), triphenyl phosphine (165 mg, 0.63 mmol) and DIAD (102 mg, 0.50 mmol) were added. The reaction was stirred at r.t. overnight. Then the solvent was evaporated under reduced pressure and the crude was purified by flash chromatography (Biotage system) on silica gel using a SNAP 50 g as column and cHex/EtOAc from 99:1 to 80:20 as eluent, affording the title compound (131 mg) as a pale yellow solid. HPLC 3 min RT: 3.32 min [M+H⁺]: 360.

The following intermediate has been prepared by using the same foregoing methodology replacing syn-3-[tert-butyl(dimethyl)silyl]oxycyclobutanol (intermediate 26) with anti-3-[tert-butyl(dimethyl)silyl]oxycyclobutanol (Intermediate 27):

| Int | Structure | LC-MS |
|---|---|---|
| 29 | syn-3-tert-butyl-4-[3-[tert-butyl(dimethyl)silyl]oxycyclobutoxy]benzonitrile | 3 min<br>RT: 3.27 min<br>[M + H⁺]: 360 |

Intermediate 30: anti-4-[3-[tert-butyl(dimethyl)silyl]oxycyclobutoxy]-2-(trifluoromethoxy)benzonitrile

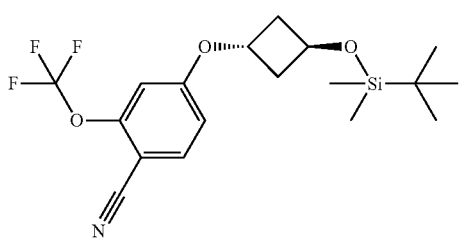 [SMILES: CC(C)(C)[Si](C)(C)O[C@H]1C[C@H](Oc2ccc(C#N)c(OC(F)(F)F)c2)C1]

4-hydroxy-2-(trifluoromethoxy)benzonitrile (80 mg, 0.39 mmol) was dissolved in THF (8 mL), then syn-3-[tert-butyl(dimethyl)silyl]oxycyclobutanol (88 mg, 0.43 mmol, Intermediate 26), triphenyl phosphine (124 mg, 0.47 mmol) and DIAD (88 mg, 0.43 mmol) were added. The reaction mixture was stirred overnight at r.t., then concentrated. The crude was purified by flash chromatography (Biotage system) using two SNAP 10 g as column and cHex/EtOAc (from 10:0 to 1:1) affording the title compound (162 mg) as a yellow oil. HPLC 3 min RT: 3.10 min.

The following intermediate has been prepared by using the same foregoing methodology replacing syn-3-[tert-butyl (dimethyl)silyl]oxycyclobutanol (Intermediate 26) with anti-3-[tert-butyl(dimethyl)silyl]oxycyclobutanol (Intermediate 27):

| Int | Structure | LC-MS |
|---|---|---|
| 31 | syn-4-[3-[tert-butyl(dimethyl)silyl]oxycyclobutoxy]-2-(trifluoromethoxy)benzonitrile | 3 min RT: 3.10 min [M + H⁺]: 388 |

Intermediate 32: syn-tert-butyl-dimethyl-(3-spiro [2H-benzofuran-3,1'-cyclopropane]-5-yloxycyclobutoxy)silane

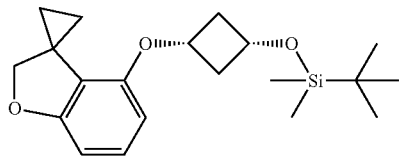 [SMILES: CC(C)(C)[Si](C)(C)O[C@H]1C[C@@H](Oc2cccc3c2C2(CC2)CO3)C1]

To a 0° C. solution of anti-3-[tert-butyl(dimethyl)silyl] oxycyclobutanol (100 mg, 0.4941 mmol, Intermediate 27) and TEA (100 mg, 0.99 mmol) in DCM (5 mL), methanesulfonyl chloride (113 mg, 0.99 mmol) was added dropwise. The reaction was stirred at 0° C. for 30 minutes, then water (10 mL) and DCM (10 mL) were added. The phases were separated and water was re-extracted with fresh DCM (2×10 mL). The organic layers were dried over Na$_2$SO$_4$ and evaporated under reduced pressure to give the mesylate intermediate which was used in the next step without further purification.

85 mg of the mesylate intermediate were added to a stirred suspension of spiro[2H-benzofuran-3,1'-cyclopropane]-4-ol (44 mg, 0.27 mmol) and cesium carbonate (197 mg, 0.60 mmol) in DMF (5 mL) and the reaction mixture was stirred at 100° C. overnight. The reaction was quenched with water (10 mL) and extracted with EtOAc (3×15 mL), the organic layers were dried over Na$_2$SO$_4$ and evaporated under reduced pressure. The crude was purified by flash chromatography (Biotage system) on silica gel using a SNAP 50 g as column and cHex/EtOAc from 99:1 to 70:30 as solvent, affording the title compound (40 mg) as a white solid. HPLC 3 minutes, RT=3.18, MS=347 [M+1].

The following intermediate has been prepared by using the same foregoing methodology replacing anti-3-[tert-butyl (dimethyl)silyl]oxycyclobutanol (Intermediate 27) with syn-3-[tert-butyl(dimethyl)silyl]oxycyclobutanol (Intermediate 26):

| Int | Structure | LC-MS |
|---|---|---|
| 33 | anti-tert-butyl-dimethyl-(3-spiro[2H-benzofuran-3,1'-cyclopropane]-5-yloxycyclobutoxy)silane | 3 min RT: 3.20 min [M + H⁺]: 347 |

Intermediate 34: anti-3-tert-butyl-4-(3-hydroxycyclobutoxy)benzonitrile

To a solution of anti-3-tert-butyl-4-[3-[tert-butyl(dimethyl)silyl]oxycyclobutoxy]benzonitrile (130 mg, 0.36 mmol, Intermediate 28) in THF (5 mL), tetrabutylammonium fluoride (113 mg, 0.43 mmol) was added and the reaction was stirred at r.t. for 30 minutes. Then a saturated aqueous solution of NH$_4$Cl (15 mL) and EtOAc (15 mL) were added. Phases were separated and the aqueous layer was re-extracted with fresh ethyl acetate (2×15 mL). The organics were collected together and dried over Na$_2$SO$_4$, filtered and concentrated under reduced pressure. The crude was purified by flash chromatography (Biotage system) on silica gel using a SNAP 25 g as column and cHex/EtOAc from 90:10 to 20:80 as eluent, affording the title compound (79 mg) as a white solid. HPLC 3 min RT: 2.34 min [M+H⁺]: 246.

The following intermediates have been prepared by using the same foregoing methodology replacing anti-3-tert-butyl-4-[3-[tert-butyl(dimethyl)silyl]oxycyclobutoxy]benzonitrile (Intermediate 28) with the appropriate silylated compound:

| Int | Structure | Sililated compound | LC-MS |
|---|---|---|---|
| 35 | syn-3-tert-butyl-4-(3-hydroxycyclobutoxy)benzonitrile | syn-3-tert-butyl-4-[3-[tert-butyl(dimethyl)silyl]oxycyclobutoxy]benzonitrile Intermediate 29 | 3 min RT: 2.31 min [M + H$^+$]: 246 |
| 36 | Anti-4-(3-hydroxycyclobutoxy)-2-(trifluoromethoxy)benzonitrile | Anti-4-[3-[tert-butyl(dimethyl)silyl]oxycyclobutoxy]-2-(trifluoromethoxy)benzonitrile, Intermediate 30 | 3 min RT: 2.17 min [M + H$^+$]: 274 |
| 37 | syn-4-(3-hydroxycyclobutoxy)-2-(trifluoromethoxy)benzonitrile | syn-4-[3-[tert-butyl(dimethyl)silyl]oxycyclobutoxy]-2-(trifluoromethoxy)benzonitrile, Intermediate 31 | 3 min RT: 2.13 min [M + H$^+$]: 274 |
| 38 | syn-3-spiro[2H-benzofuran-3,1'-cyclopropane]-4-yloxycyclobutanol | syn-tert-butyl-dimethyl-(3-spiro[2H-benzofuran-3,1'-cyclopropane]-4-yloxycyclobutoxy)silane Intermediate 32 | 3 min RT: 2.12 min [M + H$^+$]: 233 |
| 39 | anti-3-spiro[2H-benzofuran-3,1'-cyclopropane]-4-yloxycyclobutanol | anti-tert-butyl-dimethyl-(3-spiro[2H-benzofuran-3,1'-cyclopropane]-4-yloxycyclobutoxy)silane Intermediate 33 | 3 min RT: 2.13 min [M + H$^+$]: 233 |

Intermediate 40: tert-butyl N-[(1S)-1-carbamoylpropyl]carbamate

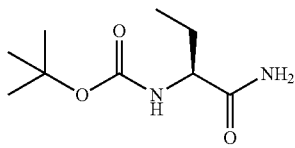

A solution of (S)-2-((tert-butoxycarbonyl)amino)butanoic acid (4.92 mmol, 1000 mg), DIPEA (12.30 mmol, 2.14 mL) and HBTU (6.40 mmol, 2054 mg) in DCM/DMF (7 mL/3 mL) was stirred for 10 minutes, then HMDS (5.41 mmol, 1.13 mL) was added and the reaction was stirred at r.t. for 1 h. The mixture was concentrated under reduced pressure, the residue was taken up in EtOAc (50 mL), washed with HCl 1M (5 mL) and then with a saturated aqueous solution of NaHCO$_3$ (5 mL). The organic layer was dried over Na$_2$SO$_4$ and concentrated to dryness under reduced pressure. The crude was purified by flash chromatography (Biotage system) on silica gel using a SNAP 50 g as column and cHex/EtOAc from 80:20 to 0:100 as eluent, affording the title compound (820 mg, 83%, Intermediate 16) as a white solid. HPLC-MS 3 minutes, R$_T$=1.69, MS=147 [M−55].

Intermediate 41: tert-butyl N-[(1R)-1-carbamoylpropyl]carbamate

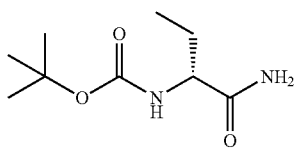

The title compound has been prepared by using the same foregoing methodology replacing (S)-2-((tert-butoxycarbonyl)amino)butanoic acid with (R)-2-((tert-butoxycarbonyl)amino)butanoic acid. HPLC-MS 3 minutes, RT=1.70, MS=147 [M−55].

Intermediate 42: (2S)-2-aminobutanamide-2,2,2-trifluoroacetate

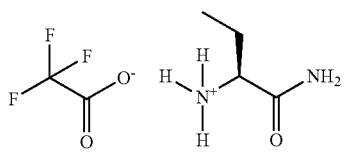

To a solution of tert-butyl N-[(1S)-1-carbamoylpropyl]carbamate (4.05 mmol, 820 mg, Intermediate 40) in DCM (12 mL) was added TFA (4 mL). The reaction was stirred at r.t. for 1 h, then was concentrated under reduced pressure. The oily crude was precipitated in diisopropyl ether to obtain the title compound (660 mg, 76%, Intermediate 17) as a white solid. HPLC-MS 3 minutes, RT=0.24, MS=103 [M+1].

Intermediate 43: (2R)-2-aminobutanamide 2,2,2-trifluoroacetate

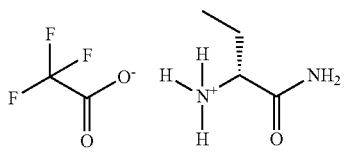

The title compound has been prepared by using the same foregoing methodology replacing tert-butyl N-[(1S)-1-carbamoylpropyl]carbamate (Intermediate 40) with tert-butyl N-[(1R)-1-carbamoylpropyl]carbamate (Intermediate 41). HPLC-MS 3 minutes, RT=0.23, MS=103 [M+1].

Intermediate 44: (5S)-5-ethylimidazolidine-2,4-dione

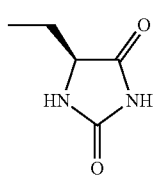

To a solution of triphosgene (3.97 mmol, 1177 mg) in DCM (20 mL), at 0° C., a solution (2S)-2-aminobutanamide 2,2,2-trifluoroacetate (3.05 mmol, 660 mg, Intermediate 42) and DIPEA (15.3 mmol, 2.66 mL) in DCM (20 mL) was added dropwise. The reaction was left to rise to r.t. and stirred overnight. Then DCM (20 mL) was added and the organic layer was washed with three portions of HCl 2M (3×2 mL), dried over Na$_2$SO$_4$ and concentrated to dryness under reduced pressure. The crude was purified by flash chromatography (Biotage system) on silica gel using a SNAP 50 g as column and CH$_2$Cl$_2$/MeOH from 100:0 to 90:10 as eluent, affording the title compound (280 mg, 72%) as a white solid. HPLC-MS 3 minutes, RT=0.65, MS=129 [M+1].

Intermediate 45: (5R)-5-ethylimidazolidine-2,4-dione

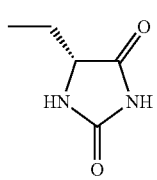

The title compound has been prepared by using the same foregoing methodology replacing (2S)-2-aminobutanamide 2,2,2-trifluoroacetate (Intermediate 42) with (2R)-2-aminobutanamide 2,2,2-trifluoroacetate (Intermediate 43). HPLC-MS 3 minutes, RT=0.60, MS=129 [M+1].

Intermediate 46: syn-2-[3-(7-methylspiro[2H-benzofuran-3,1'-cyclopropane]-4-yl)oxycyclobutyl]isoindoline-1,3-dione

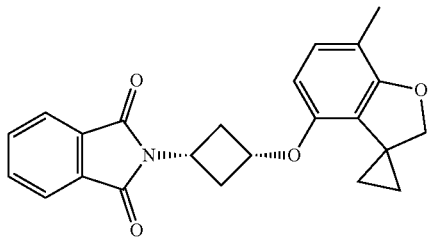 [SMILES: Cc1ccc(O[C@H]2C[C@@H](N3C(=O)c4ccccc4C3=O)C2)c2c1OCC21CC1]

anti-3-(7-Methylspiro[2H-benzofuran-3,1'-cyclopropane]-4-yl)oxycyclobutanol (140 mg, 0.57 mmol, Intermediate 12) was dissolved in THF (14 mL), then isoindoline-1,3-dione (100 mg, 0.68 mmol), triphenyl phosphine (179 mg, 0.68 mmol) and DIAD (126 mg, 0.62 mmol) were added. The reaction mixture was stirred at r.t. for 3 h, than it was concentrated. The crude was purified by flash chromatography (Biotage system) using a SNAP 25 g as column and cHex/EtOAc (from 9:1 to 4:6) as eluent, affording the title compound (165 mg) as a yellow oil. HPLC 3 min: Rt=2.83 min, [M+H$^+$]=376.

The following intermediate has been prepared by using the same foregoing methodology replacing anti-3-(7-methylspiro[2H-benzofuran-3,1'-cyclopropane]-4-yl)oxycyclobutanol (intermediate 12) with syn-3-(7-methylspiro[2H-benzofuran-3,1'-cyclopropane]-4-yl)oxycyclobutanol (intermediate 22):

| Int | Structure | LC-MS |
|---|---|---|
| 47 | 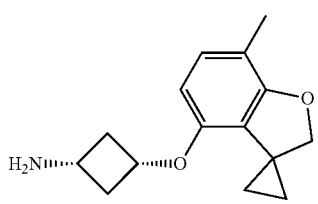 syn-2-[3-(7-methylspiro[2H-benzofuran-3,1'-cyclopropane]-4-yl)oxycyclobutyl]isoindoline-1,3-dione | 3 min RT: 2.88 min [M + H$^+$]: 376 |

Intermediate 48: syn-3-(7-methylspiro[2H-benzofuran-3,1'-cyclopropane]-4-yl)oxycyclobutanamine

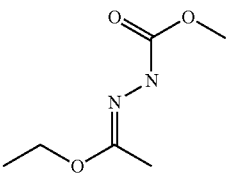

Syn-2-[3-(7-methylspiro[2H-benzofuran-3,1'-cyclopropane]-4-yl)oxycyclobutyl]isoindoline-1,3-dione (165 mg, 0.44 mmol, Intermediate 46) was dissolved in EtOH (6 mL), then hydrazine hydrate (40 mg, 0.44 mmol) was added. The reaction mixture was stirred at r.t. for 3 h, then concentrated. The crude was purified by flash chromatography (Biotage system) using a SNAP 25 g as column and cHex/EtOAc (from 1:1 to 0:10) and then further purified using EtOAc/NH$_3$ 7N in MeOH (95:5) as eluent, affording the title compound (82 mg) as colourless oil. HPLC 3 min: Rt=1.86 min, [M+H$^+$]=246.

The following intermediate has been prepared by using the same foregoing methodology replacing syn-2-[3-(7-methylspiro[2H-benzofuran-3,1'-cyclopropane]-4-yl)oxycyclobutyl]isoindoline-1,3-dione (intermediate 46) with anti-2-[3-(7-methylspiro[2H-benzofuran-3,1'-cyclopropane]-4-yl)oxycyclobutyl]isoindoline-1,3-dione (intermediate 47):

| Int | Structure | LC-MS |
|---|---|---|
| 49 | anti-3-(7-methylspiro[2H-benzofuran-3,1'-cyclopropane]-4-yl)oxycyclobutanamine | 3 min RT: 1.90 min [M + H$^+$]: 246 |

Intermediate 50: methyl (2E/Z)-2-(1-ethoxyethylidene)hydrazinecarboxylate

A mixture of methyl hydrazinocarboxylate (3.5 g, 38.8 mmol) and PTSA (148 mg, 0.78 mmol) in EtOH (7 ml) was purged with N$_2$ and triethyl orthoacetate (7.45 g, 40.8 mmol) was added. The mixture was stirred at 60° C. for 4 h. TLC shows the complete consumption of the starting material. To the solution was added NaHCO$_3$ (65 mg, 0.78 mmol) and the volatiles were evaporated in vacuo to give the title compound (5.6 g) as a waxy, colourless material. This compound was a mixture of E/Z isomers. HPLC 3 min: Rt=0.227 min, 0.338 min.

Intermediate 51: tert-butyl-dimethyl-spiro[2H-benzofuran-3,1'-cyclopropane]-4-yloxy-silane

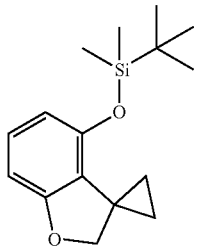 [SMILES: CC(C)(C)[Si](C)(C)Oc1cccc2c1C1(CC1)CO2]

To a solution of spiro[2H-benzofuran-3,1'-cyclopropane]-4-ol (Intermediate 85 of WO2012/076877, 578 mg, 3.6 mmol) and imidazole (291 mg, 4.3 mmol) in dichloromethane (20 mL), a solution of tert-Butyldimethylsilyl chloride (592 mg, 3.9 mmol) in dichloromethane (5 ml) was added and the reaction mixture was stirred at room temperature. After 2 hours, further tert-Butyldimethylsilyl chloride (200 mg, 1.3 mmol) and imidazole (100 mg, 1.5 mmol) were added and the reaction mixture was stirred at room temperature overnight. The mixture was concentrated up to 10 ml and ethyl acetate (30 ml) was added. The reaction mixture was washed with water (30 ml), aqueous HCl 0.2N (30 mL) and brine (30 mL). The organic layer was dried over sodium sulfate, filtered and concentrated and the residue was purified by flash chromatography (Biotage system) on silica gel using a SNAP 25 g as column and cyclohexane: ethyl acetate from 100:0 to 90:10 as eluent affording the title compound (815 mg) as colourless oil. HPLC 3 min: RT=3.16 min, [M+H$^+$]=277.

Intermediate 52: (7-bromospiro[2H-benzofuran-3,1'-cyclopropane]-4-yl)oxy-tert-butyl-dimethyl-silane

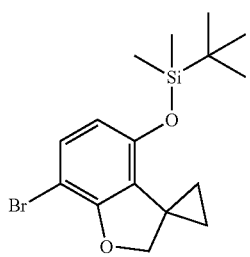 [SMILES: CC(C)(C)[Si](C)(C)Oc1ccc(Br)c2c1C1(CC1)CO2]

To a solution of tert-butyl-dimethyl-spiro[2H-benzofuran-3,1'-cyclopropane]-4-yloxy-silane (Intermediate 51, 600 mg, 2.17 mmol) in tetrahydrofuran (12 ml), N-Bromosuccinimide (386 mg, 2.17 mmol) was added and the reaction mixture was stirred at room temperature for 3 hours. Ethyl acetate (50 ml) and brine (50 ml) were added. Phases were separated and the organic layer was dried over sodium sulfate, filtered and concentrated. The residue was purified by flash chromatography (Biotage system) on silica gel using a SNAP 25 g as column and cyclohexane: ethyl acetate from 100:0 to 80:20 as eluent affording the title compound (739 mg) as white solid. HPLC 3 min: RT=3.27 min, [M+H]=355 and [M+2+H$^+$]=357.

Intermediate 53: 4-hydroxyspiro[2H-benzofuran-3,1'-cyclopropane]-7-carbaldehyde

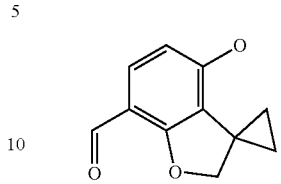

To a solution of (7-bromospiro[2H-benzofuran-3,1'-cyclopropane]-4-yl)oxy-tert-butyl-dimethyl-silane (Intermediate 52, 739 mg, 2.08 mmol) in dry tetrahydrofuran (14 ml) under nitrogen atmosphere at −78° C., n-Butyllithium 2.5 M in hexane (1.25 ml, 3.1 mmol) was added dropwise and the reaction mixture was stirred at the same temperature. The reaction was monitored by HPLC/MS and when it was complete, dimethylformamide (0.6 mL, 7.76 mmol) was added, the ice bath was removed and the reaction mixture was stirred for 1 hour. Dichloromethane (50 ml) and brine (50 ml) were added; phases were separated and the organic layer was dried over sodium sulfate, filtered and concentrated under vacuum.

The residue was dissolved in tetrahydrofuran (10 ml) and tetrabutylammonium fluoride solution 1.0 M in THF (3.12 ml, 3.12 mmol) was added. The reaction mixture was stirred for 1 hour at room temperature. Dichloromethane (30 ml) and brine (30 ml) were added; phases were separated and the organic layer was dried over sodium sulfate, filtered and concentrated. The residue was purified by flash chromatography (Biotage system) on silica gel using a SNAP 25 g as column and cyclohexane:ethyl acetate from 100:0 to 50:50 as eluent affording the title compound (135 mg) as yellow solid. HPLC 3 min: RT=1.89 min, [M+H$^+$]=191, [2M+Na+]=403.

Intermediate 54: 4-hydroxyspiro[2H-benzofuran-3,1'-cyclopropane]-7-carbaldehyde oxime

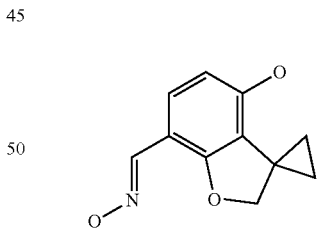

A mixture of 4-hydroxyspiro[2H-benzofuran-3,1'-cyclopropane]-7-carbaldehyde (Intermediate 53,135 mg, 0.71 mmol), potassium carbonate (107 mg, 0.78 mmol) and hydroxylamine hydrochloride (54.2 mg, 0.78 mmol) in methanol (5.5 ml) was stirred at room temperature until the reaction was complete. Brine (30 ml) and dichloromethane (2×30 ml) were added; phases were separated and the organic layer was dried over sodium sulfate, filtered and concentrated affording the title compound (145 mg) as yellow solid that was used in the next step without further purification. HPLC 3 min: RT=1.80 min, [M+H$^+$]=206.

Intermediate 55: (7-cyanospiro[2H-benzofuran-3,1'-cyclopropane]-4-yl) acetate

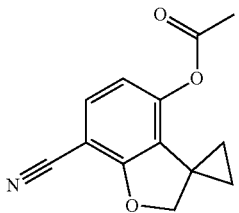 [SMILES: CC(=O)Oc1ccc(C#N)c2c1C1(CC1)CO2]

A mixture of 4-hydroxyspiro[2H-benzofuran-3,1'-cyclopropane]-7-carbaldehyde oxime (Intermediate 54, 145 mg, 0.71 mmol) and acetic anhydride (2.0 ml) was stirred at 130° C. for 8 hours. After cooling to room temperature, the reaction mixture was diluted with brine (20 ml) and extracted with ethyl acetate (2×20 ml). The organic layer was dried over sodium sulfate, filtered and concentrated affording the title compound (200 mg) as brown solid that was used in the next step without further purification. HPLC 3 min: Rt=2.23 min, [M+H$^+$]=230.

Intermediate 56: 4-hydroxyspiro[2H-benzofuran-3,1'-cyclopropane]-7-carbonitrile

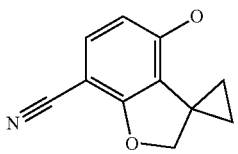

To a solution of (7-cyanospiro[2H-benzofuran-3,1'-cyclopropane]-4-yl) acetate (Intermediate 55, 200 mg, 0.87 mmol) in methanol (4.0 ml) and water (2.0 ml), an aqueous 1.0 N solution of sodium hydroxide (1.75 ml, 1.75 mmol) was added and the reaction mixture was stirred at room temperature for 30 minutes. An aqueous 0.1 N solution of hydrochloric acid was added while the pH was allowed to reach 5. The reaction mixture was extracted with ethyl acetate (2×30 ml); the organic layer was washed with brine (50 ml), dried over sodium sulfate, filtered and concentrated affording the title compound (121 mg) that was not further purified. HPLC 3 min: Rt=2.02 min, [M+H$^+$]=188, [2M+Na+]=397; $^1$H-NMR (500 MHz, DMSO-d6): δ ppm 10.52 (bs, 1H), 7.21 (d, 1H), 6.36 (d, 1H), 4.52 (s, 2H), 1.44-1.41 (m, 2H), 0.87-0.85 (m, 2H).

Intermediate 57: 3-[3-[tert-butyl(dimethyl)silyl]oxy-cyclobutyl]-5,5-dimethyl-imidazolidine-2,4-dione

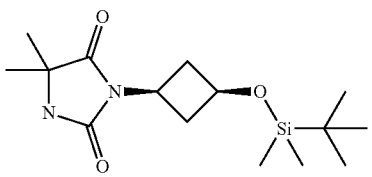 [SMILES: CC1(C)NC(=O)N([C@H]2C[C@@H](O[Si](C)(C)C(C)(C)C)C2)C1=O]

To a solution of 3-[tert-butyl(dimethyl)silyl]oxycyclobutanol (Intermediate 27, 220 mg, 1.09 mmol), 5,5-dimethyl-hydantoin (153 mg, 1.20 mmol) and triphenylphosphine (343 mg, 1.31 mmol) in dry tetrahydrofuran (2 mL), at room temperature DIAD (225 uL, 1.14 mmol) was added. The reaction mixture was stirred at 60° C. overnight. Volatiles were removed under vacuum and the crude was purified by flash chromatography (Biotage system) on silica gel using a SNAP 25 g as column and Cyclohexane: Ethyl acetate from 100:0 to 40:60 as eluent. The isolated fractions were still impure and they were further purified by reverse flash chromatography (Biotage system) on C18 phase using a SNAP 12 g as column and Water: Acetonitrile from 95:5 to 0:100 as eluent affording the title compound (101 mg). HPLC 3 min: RT=2.62 min, [M+H$^+$]=313

Intermediate 58: 3-(3-hydroxycyclobutyl)-5,5-dimethyl-imidazolidine-2,4-dione

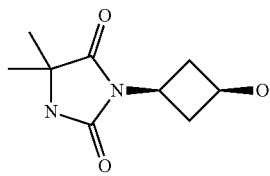

To a solution of 3-[3-[tert-butyl(dimethyl)silyl]oxycyclobutyl]-5,5-dimethyl-imidazolidine-2,4-dione (Intermediate 57, 101 mg, 0.32 mmol) in dry THF (1 mL), at 0° C. tetrabutylammonium fluoride solution 1.0 M in THF (320 uL. 0.32 mmol) was added. The reaction mixture was stirred at room temperature for 2 hours. The reaction mixture was diluted with ethyl acetate (5 mL) and the organic phase was washed with brine (2×5 ml), dried with Na2SO4 and concentrated under vacuum. The residue was purified by reverse flash chromatography (Biotage system) on C18 phase using a SNAP 12 g as column and water: acetonitrile from 95:5 to 15:85 as eluent affording the title compound (20 mg) as white solid. HPLC 3 min: RT=1.28 min, [M+H$^+$]=199, [M+Na$^+$]=221.

Intermediate 59: 3-[(2,2,2-trifluoroacetyl)amino]oxetane-3-carboxylic acid

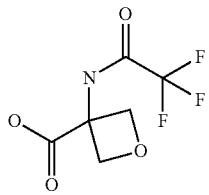 [SMILES: O=C(NC1(C(=O)O)COC1)C(F)(F)F]

3-amino oxetane-3-carboxylic acid (57 mg, 0.49 mmol) was suspended in dichloromethane (2 mL) and the suspension was cooled to 0° C. Trifluoroacetic anhydride (90 uL, 0.63 mmol) was added at the same temperature and the reaction mixture was stirred for 3 hours while the temperature was allowed to reach room temperature. The reaction mixture was concentrated under vacuum and the residue was re-suspended in Toluene (2 mL) and dried again affording the title compound (93 mg) as white solid. HPLC 3 min: RT=0.53, [M+H$^+$]=214.

Intermediate 60: N-[3-(7-methylspiro[2H-benzofuran-3,1'-cyclopropane]-4-yl)oxycyclobutyl]-3-[(2,2,2-trifluoroacetyl)amino]oxetane-3-carboxamide

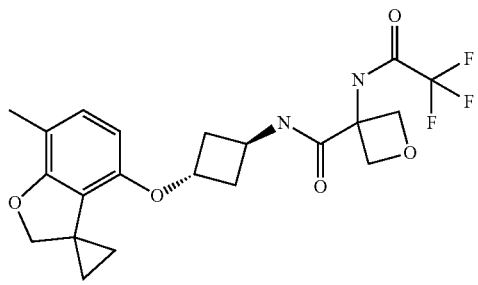 [SMILES: Cc1ccc(O[C@H]2C[C@H](NC(=O)C3(NC(=O)C(F)(F)F)COC3)C2)c2c1OCC21CC1]

To a solution of 3-[(6-isopropenyl-5-oxaspiro[2.4]hept-6-en-7-yl)methoxy]cyclobutanamine (Intermediate 49, 28 mg, 0.11 mmol) in ethyl acetate (3 mL), triethylamine (38 uL, 0.28 mmol) and 3-[(2,2,2-trifluoroacetyl)amino]oxetane-3-carboxylic acid (Intermediate 59, 27 mg, 0.13 mmol) were added and the reaction mixture was cooled to 0° C. Propylphosphonic anhydride solution ≥50 wt. % in ethyl acetate (80 uL, 0.13 mmol) was slowly added and the reaction mixture was stirred at 0° C. for 1 hour. Brine (10 mL) was added and the reaction mixture was extracted with Ethyl acetate (10 mL). The organic phase was dried with $Na_2SO_4$, concentrated under vacuum and the crude the crude was purified by flash chromatography (Biotage system) on silica gel using a SNAP 10 g as column and Cyclohexane: Ethyl acetate from 100:0 to 30:70 as eluent) affording the title compound (31 mg). HPLC 3 min: RT=2.31, [M+H$^+$]=441.

Intermediate 61: 3-amino-N-[3-(7-methylspiro[2H-benzofuran-3,1'-cyclopropane]-4-yl)oxycyclobutyl]oxetane-3-carboxamide

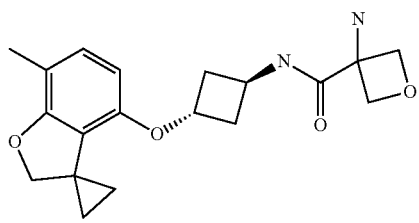 [SMILES: Cc1ccc(O[C@H]2C[C@H](NC(=O)C3(N)COC3)C2)c2c1OCC21CC1]

To a solution of N-[3-(7-methylspiro[2H-benzofuran-3,1'-cyclopropane]-4-yl)oxycyclobutyl]-3-[(2,2,2-trifluoroacetyl)amino]oxetane-3-carboxamide (Intermediate 60, 30 mg, 0.068 mmol) in THF:MeOH:H2O (3:1:1) (2.5 mL), at 0° C. LiOH.H2O (29 mg, 0.68 mmol) was added and the reaction mixture was stirred at 70° C. for 1 hour. Brine (10 mL) was added and the reaction mixture was extracted with Ethyl acetate (10 mL). The organic phase was dried with $Na_2SO_4$, concentrated under vacuum and the crude was purified by flash chromatography (Biotage system) on silica gel using a SNAP 10 g as column and Dichloromethane: Methanol from 100:0 to 80:20 as eluent; the isolated fractions were still impure and they were further purified by reverse flash chromatography (Biotage system) on C18 phase using a SNAP 12 g as column and Water: Acetonitrile from 95:5 to 5:95 as eluent) affording the title compound (7 mg) as white solid. HPLC 3 min: RT=1.92 min, [M+H$^+$]=345.

Intermediate 62: tert-butyl N-[(1S)-1-methyl-2-[[3-(7-methylspiro[2H-benzofuran-3,1'-cyclopropane]-4-yl)oxycyclobutyl]amino]-2-oxo-ethyl]carbamate

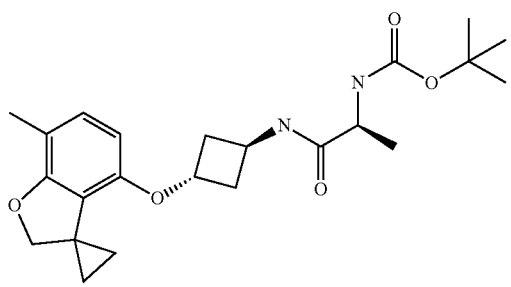 [SMILES: Cc1ccc(O[C@H]2C[C@H](NC(=O)[C@H](C)NC(=O)OC(C)(C)C)C2)c2c1OCC21CC1]

To a solution of 3-[(6-isopropenyl-5-oxaspiro[2.4]hept-6-en-7-yl)methoxy]cyclobutanamine (Intermediate 49, 50 mg, 0.20 mmol) in ethyl acetate (2 mL), triethylamine (70 uL, 0.5 mmol) and N-(tert-Butoxycarbonyl)-L-alanine (42 mg, 0.22 mmol) were added and the reaction mixture was cooled to 0° C. Propylphosphonic anhydride solution ≥50 wt. % in ethyl acetate (130 uL, 0.22 mmol) was slowly added and the reaction mixture was stirred at 0° C. for 1 hour. Brine (10 mL) was added and the reaction mixture was extracted with Ethyl acetate (10 mL). The organic phase was dried with Na2SO4, concentrated under vacuum and the crude was purified by flash chromatography (Biotage system) on silica gel using a SNAP 10 g as column and Cyclohexane: Ethyl acetate from 90:10 to 40:60 as eluent affording the title compound (60 mg). HPLC 3 min: RT=2.44 min, [M−56+H$^+$]=361

Intermediate 63: tert-butyl N-[(1R)-1-methyl-2-[[3-(7-methylspiro[2H-benzofuran-3,1'-cyclopropane]-4-yl)oxycyclobutyl]amino]-2-oxo-ethyl]carbamate

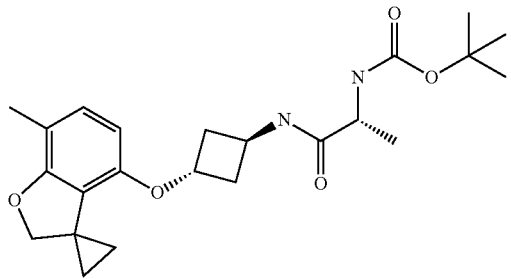 [SMILES: Cc1ccc(O[C@H]2C[C@H](NC(=O)[C@@H](C)NC(=O)OC(C)(C)C)C2)c2c1OCC21CC1]

Intermediate 63 has been prepared using the same methodology described for Intermediate 62 replacing N-(tert-Butoxycarbonyl)-L-alanine with N-(tert-Butoxycarbonyl)-D-alanine. HPLC 3 min: RT=2.47 min, [M−56+H$^+$]=361.

Intermediate 64: (2S)-2-amino-N-[3-(7-methylspiro [2H-benzofuran-3,1'-cyclopropane]-4-yl)oxycyclobutyl]propanamide

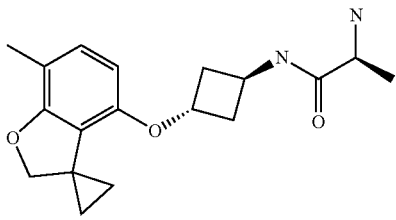 [SMILES: Cc1ccc(O[C@H]2C[C@H](NC(=O)[C@H](C)N)C2)c2c1OCC21CC1]

To a solution of tert-butyl N-[(1S)-1-methyl-2-[[3-(7-methylspiro[2H-benzofuran-3,1'-cyclopropane]-4-yl)oxycyclobutyl]amino]-2-oxo-ethyl]carbamate (Intermediate 62, 60 mg, 0.14 mmol) in dichloromethane (4 mL), at −15° C. trifluoroacetic acid (400 uL) was added. The reaction mixture was stirred for 1.5 hours at the same temperature. An aqueous saturated solution of NaHCO₃ was added while the pH was allowed to reach 8, ethyl acetate (10 ml) was added, the mixture shaken and the two phases separated. The organic phase was concentrated under vacuum and the crude was purified by flash chromatography (Biotage system) on silica gel using a SNAP 10 g as column and Dichloromethane: Methanol from 98:2 to 85:15 as eluent affording the title compound (6 mg). HPLC 3 min: RT=1.93 min, [M+H⁺]=317

Intermediate 65: (2R)-2-amino-N-[3-(7-methylspiro [2H-benzofuran-3,1'-cyclopropane]-4-yl)oxycyclobutyl]propanamide

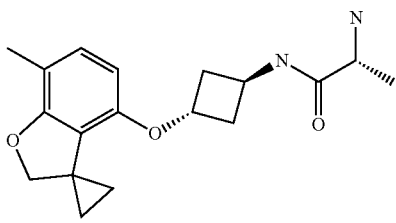 [SMILES: Cc1ccc(O[C@H]2C[C@H](NC(=O)[C@@H](C)N)C2)c2c1OCC21CC1]

Intermediate 65 has been prepared using the same methodology described for Intermediate 64 replacing N-[(1S)-1-methyl-2-[[3-(7-methylspiro[2H-benzofuran-3,1'-cyclopropane]-4-yl)oxycyclobutyl]amino]-2-oxo-ethyl]carbamate (Intermediate 62) with N-[(1R)-1-methyl-2-[[3-(7-methylspiro[2H-benzofuran-3,1'-cyclopropane]-4-yl)oxycyclobutyl]amino]-2-oxo-ethyl]carbamate (Intermediate 64). HPLC 3 min: RT=1.91 min, [M+H⁺]=317.

Example 1 syn-5,5-dimethyl-3-[3-[4-methyl-3-(trifluoromethoxy)phenoxy]cyclobutyl] imidazolidine-2,4-dione

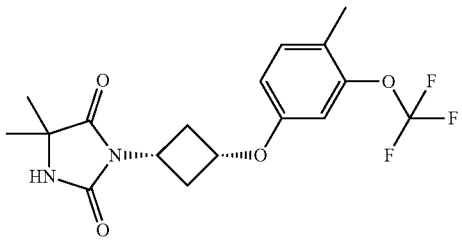 [SMILES: Cc1ccc(O[C@H]2C[C@@H](N3C(=O)NC(C)(C)C3=O)C2)cc1OC(F)(F)F]

DIAD (43 uL, 0.22 mmol) was added to a mixture of anti-3-[4-methyl-3-(trifluoromethoxy)phenoxy]cyclobutanol (50 mg, 0.2 mmol, Intermediate 11), 5,5-dimethylimidazolidine-2,4-dione (39 mg, 0.3 mmol) and triphenylphosphine (80 mg, 0.3 mmol) in THF (5 mL). The reaction mixture was stirred at r.t. for 3 h, then concentrated. The crude was purified by flash chromatography (Biotage system) on silica gel using a SNAP 10 g+10 g as column and cHex/EtOAc as eluent from 85:15 to 4:6 affording 40 mg of the title compound as a white solid. HPLC 8 min: Rt=5.37 min, [M+H⁺]=373; 1H-NMR: DMSO-d6, δ ppm 8.3 (bs, 1H), 7.28 (d, 1H), 6.84 (dd, 1H), 6.78 (bs, 1H), 4.46-4.55 (m, 1H), 4.09-4.19 (m, 1H), 2.8-2.9 (m, 2H), 2.66-2.75 (m, 2H), 2.19 (s, 3H), 1.26 (s, 6H).

The syn-configuration has been assigned via NOESY NMR experiment.

The following examples have been prepared by using the same foregoing methodology replacing anti-3-[4-methyl-3-(trifluoromethoxy)phenoxy]cyclobutanol (Intermediate 11) with the appropriate alcohol intermediate:

| Ex | Structure | Alcohol intermediate | LC-MS | 1H-NMR |
|---|---|---|---|---|
| 2 | ![structure] syn-5,5-dimethyl-3-[3-(7-methylspiro[2H-benzofuran-3,1'-cyclopropane]-4-yl)oxycyclobutyl] imidazolidine-2,4-dione | anti-3-(7-methylspiro[2H-benzofuran-3,1'-cyclopropane]-4-yl) oxycyclobutanol, Intermediate 12 | 3 min RT: 5.1 min [M + H⁺]: 357 | DMSO-d6, δ ppm 8.27 (bs, 1H), 6.77 (d, 1H), 6.2 (d, 1H), 4.39-4.48 (m, 1H), 4.38 (s, 2H), 4.07-4.17 (m, 1H), 2.7-2.79 (m, 2H), 2.58-2.68 (m, 2H), 2.4 (s, 3H), 1.49-1.53 (m, 2H), 1.26 (s, 6H), 0.8-0.84 (m, 2H). |

-continued

| Ex | Structure | Alcohol intermediate | LC-MS | 1H-NMR |
|---|---|---|---|---|
| 3 | syn-4-[3-(4,4-dimethyl-2,5-dioxo-imidazolidin-1-yl)cyclobutoxy]-2-isopropyl-benzonitrile | anti-4-(3-hydroxycyclobutoxy)-2-isopropyl-benzonitrile, Intermediate 13 | 8 min RT: 4.9 min [M + H⁺]: 342 | DMSO-d6, δ ppm 8.31 (bs, 1H), 7.69 (d, 1H), 6.95 (d, 1H), 6.86 (dd, 1H), 4.58-4.66 (m, 1H), 4.12-4.22 (m, 1H), 3.12-3.22 (m, 1H), 2.83-2.93 (m, 2H), 2.71-2.81 (m, 2H), 2.4 (s, 3H), 1.49-1.53 (m, 2H), 1.23-1.26 (m, 12H). |
| 4 | anti-5,5-dimethyl-3-[3-[4-methyl-3-(trifluoromethoxy)phenoxy]cyclobutyl]imidazolidine-2,4-dione | syn-3-[4-methyl-3-(trifluoromethoxy)phenoxy]cyclobutanol, Intermediate 21 | 3 min RT: 2.56 min [M + H⁺]: 373 | DMSO-d6, δ ppm 8.33 (bs, 1H), 7.3 (d, 1H), 6.8 (dd, 1H), 6.75 (bs, 1H), 4.97-5.06 (m, 1H), 4.61-4.71 (m, 1H), 2.98-3.08 (m, 2H), 2.37-2.47 (m, 2H), 2.19 (s, 3H), 1.29 (s, 6H). The anti configuration has been assigned via NOESY NMR experiment |
| 5 | anti-5,5-dimethyl-3-[3-(7-methylspiro[2H-benzofuran-3,1'-cyclopropane]-4-yl)oxycyclobutyl]imidazolidine-2,4-dione | syn-3-(7-methylspiro[2H-benzofuran-3,1'-cyclopropane]-4-yl)oxycyclobutanol, Intermediate 22 | 8 min RT: 5.26 min [M + H⁺]: 357 | |
| 6 | anti-4-[3-(4,4-dimethyl-2,5-dioxo-imidazolidin-1-yl)cyclobutoxy]-2-isopropyl-benzonitrile | syn-4-(3-hydroxycyclobutoxy)-2-isopropyl-benzonitrile, Intermediate 23 | 8 min RT: 5.02 min [M + H⁺]: 342 | |

| Ex | Structure | Alcohol intermediate | LC-MS | 1H-NMR |
|---|---|---|---|---|
| 7 | syn-5,5-dimethyl-3-[3-[3-(trifluoromethoxy)phenoxy]cylobutyl]imidazolidine-2,4-dione | anti-3-[3-(trifluoromethoxy)phenoxy]cyclobutanol, Intermediate 14 | 3 min RT: 2.43 min [M + H$^+$]: 359 | |
| 8 | anti-5,5-dimethyl-3-[3-[3-(trifluoromethoxy)phenoxyl]cyclobutyl]imidazolidine-2,4-dione | syn-3-[3-(trifluoromethoxy)phenoxy]cyclobutanol, Intermediate 16 | 3 min RT: 2.47 min [M + H$^+$]: 359 | |
| 9 | syn-3-[3-(2-tert-butylphenoxy)cyclobutyl]-5,5-dimethyl-imidazolidine-2,4-dione | anti-3-(2-tert-butylphenoxy)cyclobutanol, Intermediate 15 | 3 min RT: 2.92 min [M + H$^+$]: 331 | |
| 10 | anti-3-[3-(2-tert-butylphenoxy)cyclobutyl]-5,5-dimethyl-imidazolidine-2,4-dione | syn-3-(2-tert-butylphenoxy)cyclobutanol, Intermediate 17 | 3 min RT: 2.94 min [M + H$^+$]: 331 | |

-continued

| Ex | Structure | Alcohol intermediate | LC-MS | 1H-NMR |
|---|---|---|---|---|
| 11 | syn-3-tert-butyl-4-[3-(4,4-dimethyl-2,5-dioxo-imidazolidin-1-yl)cyclobutoxy]benzonitrile | anti-3-tert-butyl-4-(3-hydroxycyclobutoxy)benzonitrile, Intermediate 34 | 3 min RT: 2.44 min [M + H$^+$]: 356 | |
| 12 | anti-3-tert-butyl-4-[3-(4,4-dimethyl-2,5-dioxo-imidazolidin-1-yl)cyclobutoxy]benzonitrile | syn-3-tert-butyl-4-(3-hydroxycyclobutoxy)benzonitrile, Intermediate 35 | 3 min RT: 2.47 min [M + H$^+$]: 356 | |
| 13 | syn-4-[3-(4,4-dimethyl-2,5-dioxo-imidazolidin-1-yl)cyclobutoxy]-2-(trifluoromethoxy)benzonitrile | Anti-4-(3-hydroxycyclobutoxy)-2-(trifluoromethoxy)benzonitrile, Intermediate 36 | 3 min RT: 2.29 min [M + H$^+$]: 384 | |
| 14 | anti-4-[3-(4,4-dimethyl-2,5-dioxo-imidazolidin-1-yl)cyclobutoxy]-2-(trifluoromethoxy)benzonitrile | syn-4-(3-hydroxycyclobutoxy)-2-(trifluoromethoxy)benzonitrile, Intermediate 37 | 3 min RT: 2.33 min [M + H$_2$O]$^+$: 401 | |

| Ex | Structure | Alcohol intermediate | LC-MS | 1H-NMR |
|---|---|---|---|---|
| 15 | 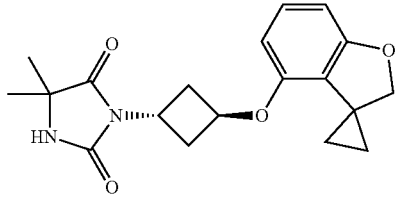 [SMILES: CC1(C)NC(=O)N([C@H]2C[C@H](Oc3cccc4c3C3(CC3)CO4)C2)C1=O]<br>anti-5,5-dimethyl-3-(3-spiro[2H-benzofuran-3,1'-cyclopropane]-4-yloxycyclobutyl)imidazolidine-2,4-dione | syn-3-spiro[2H-benzofuran-3,1'-cyclopropane]-4-yloxycyclobutanol Intermediate 38 | 3 min RT: 2.33 min [M + H⁺]: 343 | |
| 16 | 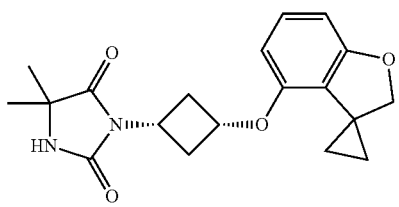 [SMILES: CC1(C)NC(=O)N([C@H]2C[C@@H](Oc3cccc4c3C3(CC3)CO4)C2)C1=O]<br>syn-5,5-dimethyl-3-(3-spiro[2H-benzofuran-3,1'-cyclopropane]-4-yloxycyclobutyl)imidazolidine-2,4-dione | anti-3-spiro[2H-benzofuran-3,1'-cyclopropane]-4-yloxycyclobutanol Intermediate 39 | 3 min RT: 2.29 min [M + H⁺]: 343 | |

The following examples have been prepared using the foregoing methodology and replacing the 5,5-dimethylimidazolidine-2,4-dione with (5R)-5-ethylimidazolidine-2,4-dione (Intermediate 45):

| Ex | Structure | Alcohol intermediate | LC-MS |
|---|---|---|---|
| 17 | 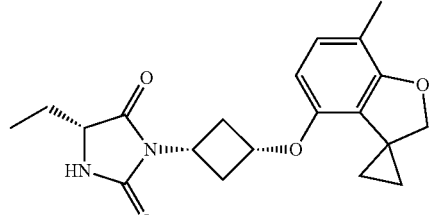<br>syn-(5R)-5-ethyl-3-[3-(7-methylspiro[2H-benzofuran-3,1'-cyclopropane]-4-yl)oxycyclobutyl]imidazolidine-2,4-dione | anti-3-(7-methylspiro[2H-benzofuran-3,1'-cyclopropane]-4-yl)oxycyclobutanol, Intermediate 12 | 3 min RT: 2.45 min [M + H⁺]: 357 |
| 18 | 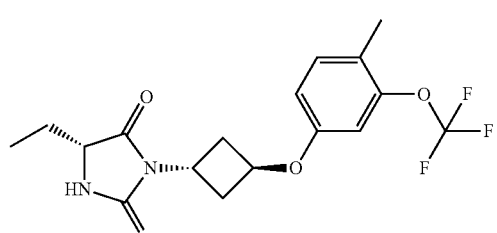<br>anti-(5R)-5-ethyl-3-[3-[4-methyl-3-(trifluoromethoxy)phenoxy]cyclobutyl]imidazolidine-2,4-dione | syn-3-[4-methyl-3-(trifluoromethoxy)phenoxy]cyclobutanol, Intermediate 21 | 3 min RT: 2.56 min [M + H⁺]: 373 |

-continued

| Ex | Structure | Alcohol intermediate | LC-MS |
| --- | --- | --- | --- |
| 19 | anti-(5R)-5-ethyl-3-[3-(7-methylspiro[2H-benzofuran-3,1'-cyclopropane]-4-yl)oxycyclobutyl]imidazolidine-2,4-dione | syn-3-(7-methylspiro[2H-benzofuran-3,1'-cyclopropane]-4-yl)oxycyclobutanol, Intermediate 22 | 3 min RT: 2.51 min [M + H⁺]: 357 |

The following examples have been obtained using the foregoing methodology and replacing the 5,5-dimethylimidazolidine-2,4-dione with (5S)-5-ethylimidazolidine-2,4-dione (Intermediate 44):

| Ex | Structure | Alcohol intermediate | LC-MS |
| --- | --- | --- | --- |
| 20 | syn-(5S)-5-ethyl-3-[3-(7-methylspiro[2H-benzofuran-3,1'-cyclopropane]-4-yl)oxycyclobutyl]imidazolidine-2,4-dione | anti-3-(7-methylspiro[2H-benzofuran-3,1'-cyclopropane]-4-yl)oxycyclobutanol, Intermediate 12 | 8 min RT: 5.2 min [M + H⁺]: 357 |
| 21 | anti-(5S)-5-ethyl-3-[3-[4-methyl-3-(trifluoromethoxy)phenoxy]cyclobutyl]imidazolidine-2,4-dione | syn-3-[4-methyl-3-(trifluoromethoxy)phenoxy]cyclobutanol, Intermediate 21 | 3 min RT: 2.57 min [M + H⁺]: 373 |
| 22 | anti-(5S)-5-ethyl-3-[3-(7-methylspiro[2H-benzofuran-3,1'-cyclopropane]-4-yl)oxycyclobutyl]imidazolidine-2,4-dione | syn-3-(7-methylspiro[2H-benzofuran-3,1'-cyclopropane]-4-yl)oxycyclobutanol, Intermediate 22 | 3 min RT: 2.5 min [M + H⁺]: 357 |

Example 23: syn-3-methyl-4-[3-(7-methylspiro[2H-benzofuran-3,1'-cyclopropane]-4-yl)oxycyclobutyl]-1H-1,2,4-triazol-5-one

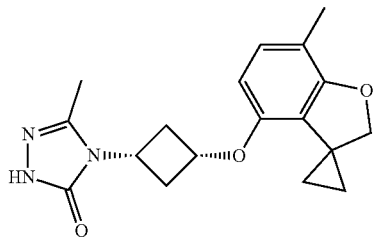 [SMILES: Cc1ccc(O[C@H]2C[C@@H](n3c(C)n[nH]c3=O)C2)c2c1OCC21CC1]

A mixture of ethyl methyl (2E/Z)-2-(1-ethoxyethylidene)hydrazinecarboxylate (157 mg, 0.98 mmol, Intermediate 50) and syn-3-(7-methylspiro[2H-benzofuran-3,1'-cyclopropane]-4-yl)oxycyclobutanamine (80 mg, 0.33 mmol, Intermediate 48) in MeOH (1.5 mL) was stirred at 100° C. overnight. Solvent was evaporated and the crude purified by flash chromatography-reverse phase (Biotage system) using a SNAP 30 g column and water/acetonitrile (from 95:5 to 20:80) as eluent, affording the title compound (42.5 mg) as a white solid.

HPLC 3 min: Rt=2.26 min, [M+H$^+$]=328 The following example has been obtained using the foregoing methodology and replacing syn-3-(7-methylspiro[2H-benzofuran-3,1'-cyclopropane]-4-yl)oxycyclobutanamine (Intermediate 48) with anti-3-(7-methylspiro[2H-benzofuran-3,1'-cyclopropane]-4-yl)oxycyclobutanamine (Intermediate 49):

| Ex | Structure | LC-MS |
|---|---|---|
| 24 | 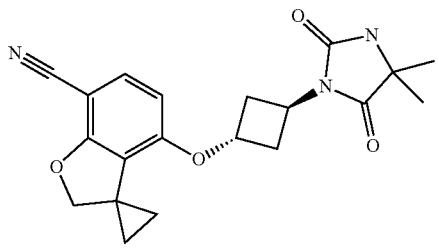 anti-3-methyl-4-[3-(7-methylspiro[2H-benzofuran-3,1'-cyclopropane]-4-yl)oxycyclobutyl]-1H-1,2,4-triazol-5-one | 3 min RT: 2.28 min [M + H$^+$]: 328 |

Example 25: 4-[3-(4,4-dimethyl-2,5-dioxo-imidazolidin-1-yl)cyclobutoxy]spiro[2H-benzofuran-3,1'-cyclopropane]-7-carbonitrile

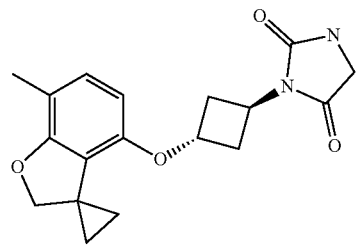

To a solution of 3-(3-hydroxycyclobutyl)-5,5-dimethyl-imidazolidine-2,4-dione (Intermediate 58, 20 mg, 0.10 mmol), 4-hydroxyspiro[2H-benzofuran-3,1'-cyclopropane]-7-carbonitrile (Intermediate 56, 20 mg, 0.15 mmol) and triphenylphosphine (31 mg, 0.12 mmol) in dry tetrahydrofuran (1 mL), at room temperature DIAD (20 uL, 0.10 mmol) was added. The reaction mixture was stirred at 60° C. for 72 hours. The mixture was concentrated under vacuum and the crude was purified by flash chromatography (Biotage system) on silica gel using a SNAP 10 g as column and Cyclohexane: Ethyl acetate from 100:0 to 40:60 as eluent affording the title compound (11 mg) as a white solid. HPLC 3 min: RT=2.32 min, [M+H$^+$]=368.

$^1$H NMR (CDCl$_3$, 500 MHz): 7.19 (1H, d), 6.15 (1H, d), 5.2 (1H, m), 5.0 (1H, m), 4.8 (1H, m), 4.57 (2H, s), 3.13 (2H, m), 2.45 (2H, m), 1.65 (2H, m), 1.44 (6H, s), 1.86 (2H, m).

Example 26: 6-[3-(7-methylspiro[2H-benzofuran-3,1'-cyclopropane]-4-yl)oxycyclobutyl]-2-oxa-6,8-diazaspiro[3.4]octane-5,7-dione

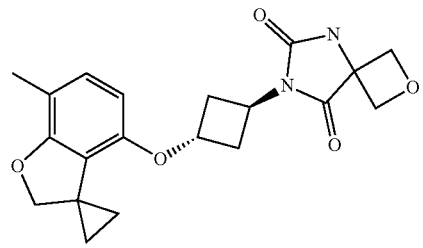 [SMILES: Cc1ccc(O[C@H]2C[C@H](N3C(=O)NC4(COC4)C3=O)C2)c2c1OCC21CC1]

To a solution of 3-amino-N-[3-(7-methylspiro[2H-benzofuran-3,1'-cyclopropane]-4-yl) oxycyclobutyl] oxetane-3-carboxamide (Intermediate 61, 6 mg, 0.017 mmol) and triethylamine (25 uL, 0.17 mmol) in dichloromethane (1 mL), at 0° C. a solution of triphosgene (4 mg, 0.014 mmol) in dichloromethane (1 mL) was slowly added and the reaction mixture was stirred for 30 minutes at the same temperature. The reaction mixture was concentrated under vacuum and the crude was purified by flash chromatography (Biotage system) on silica gel using a SNAP 10 g as column and Cyclohexane: Ethyl acetate from 60:40 to 0:100 as eluent) affording the title compound (4 mg) as white solid. HPLC 3 min: RT=2.25 min, [M+H$^+$]=371.

$^1$H NMR (CDCl$_3$, 500 MHz): 6.75 (1H, d), 6.03 (1H, d), 5.9 (1H, m), 5.05 (2H, d), 4.9 (1H, m), 4.8 (1H, m), 4.72 (2H, d), 4.43 (2H, s), 3.1 (2H, m), 2.4 (2H, m), 2.14 (3H, s), 1.61 (2H, m), 0.78 (2H, m).

Example 27: 3-[3-(7-methylspiro[2H-benzofuran-3,1'-cyclopropane]-4-yl)oxycyclo butyl]imidazolidine-2,4-dione To a solution of syn-3-(7-methylspiro[2H-benzofuran-3,1'-cyclopropane]-4-yl)oxycyclobutanol (Intermediate 22, 30 mg, 0.12 mmol), imidazolidine-2,4-dione (18 mg, 0.18 mmol) and triphenylphosphine (38 mg, 0.14 mmol) in dry THF, DIAD (25 µl, 0.13 mmol) was added and the reaction mixture was stirred at 60 C. When the reaction was complete (monitored via HPLC and TLC) volatiles were removed under reduced pressure and the residue was purified by flash chromatography (Biotage system) on silica gel using a SNAP 10 g as column and Cyclohexane: Ethyl acetate from 80:20 to 50:50 as eluent the isolated fractions were still impure and they were further purified by reverse flash chromatography (Biotage system) on C18 phase using a SNAP 12 g as column and Water: Acetonitrile from 95:5 to 20:80 as eluent) affording the title compound (6 mg) as white solid. HPLC 3 min: RT=2.33 min, [M+H$^+$]=329.

Example 28: (5S)-5-methyl-3-[3-(7-methylspiro[2H-benzofuran-3,1'-cyclopropane]-4-yl)oxycyclobutyl]imidazolidine-2,4-dione

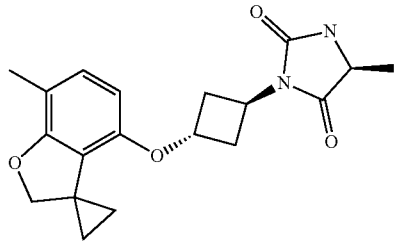

To a solution of (2S)-2-amino-N-[3-(7-methylspiro[2H-benzofuran-3,1'-cyclopropane]-4-yl) oxycyclobutyl] propanamide (Intermediate 64, 6 mg, 0.02 mmol) and triethylamine (25 uL, 0.17 mmol) in dichloromethane (1 mL), at 0° C. a solution of triphosgene (4 mg, 0.014 mmol) in dichloromethane (1 mL) was slowly added. The reaction mixture was concentrated under vacuum and the crude was purified by flash chromatography (Biotage system) on silica gel using a SNAP 10 g as column and Cyclohexane: Ethyl acetate from 90:10 to 30:70 as eluent affording the title compound (1.2 mg) as white solid. HPLC 3 min: RT=2.30 min, [M+H$^+$]=343.

$^1$H NMR (CDCl$_3$, 500 MHz): 6.75 (1H, d), 6.02 (1H, d), 5.2 (1H, m), 4.9 (1H, m), 4.8 (1H, m), 4.43 (2H, s), 4.0 (2H, m), 3.1 (2H, m), 2.41 (1H, m), 2.1 (3H, s), 1.62 (2H, m), 1.45 (3H, d), 0.78 (2H, m).

Example 29: (5R)-5-methyl-3-[3-(7-methylspiro[2H-benzofuran-3,1'-cyclopropane]-4-yl)oxycyclobutyl]imidazolidine-2,4-dione

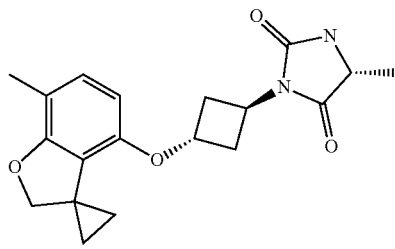

Example 29 has been prepared using the same methodology described for Example 28 replacing (2S)-2-amino-N-[3-(7-methylspiro[2H-benzofuran-3,1'-cyclopropane]-4-yl) oxycyclobutyl]propanamide (Intermediate 64) with (2R)-2-amino-N-[3-(7-methylspiro[2H-benzofuran-3,1'-cyclopropane]-4-yl) oxycyclobutyl] propanamide (Intermediate 65). HPLC 3 min: RT=2.29 min, [M+H$^+$]=343.

BIOLOGICAL EXAMPLES

Biological Example 1: Measurement of Kv3.1, Kv3.2 and Kv3.3 Channel Modulation

The ability of the compounds of the invention to modulate the voltage-gated potassium channel subtypes Kv3.3/Kv3.2/Kv3.1 may be determined using the following assay. Analogous methods may be used to investigate the ability of the compounds of the invention to modulate other channel subtypes.

Cell Biology

To assess compound effects on human Kv3.3 channels (hKv3.3), a stable cell line expressing human Kv3.3 channels was created by transfecting Chinese Hamster Ovary (CHO)-K1 cells with a pBacMire_KCNC-3 vector. Cells were cultured in DMEM/F12 (Gibco) supplemented with 10% Foetal Bovine Serum (Gibco), 1× non-essential amino acids (Invitrogen) and geneticin (G418) 400 microg/mL. Cells were grown and maintained at 37° C. in a humidified environment containing 5% CO$_2$ in air.

To assess compound effects on human Kv3.2 channels (hKv3.2), a stable cell line expressing human Kv3.2 channels (hKv3.2) was created by transfecting CHO-K1 cells with a pCIH5-hKv3.2 vector. Cells were cultured in DMEM/F12 medium supplemented by 10% Foetal Bovine Serum, 1× non-essential amino acids (Invitrogen) and 500 ug/ml of Hygromycin-B (Invitrogen). Cells were grown and maintained at 37° C. in a humidified environment containing 5% CO$_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pCDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 h later.

Cell Preparation for Ion Works Quattro™ Experiments The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml.

All the solutions added to the cells were pre-warmed to 37° C.

Electrophysiology

Experiments were conducted at r.t. using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances (Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. For hKv3.2 and hKv3.1 assays, from the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. For hKv3.3 assays, from the holding potential of −70 mV, a first test pulse to 0 mV was applied for 500 ms and following a further 100 ms at −70 mV, a second pulse to 40 mV was applied for 200 ms. These longer test pulses were used to study inactivation of hKv3.3 channels. Test pulses protocol may be performed in the absence (pre-read) and presence (post-read) of the test compound. Pre- and post-reads may be separated by the compound addition followed by a 3 minute incubation.

Solutions and Drugs

The intracellular solution contained the following (in mM): K-gluconate 100, KCl 54, MgCl$_2$ 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): CaCl$_2$ 0.90, KCl 2.67, KH$_2$PO$_4$ 1.47, MgCl.6H$_2$O 0.493, NaCl 136.9, Na$_3$PO$_4$ 8.06, with a pH of 7.4.

Compounds of use in the invention (or reference compounds such as N-cyclohexyl-N-[(7,8-dimethyl-2-oxo-1,2-dihydro-3-quinolinyl)methyl]-N'-phenylurea) were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and external solution containing 0.05% pluronic acid (66 μL) was added. 3.5 μL from each plate containing a compound of the invention was added and incubated with the cells during the IonWorks Quattro™ experiment. The final assay dilution was 200 and the final compound concentrations were in the range 50 μM to 50 nM.

Data Analysis

The recordings were analysed and filtered using both seal resistance (>20 MΩ) and peak current amplitude (>500 pA at the voltage step of 40 mV) in the absence of compound to eliminate unsuitable cells from further analysis. For hKv3.2 and hKv3.1 assays, paired comparisons of evoked currents between pre- and post-drug additions measured for the −15 mV voltage step were used to determine the positive modulation effect of each compound. Kv3 channel-mediated outward currents were measured determined from the mean amplitude of the current over the final 10 ms of the −15 mV voltage pulse minus the mean baseline current at −70 mV over a 10 ms period just prior to the −15 mV step. These Kv3 channel currents following addition of the test compound were then compared with the currents recorded prior to compound addition. Data were normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data were analysed using ActivityBase or Excel software. The concentration of compound required to increase currents by 50% of the maximum increase produced by the reference compound (EC$_{50}$) was determined by fitting of the concentration-response data using a four parameter logistic function in ActivityBase. For hKv3.3 assays, paired comparisons of evoked currents between pre- and post-drug additions were measured for the 0 mV step, considering the peak current and the decay (inactivation) of the current over the duration of the 0 mv test pulse (500 ms).

N-cyclohexyl-N-[(7,8-dimethyl-2-oxo-1,2-dihydro-3-quinolinyl)methyl]-N'-phenylurea was obtained from ASINEX (Registry Number: 552311-06-5).

All of the Example compounds were tested in the above hKv3.1 assay measuring potentiation of Kv3.1 and were identified as being Kv3.1 positive modulators. Kv3.1 positive modulators produce in the above assay an increase of whole-cell currents of, on average, at least 10%, and in many cases at least 20% of the increase observed with 50 micromolar N-cyclohexyl-N-[(7,8-dimethyl-2-oxo-1,2-dihydro-3-quinolinyl)methyl]-N'-phenylurea.

A secondary analysis of the data from the hKv3.1, hKv3.2 and hKv3.3 assays described in Example 1 may be used to investigate the effect of the compounds on rate of rise of the current from the start of the depolarising voltage pulses. The magnitude of the effect of a compound can be determined from the time constant (Tau$_{act}$) obtained from a non-linear fit, using the equation given below, of the rise in Kv3.1, Kv3.2 and Kv3.3 currents following the start of the −15 mV depolarising voltage pulse.

$$Y=(Y0-Y\max)*\exp(-K*X)+Y\max$$

where:
Y0 is the current value at the start of the depolarising voltage pulse;
Ymax is the plateau current;
K is the rate constant, and Tau$_{act}$ is the activation time constant, which is the reciprocal of K.

Similarly, the effect of the compounds on the time taken for Kv3.1, Kv3.2 or Kv3.3 currents to decay on closing of the channels at the end of the −15 mV depolarising voltage pulses can also be investigated. In this latter case, the magnitude of the effect of a compound on channel closing can be determined from the time constant (Tau$_{deact}$) of a non-linear fit of the decay of the current ("tail current") immediately following the end of the depolarising voltage pulse.

Kv3.1, Kv3.2 and Kv3.3 channels must activate and deactivate very rapidly in order to allow neurons to fire actions potentials at high frequency (Rudy et al., 2001). Slowing of activation is likely to delay the onset of action potential repolarisation; slowing of deactivation could lead to hyperpolarising currents that reduce the excitability of the neuron and delay the time before the neuron can fire a further action potential. Together these two slowing effects on channel activation and deactivation are likely to lead to a reduction rather than a facilitation of the neurons ability to fire at high frequencies. Thus compounds that have this slowing effect on the Kv3.1 and/or Kv3.2, and/or Kv3.3 channels will effectively behave as negative modulators of the channels, leading to a slowing of neuronal firing. This latter effect has been shown for certain of the compounds disclosed in WO2011/069951, where marked increases in $Tau_{act}$ can be observed from recordings made from "fast-firing" interneurons in the cortex of rat brain, using electrophysiological techniques, in vitro. The addition of the relevant compounds reduces the ability of the neurons to fire in response to trains of depolarising pulses at 300 Hz.

Therefore, although certain compounds may be identified act as positive modulators in the recombinant cell assay of Example 1, those compounds which markedly increase the value of $Tau_{act}$ can reduce the ability of neurons in native tissues to fire at high frequency.

Biological Example 2: Determination of Blood and Brain Tissue Binding

Materials and Methods

Rat whole blood, collected on the week of the experiment using K3-EDTA as an anti-coagulant, is diluted with isotonic phosphate buffer 1:1 (v/v). Rat whole brain, stored frozen at −20° C., is thawed and homogenised in artificial cerebrospinal fluid (CSF) 1:2 (w/v).

An appropriate amount of test compound is dissolved in DMSO to give a 5 millimolar solution. Further dilutions, to obtain a 166.7 micromolar working solution are then prepared using 50% acetonitrile in MilliQ water. This working solution is used to spike the blood to obtain a final concentration of 0.5 micromolar in whole blood. Similarly, the working solution is used to spike brain samples to obtain a final concentration of 5 micromolar in whole brain. From these spiked blood and brain preparations, control samples (n=3), are immediately extracted and used to calculate the initial recovery of the test items.

150 microL of compound-free buffer (isotonic phosphate buffer for blood or artificial CSF buffer for brain) is dispensed in one half-well and 150 microL of spiked matrix (blood or brain) is loaded in the other half-well, with the two halves separated by a semi-permeable membrane. After an equilibration period of 5 h at 37° C., 50 microL of dialysed matrix (blood or brain) is added to 50 microL of corresponding compound-free buffer, and vice-versa for buffer, such that the volume of buffer to matrix (blood or brain) remains the same. Samples are then extracted by protein precipitation with 300 microL of acetonitrile containing rolipram (control for positive ionization mode) or diclofenac (control for negative ionization mode) as internal standards and centrifuged for 10 min at 2800 rpm. Supernatants are collected (100 microL), diluted with 18% ACN in MilliQ water (200 microL) and then injected into an HPLC-MS/MS or UPLC-MS/MS system to determine the concentration of test compound present.

Analysis

Blood and brain tissue binding are then determined using the following formulas:

Afu=Buffer/Blood or Afu=CSF/Brain

Where Afu=apparent fraction unbound; Buffer=analyte/internal standard ratio determined in the buffer compartment; Blood=analyte/internal standard ratio determined in the blood compartment; Brain=analyte/internal standard ratio determined in the brain compartment.

$$Fucr = \frac{1/D}{[(1/Afu - 1) + 1/D]}$$

where: fucr=Fraction unbound corrected; D=matrix dilution factor (D=2 for blood and D=3 for brain).

Then:

% Binding=(1−fucr)×100

% Unbound=100−% Bound

Brain/Blood Partition Ratio (Kbb) Determination

For compounds freely permeable across the blood/brain barrier (BBB), the unbound concentrations in blood and brain would be equivalent under steady-state distribution conditions. Therefore, the Kbb value could be calculated as:

Fu(blood)/Fu(brain)

which is expected to be equivalent to the brain-to-blood concentration ratio (Ct(brain)/Ct(blood)) if efflux pump transporters are not involved.

Biological Example 3: Determination of In Vivo Pharmacokinetic Parameters

Materials and Methods

Adult male rats (Charles River, Italy) are dosed with test compound orally at 1 mg/kg (5 ml/kg, in 5% v/v DMSO, 0.5% w/v HPMC in water) and intravenously at 0.5 mg/kg (2 ml/kg, in 5% v/v DMSO 40% w/v PEG400 in saline). After oral administration, blood samples are collected under deep Isofluorane anesthesia from the portal vein and heart of each rat (1 rat per time point). After intravenous administration, serial blood samples are collected from the lateral tail vein of each rat. A further group of rats (n=1 per test compound) receive a single intravenous administration of the PgP transport inhibitor, Elacridar (3 mg/kg) shortly before the oral administration of the test compound at 1 mg/kg, as above. Blood and brain samples are collected at a single timepoint of 0.5 h after dose administration for these animals. In all cases, blood samples are collected into potassium EDTA tubes.

Blood and brain samples can be assayed for test compound concentration using a method based on protein precipitation with acetonitrile followed by HPLC/MS-MS analysis with an optimized analytical method.

Analysis

The concentrations of test compound in blood (expressed as ng/ml) and brain (expressed as ng/g) at the different time points following either oral or intravenous dosing are analysed using a non-compartmental pharmacokinetic model using WinNonLin Professional version 4.1. The following parameters are derived:

Intravenous dosing: Maximum concentration over time (Cmax), integrated concentration over time (AUC), clearance (Clb), volume of distribution (Vss) and half-life (t½).

Oral dosing: Cmax, time of maximum concentration (Tmax), AUC, bioavailability (F %), fraction absorbed (Fa %), blood to brain ratio (AUC BB), and Fold-change in AUC BB in the presence of Elacridar.

Compounds of the invention may be expected to demonstrate good availability in brain tissue.

Biological Example 4: Evaluation of the Effect of Modulators of Kv3.1/Kv3.2 Channels on Sensitivity to Mechanical and Cold Stimuli in Models of Neuropathic and Inflammatory Pain in the Rat The efficacy of the following compound was investigated using rat models of neuropathic and persistant inflammatory pain:
5,5-dimethyl-3-[2-(7-methylspiro[2H-benzofuran-3,1'-cyclopropane]-4-yl)oxypyrimidin-5-yl]imidazolidine-2,4-dione—Example 58 in WO2012/076877 (referred to herein as "Compound X").

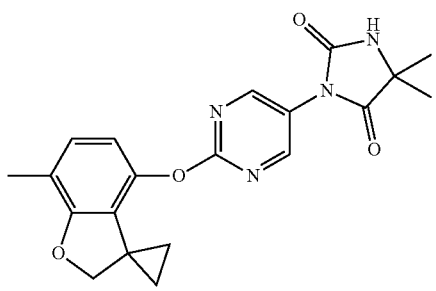

Materials and Methods

Subjects comprised male, Wistar Hanover rats, 6 animals per group (225±2 g).

Vehicle (12% Captisol®; 0.5% w/v HPMC and 0.1% w/v Tween-80; 5 ml/kg via the intraperitoneal route) was prepared using autoclaved deionized water not more than one week prior to use.

The details of the studies performed with 5,5-dimethyl-3-[2-(7-methylspiro[2H-benzofuran-3,1'-cyclopropane]-4-yl)oxypyrimidin-5-yl]imidazolidine-2,4-dione (Compound X) are outlined in Table 1.

TABLE 1

Dosing regimen for neuropathic and inflammatory pain models

| Compound | Neuropathic Pain | Inflammatory Pain |
|---|---|---|
| 5,5-dimethyl-3-[2-(7-methylspiro[2H-benzofuran-3,1'-cyclopropane]-4-yl)oxypyrimidin-5-yl]imidazolidine-2,4-dione (Compound X) | 10 mg/kg (i.p.)[1]<br>30 mg/kg (i.p.)<br>60 mg/kg (i.p.) | 10 mg/kg (i.p.)<br>30 mg/kg (i.p.)<br>60 mg/kg (i.p.) |

[1] (i.p.) intraperitoneal administration

The control for the neuropathic pain model was lamotrigine, administered at 30 mg/kg via oral delivery. The control for the inflammatory pain model was diclofenac, administered at 30 mg/kg via oral delivery. Statistical analysis was performed using one-way ANOVA, and comparisons were performed with time-matched vehicle group using Tukey's HSD test wherein *$p<0.05$, $p<0.01$, *$p<0.001$.

Experimental Protocol

All experimental procedures were approved by KCL ethical review, and carried out in accordance with the Home Office Animal Procedures Act (1986) and Project License (PPL 70/7510).

Treatment groups were randomised and blinded. Groups of 6 rats were used.

Neuropathic Pain

Neuropathic pain was induced by partial ligation of the sciatic nerve. Briefly, the rats were anaesthetised (isoflurane/$O_2$ inhalation), the left sciatic nerve exposed at mid-thigh level through a small incision and ⅓ to ½ of the nerve thickness tightly ligated within a 7.0 silk suture. The wound was closed with surgical glue. Animals were allowed to recover and tested 12-15 days following surgery.

Withdrawal thresholds were measured on both the ipsilateral (ligated) and contralateral (non-ligated) paws, prior to (predose) and then up to 24 h following drug or vehicle administration.

Pre-dose behavioural measurements were obtained by measuring paw withdrawals 14 days following nerve ligation; before the initiation of drug treatment. Following treatment, further readings were taken at 1, 3, 6 and 24 hour after administration.

Inflammatory Pain

Mechanical hyperalgesia was examined in a model of persistent inflammatory pain.

The hyperalgesia was induced by an intraplantar injection (25 μl) of Freund's Complete Adjuvant (FCA) into the left hind paw.

To assess the effect of the test compound, paw withdrawal thresholds were measured on both the ipsilateral (FCA-injected) and contralateral (non-injected) paws, prior to (naïve) and 24 h following FCA injection (predose), and then at 1, 3, 6 and 24 h after drug or vehicle administration.

Behavioural Tests

Mechanical hyperalgesia was examined in a model of neuropathic pain by measuring paw withdrawal thresholds (PWT) to increasing mechanical force applied to the dorsal surface of the rat paw using an Analgesymeter (Ugo-Basile, Milan) equipped with a wedge-shaped probe (area 1.75 $mm^2$). Cut-off was set at 250 g and the end-point was taken as withdrawal of the hind paw. Both ipsilateral and contralateral paw withdrawal readings were taken.

Cold sensitivity can be assessed using a commercially available cold-plate (Ugo Basile, Milan). The cold plate is allowed to stabilize for 5 minutes at the set temperature prior to testing. Paw withdrawal latencies (PWL) are determined with the cold-plate set at 10° C. The animals are lightly restrained and each hind paw in turn placed onto the surface of the cold-plate. The end point is taken as the withdrawal of the paw and recorded as the withdrawal latency for the ipsilateral and the contralateral paw. A maximum cut-off of 30 seconds is used for each paw.

General Observations

In addition to behavioural pain readings, each rat was observed throughout the study for changes in general behaviour.

Data Analysis

Neuropathic Pain

Data were expressed as withdrawal threshold (g) and percentage reversals calculated according to the following formula:

$$\% \text{ reversal} = \frac{\text{ipsilaterd threshold postdose} - \text{ipsilaterd threshold predose}}{\text{contralateral threshold predose} - \text{ipsilaterd threshold predose}} \times 100$$

Inflammatory Pain

Data were expressed as withdrawal threshold (g) and percentage reversals calculated according to the following formula:

$$\% \text{ reversal} = \left( \frac{\text{left postdose } PWT/L - \text{left predose } PWT/L}{\text{left naïve } PWT/L - \text{left predose } PWT/L} \right) \times 100$$

Statistical analysis was carried out on withdrawal threshold readings using ANOVA with repeated measures followed by Tukey's HSD test. The level for statistical significance was set as $p<0.05$.

Results

Neuropathic Pain Study

Partial ligation of the sciatic nerve resulted in a marked decrease in withdrawal threshold to a mechanical stimulus and in withdrawal latency to a cold stimulus of the affected paw. Fourteen days after nerve ligation, predose threshold readings of 66±1 g were measured in the ipsilateral paws compared to 104±1 g in the contralateral paws (FIG. 1a, FIG. 1b).

Figure 1C:
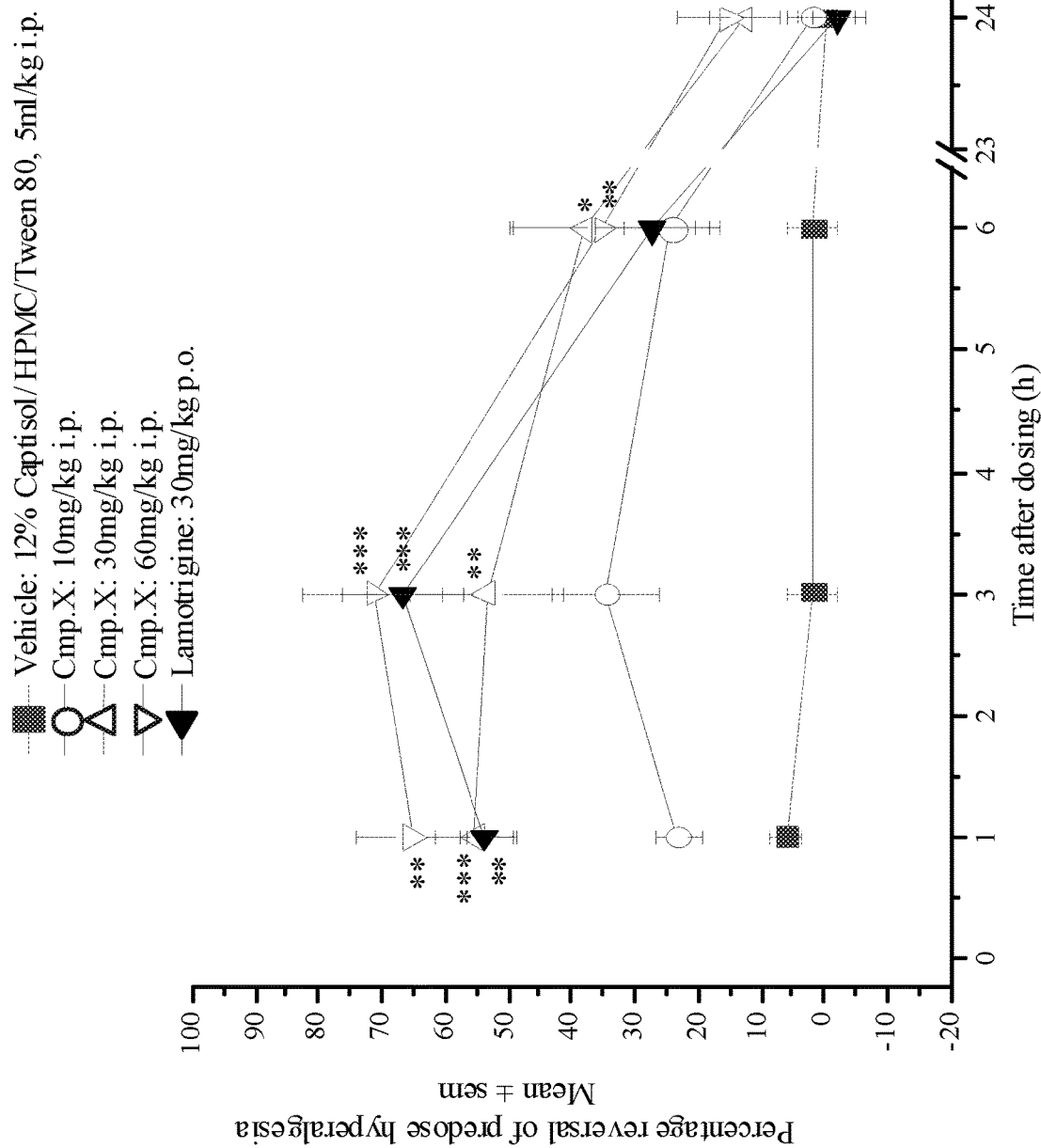

Compound X produced a dose-related reversal of mechanical sensitivity (FIG. 1a, FIG. 1c) with rapid onset and long duration of action.

Peak reversal of mechanical sensitivity was seen at 3 h post-dose (31% at 10 mg/kg, 73% at 30 mg/kg and 81% by 60 mg/kg). The positive control, lamotrigine, gave peak reversals at 3 h post-dose of 67%.

Inflammatory Pain Study

Figure 2A:
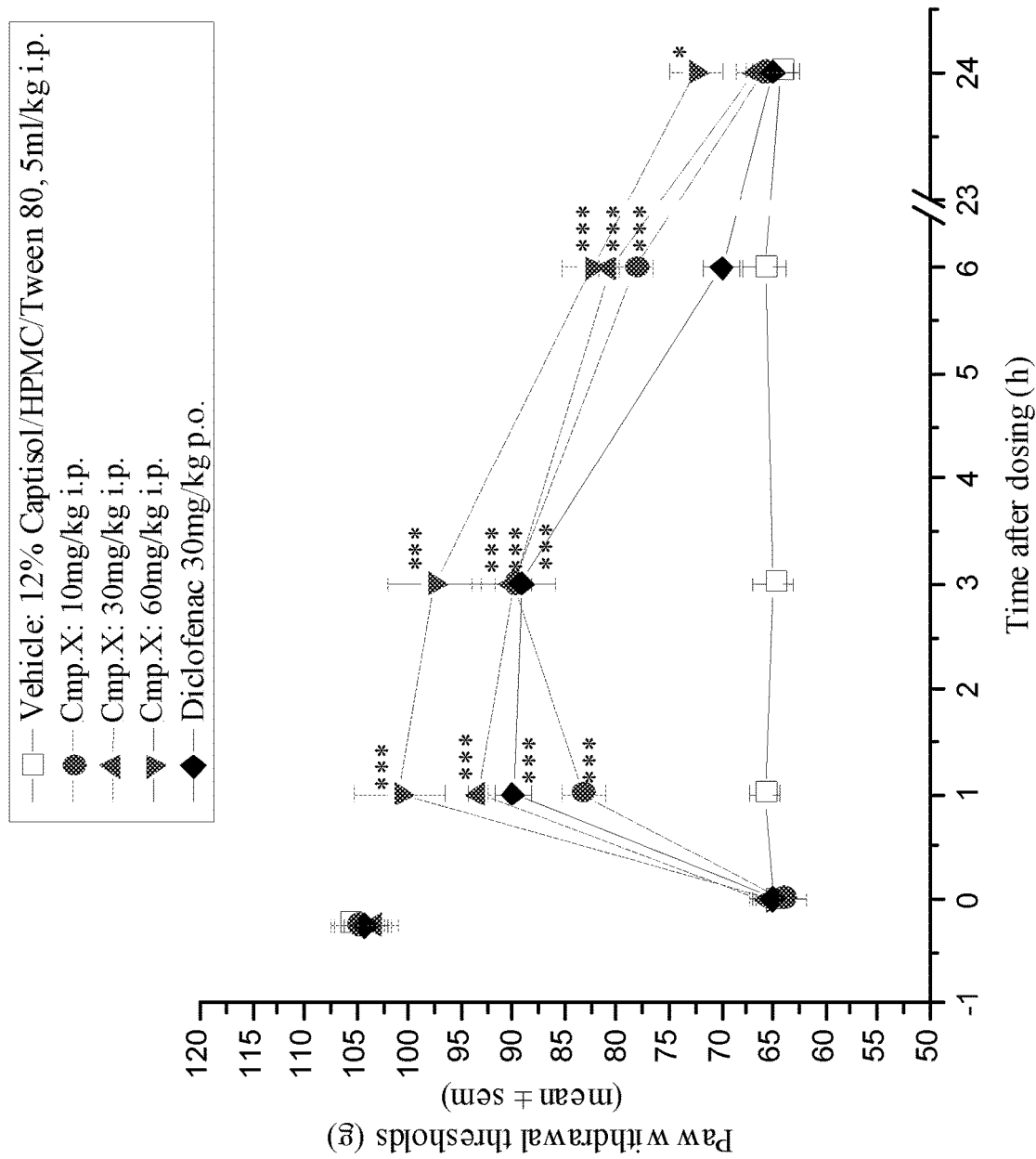
FIG. 2 shows the effect of Compound X on paw withdrawal thresholds under mechanical pressure in an inflammatory pain model: ipsilateral paw (FIG. 2a); contralateral paw (FIG. 2b); and percentage reversals (FIG. 2c).
Figure 2B:
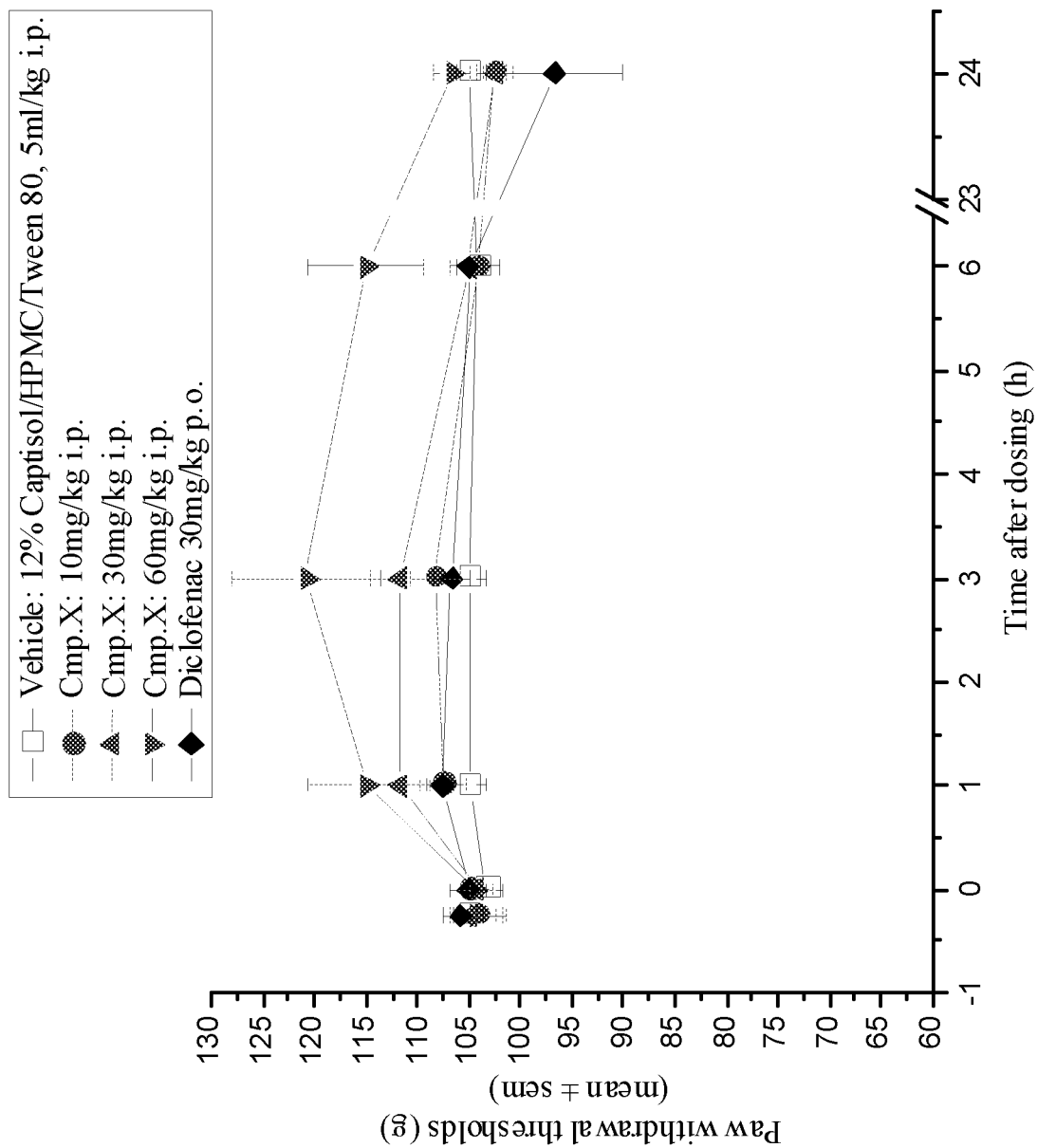

The intraplantar injection of FCA resulted in a marked decrease in withdrawal threshold to a mechanical stimulus of the affected paw. The mean naïve threshold readings were 105±1 g. 24 h after FCA injection, predose threshold readings of 65±1.0 g were measured in the ipsilateral paws compared to 104±1.0 g in the contralateral paws (FIG. 2a, FIG. 2b).

Figure 2C:
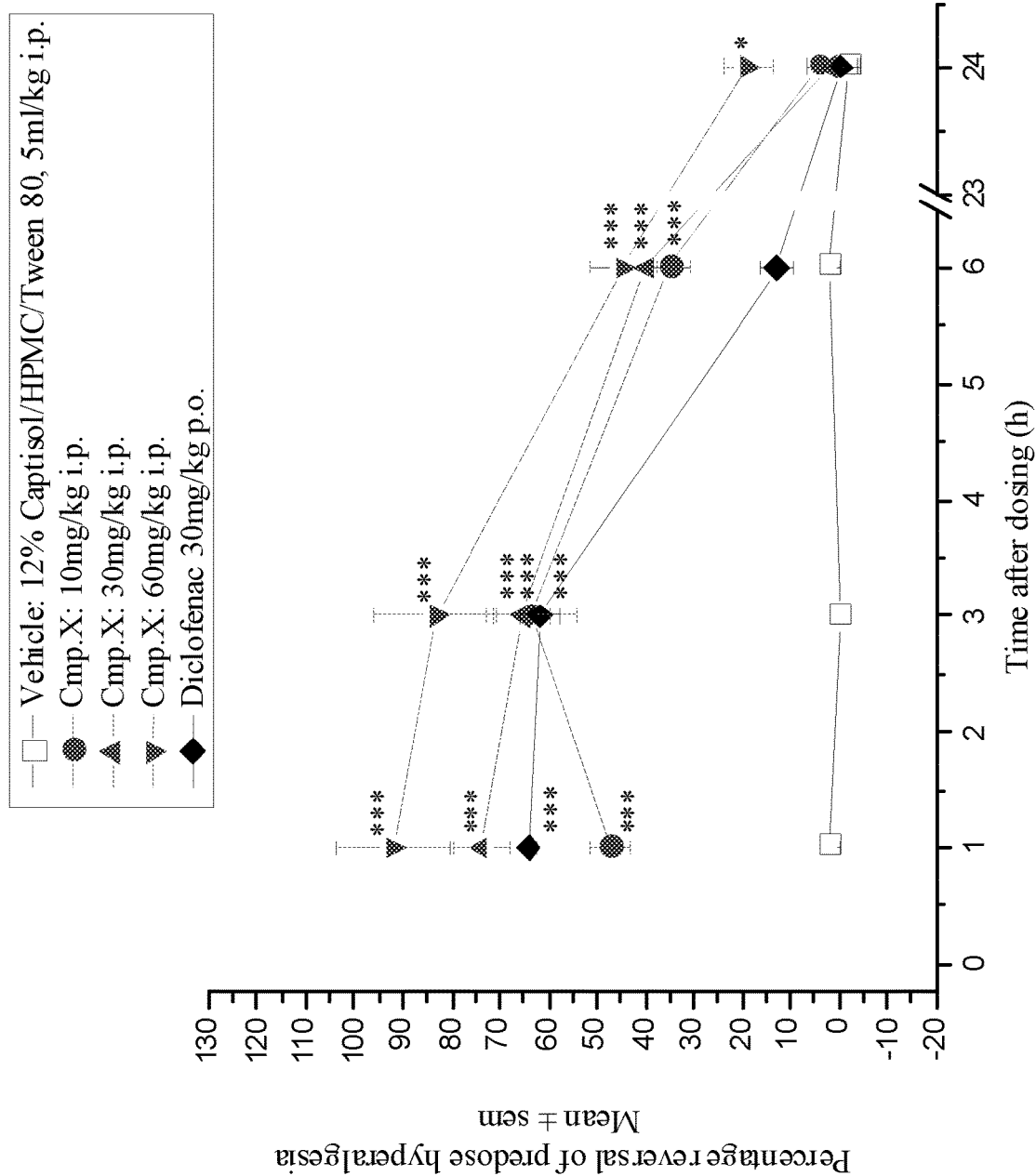

Compound X produced a dose-related reversal of mechanical sensitivity (FIG. 2a, FIG. 2c) with rapid onset of action and peak reversal at 1-3 h post-dose. Peak reversal of mechanical sensitivity was seen at 1 h post-dose for 30 mg/kg and 60 mg/kg (74% and 92% respectively) and at 3 h post-dose for 10 mg/kg (64% reversal). The reversal was long lasting with significant activity still evident at 6 h post-dose: mechanical sensitivity was reversed by 45% with 60 mg/kg. The positive control, diclofenac, gave peak reversals of 64% in mechanical (1 h post-dose).

Discussion

In a rat model of neuropathic pain induced by partial ligation of the sciatic nerve, administration of Compound X produced a marked, dose-related reversal of mechanical sensitivity in the ipsilateral paw. Compound X also produced a marked, dose-related reversal of cold sensitivity in the ipsilateral paw (results not shown here). The compound had a rapid onset of action with maximal efficacy seen at 1-3 h after dosing and long-lasting efficacy of up to 6 h. There were significant increases in the contralateral paw withdrawal thresholds to mechanical pressure. Significant increases in the contralateral paw withdrawal latencies to cold stimulation were also observed (results not shown here). The compound induced flaccidity in some of the treated rats. Compound X also markedly reversed the mechanical hyperalgesia induced in a model of persistent inflammatory pain. The same was observed for cold sensitivity in a model of persistent inflammatory pain (results not shown here). The compound effects were dose-related with a rapid onset of action, long duration of action and peak reversal at 1-3 h post-dose.

Conclusions

In a rat models of neuropathic and inflammatory pain, Compound X, which is a selective modulator of Kv3.1 and/or Kv3.2 and/or Kv3.3 channels, was effective at reversing behavioural measures of pain when administered acutely, but without causing significant changes in normal behaviour. These data strongly support the proposition that modulation of Kv3.1 and/or Kv3.2 and/or Kv3.3 channels has potential in the treatment of pain.

Biological Example 5: Comparison Between Cyclobutyl and Cyclopentyl Ring Systems Using the assay methods described previously, a compound of the invention featuring a cyclobutyl moiety was compared to a compound featuring a cyclopentyl moiety.

TABLE 1

Comparison between cyclobutyl and cyclopentyl ring systems

| Structure | pEC50 (Kv3.1) | N = | % current increase @ conc | | |
|---|---|---|---|---|---|
| | | | 1.56 µM | 3.12 µM | 12.5 µM |
| 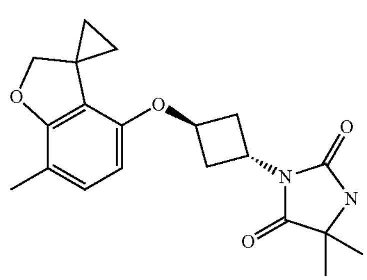 | 5.45 | >10 | 25 | 60 | 105 |

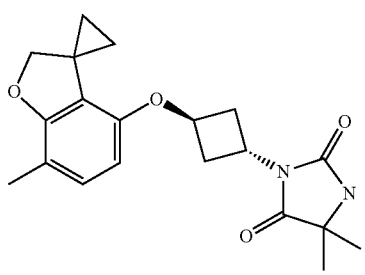

TABLE 1-continued

Comparison between cyclobutyl and cyclopentyl ring systems

| Structure | pEC50 (Kv3.1) | N = | % current increase @ conc | | |
|---|---|---|---|---|---|
| | | | 1.56 µM | 3.12 µM | 12.5 µM |
| [structure] | <4.3 | 4 | 7 | 10 | 12 |

From the comparative data in Table 1, it can be seen that the compound of the present invention is at least 10-fold more active than the corresponding cyclopentyl compound as shown by the pEC50 data.

Additional Animal Models

Patent applications WO2011/069951, WO2012/076877, WO2012/168710, WO2013/175215 and WO2013/182851 (all incorporated by reference) demonstrate the activity of compounds which are modulators of Kv3.1 and Kv3.2 in animal models of seizure, hyperactivity, sleep disorders, psychosis, hearing disorders and bipolar disorders.

Patent application WO2013/175211 (incorporated by reference) demonstrates the efficacy of a compound which is a modulator of Kv3.1 and Kv3.2 in a model of acute noise-induced hearing loss in the chinchilla, and also evaluates the efficacy of the compound in a model of central auditory processing deficit and in a model of tinnitus.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

REFERENCES

All publications, including but not limited to patents and patent applications, cited in this specification are herein incorporated by reference as if each individual publication were specifically and individually indicated to be incorporated by reference herein as though fully set forth.

Aroniadou-Anderjaska V, Qashu F, Braga M F M. Mechanisms regulating GABAergic inhibitory transmission in the basolateral amygdala: implications for epilepsy and anxiety disorders. *Amino Acids* 2007 August; 32:305-315.

Baranauskas G, Nistri A. Sensitization of pain pathways in the spinal cord: cellular mechanisms. *Prog. Neurobiol.* 1998 February; 54(3):349-65.

Baron R, Hans G, Dickenson A H. Peripheral input and its importance for central sensitization. *Ann. Neurol.* 2013 November; 74(5):630-6.

Ben-Ari Y. Seizure Beget Seizure: The Quest for GABA as a Key Player. *Crit. Rev. Neurobiol.* 2006; 18(1-2):135-144.

Benes F M, Lim B, Matzilevich D, Subburaju S, Walsh J P. Circuitry-based gene expression profiles in GABA cells of the trisynaptic pathway in schizophrenics versus bipolars. *PNAS* 2008 December; 105(52):20935-20940.

Bennett D L, Woods C G. Painful and painless channelopathies. *Lancet Neurol.* 2014 June; 13(6):587-99.

Berge S, Bighley L, Monkhouse D. Pharmaceutical Salts. *J. Pharm. Sci.* 1977; 66; 1-19.

Brambilla P, Perez J, Schettini G, Soares J C. GABAergic dysfunction in mood disorders. *Mol. Psych.* 2003 April; 8:721-737.

Brooke R E, Pyner S, McLeish P, Buchan S, Deuchars J, Deuchars S A. Spinal cord interneurones labelled trans-neuronally from the adrenal gland by a GFP-herpes virus construct contain the potassium channel subunit Kv3.1b. *Auton. Neurosci.* 2002 June; 98(1-2):45-50.

Brooke R E, Atkinson L, Batten T F, Deuchars S A, Deuchars J. Association of potassium channel Kv3.4 subunits with pre- and post-synaptic structures in brainstem and spinal cord. *Neuroscience* 2004; 126(4):1001-10.

Brooke R E, Atkinson L, Edwards I, Parson S H, Deuchars J. Immunohistochemical localisation of the voltage gated potassium ion channel subunit Kv3.3 in the rat medulla oblongata and thoracic spinal cord. *Brain Res.* 2006 January; 1070(1):101-15.

Cervero F. Spinal cord hyperexcitability and its role in pain and hyperalgesia. *Exp. Brain Res.* 2009 June; 196(1):129-37.

Chang S Y, Zagha E, Kwon E S, Ozaita A, Bobik M, Martone M E, Ellisman M H, Heintz N, Rudy B. Distribution of Kv3.3 Potassium Channel Subunits in Distinct Neuronal Populations of Mouse Brain. *J. Comp. Neuro.* 2007 February; 502:953-972.

Chien L Y, Cheng J K, Chu D, Cheng C F, Tsaur M L. Reduced expression of A-type potassium channels in primary sensory neurons induces mechanical hypersensitivity. *J. Neurosci.* 2007 September; 27(37):9855-65.

Chow A, Erisir A, Farb C, Nadal M S, Ozaita A, Lau D, Welker E, Rudy B. $K^+$ Channel Expression Distinguishes Subpopulations of Parvalbumin- and Somatostatin-Containing Neocortical Interneurons. *J. Neurosci.* 1999 November; 19(21):9332-9345.

Desai R, Kronengold J, Mei J, Forman S, Kaczmarek L. Protein Kinase C Modulates Inactivation of Kv3.3 Channels. *J. Biol. Chem.* 2008; 283; 22283-22294.

Deuchars S A, Brooke R E, Frater B, Deuchars J. Properties of interneurones in the intermediolateral cell column of the rat spinal cord: role of the potassium channel subunit Kv3.1. *Neuroscience* 2001; 106(2):433-46.

Devulder J. Flupirtine in pain management: pharmacological properties and clinical use. CNS Drugs 2010 October; 24(10):867-81.

Dib-Hajj S D, Yang Y, Black J A, Waxman S G. The Na(V)1.7 sodium channel: from molecule to man. *Nat. Rev. Neurosci.* 2013 January; 14(1):49-62.

Diochot S, Schweitz H, Beress L, Lazdunski M. Sea Anemone Peptides with a Specific Blocking Activity against the Fast Inactivating Potassium Channel Kv3.4. *J. Biol. Chem.* 1998 March; 273(12); 6744-6749.

Engel A K, Fries P, Singer W. Dynamic Predictions: Oscillations and Synchrony in Top-Down Processing. *Nat. Rev. Neurosci.* 2001 October; 2(10):704-716.

Espinosa F, McMahon A, Chan E, Wang S, Ho C S, Heintz N, Joho R H. Alcohol Hypersensitivity, Increased Locomotion, and Spontaneous Myoclonus in Mice Lacking the Potassium Channels Kv3.1 and Kv3.3. *J. Neurosci.* 2001 September; 21(17):6657-6665.

Espinosa F, Torres-Vega M A, Marks G A, Joho R H. Ablation of Kv3.1 and Kv3.3 Potassium Channels Disrupts Thalamocortical Oscillations In Vitro and In Vivo. *J. Neurosci.* 2008 May; 28(21):5570-5581.

Figueroa K, Minassian N, Stevanin G, Waters M, Garibyan V, Forlani S, Strzelczyk A, Burk K, Brice A, Durr A, Papazian D, Pulst S. KCNC3: phenotype, mutations, channel biophysics—a study of 260 familial ataxia patients. Human Mutation. 2010; 31; 191-196.

Finnerup N B, Attal N, Haroutounian S, McNicol E, Baron R, Dworkin R H, Gilron I, Haanpää M, Hansson P, Jensen T S, Kamerman P R, Lund K, Moore A, Raja S N, Rice A S, Rowbotham M, Sena E, Siddall P, Smith B H, Wallace M. Pharmacotherapy for neuropathic pain in adults: a systematic review and meta-analysis. *Lancet Neurol.* 2015 February; 14(2):162-73.

Fisahn A. Kainate receptors and rhythmic activity in neuronal networks: hippocampal gamma oscillations as a tool. *J. Physiol.* 2005 October; 561(1):65-72.

Greene T W, Wuts, P G. Greene's Protective Groups in Organic Synthesis, 2006, 4th Edition, John Wiley & Sons, Inc., Hoboken, N.J., USA.

Joho R H, Ho C S, Marks G A. Increased γ- and Decreased δ-Oscillations in a Mouse Deficient for a Potassium Channel Expressed in Fast-Spiking Interneurons. *J. Neurophysiol.* 1999 June; 82:1855-1864.

Joho R H, Hurlock E C. The Role of Kv3-type Potassium Channels in Cerebellar Physiology and Behavior. *Cerebellum* 2009 February; 8:323-333.

Jung D, Lee S, Kim D, Joo K, Cha C, Yang H, Lee W, Chung Y. Age-related changes in the distribution of Kv1.1 and Kv3.1 in rat cochlear nuclei. *Neurol. Res.* 2005; 27; 436-440.

Kasten M R, Rudy B, Anderson M P. Differential regulation of action potential firing in adult murine thalamocortical neurons by Kv3.2, Kv1, and SK potassium and N-type calcium channels. *J. Physiol.* 2007; 584(2):565-582.

Kaczmarek L, Bhattacharjee A, Desai R, Gan L, Song P, von Hehn C, Whim M, Yang B. Regulation of the timing of MNTB neurons by short-term and long-term modulation of potassium channels. *Hearing Res.* 2005; 206; 133-145.

Lau D, Vega-Saenz de Miera E, Contreras D, Ozaita A, Harvey M, Chow A, Noebels J L, Paylor R, Morgan J I, Leonard C S, Rudy B. Impaired Fast-Spiking, Suppressed Cortical Inhibition, and Increased Susceptibility to Seizures in Mice Lacking Kv3.2 K$^+$ Channel Proteins. *J. Neurosci.* 2000 December; 20(24):9071-9085.

Li W, Kaczmarek K, Perney T M. Localization of Two High-Threshol Potassium Channel Subunits in the Rat Central Auditory System. *J. Comp. Neuro.* 2001 May; 437:196-218.

Lu R, Bausch A E, Kallenborn-Gerhardt W, Stoetzer C, Debruin N, Ruth P, Geisslinger G, Leffler A, Lukowski R, Schmidtko A. Slack channels expressed in sensory neurons control neuropathic pain in mice. *J. Neurosci.* 2015 January; 35(3):1125-35.

Markram H, Toledo-Rodriguez M, Wang Y, Gupta A, Silberberg, Wu C. Interneurons of the neocortical inhibitory system. *Nat. Rev. Neurosci.* 2004 October; 5:793-807.

Martina M, Schultz J H, Ehmke H, Monyer H, Jonas P. Functional and Molecular Differences between Voltage-Gated K$^+$ Channels of Fast-Spiking Interneurons and Pyramidal Neurons of Rat Hippocampus. *J. Neurosci.* 1998 October; 18(20):8111-8125.

McCarberg B H, Nicholson B D, Todd K H, Palmer T, Penles L. The impact of pain on quality of life and the unmet needs of pain management: results from pain sufferers and physicians participating in an Internet survey. *Am. J. Ther.* 2008 July-August; 15(4):312-20.

McDonald A J, Mascagni F. Differential expression of Kv3.1b and Kv3.2 potassium channel subunits in interneurons of the basolateral amygdala. *Neuroscience* 2006; 138:537-547.

McMahon A, Fowler S C, Perney T M, Akemann W, Knopfel, Joho R H. Allele-dependent changes of olivocerebellar circuit properties in the absence of the voltage-gated potassium channels Kv3.1 and Kv3.3. *Eur. J. Neurosci.* 2004 March; 19:3317-3327.

Mitchell I, Drew A, Ribich S, Rioux N, Swinger K, Jacques S, Lingaraj T, Boriack-Sjodin P, Waters N, Wigle T, Moradei O, Jin L, Riera T, Porter-Scott M, Moyer M, Smith J, Chesworth R, Copeland R. Aryl Pyrazoles as Potent Inhibitors of Arginine Methyltransferases: Identification of the First PRMT6 Tool Compound. *ACS Med. Chem. Lett.* 2015; 6(6); 655-659.

Pilati N, Large C, Forsythe I, Hamann M. Acoustic over-exposure triggers burst firing in dorsal cochlear nucleus fusiform cells. *Hearing Research* 2012; 283; 98-106.

Puente N, Mendizabal-Zubiaga J, Elezgarai I, Reuero L, Buceta I, Grandes P. Precise localization of the voltage-gated potassium channel subunits Kv3.1b and Kv3.3 revealed in the molecular layer of the rat cerebellar cortex by a pre-embedding immunogold method. *Histochem. Cell. Biol.* 2010 September; 134:403-409.

Reynolds G P, Abdul-Monim Z, Neill J C, Zhang Z J. Calcium Binding Protein Markers of GABA Deficits in Schizophrenia—Post Mortem Studies and Animal Models. *Neurotox. Res.* 2004 February; 6(1):57-62.

Ritter D M, Ho C, O'Leary M E, Covarrubias M. Modulation of Kv3.4 channel N-type inactivation by protein kinase C shapes the action potential in dorsal root ganglion neurons. *J. Physiol.* 2012 January; 590(Pt 1):145-61.

Ritter D M, Zemel B M, Hala T J, O'Leary M E, Lepore A C, Covarrubias M. Dysregulation of Kv3.4 channels in dorsal root ganglia following spinal cord injury. *J. Neurosci.* 2015 January; 35(3):1260-73.

Roberts L, Eggermont J, Caspary D, Shore S, Melcher J, Kaltenback J. Ringing Ears: The Neuroscience of Tinnitus. *J. Neurosci.* 2010:30(45); 14972-14979.

Rudy B, McBain C J. Kv3 channels: voltage-gated K+ channels designed for high-frequency repetitive firing. *TRENDS in Neurosci.* 2001 September; 24(9):517-526.

Sacco T, de Luca A, Tempia F. Properties and expression of Kv3 channels in cerebellar Purkinje cells. *Mol. Cell. Neurosci.* 2006 July; 33:170-179.

Schulz P, Steimer T. Neurobiology of Circadian Systems. *CNS Drugs* 2009; 23(Suppl. 2):3-13.

Song P, Yang Y, Barnes-Davies M, Bhattacharjee A, Hamann M, Forsythe I D, Oliver D L, Kaczmarek L K. Acoustic environment determines phosphorylation state of the Kv3.1 potassium channel in auditory neurons *Nat. Neurosci.* 2005 October; 8(10): 1335-1342.

Spencer K M, Nestor P G, Perlmutter R, Niznikiewicz M A, Klump M C, Frumin M, Shenton M E, McCarley R W. Neural synchrony indexes disordered perception and cognition in schizophrenia. *PNAS* 2004 December; 101(49): 17288-17293.

Sun S, Cohen C J, Dehnhardt C M. Inhibitors of voltage-gated sodium channel Nav1.7: patent applications since 2010. *Pharm. Pat. Anal.* 2014 September; 3(5):509-21.

U.S. Department of Health and Human Services, Food and Drug Administration. Draft Guidance for Industry Analgesic Indications: Developing Drug and Biological Products: http://www.fda.gov/downloads/drugs/guidancecompliance regulatory information/guidances/ucm384691.pdf 2014 February.

von Hehn C, Bhattacharjee A, Kaczmarek L. Loss of Kv3.1 Tonotopicity and Alterations in cAMP Response Element-Binding Protein Signaling in Central Auditory Neurons of Hearing Impaired Mice. *J. Neurosci.* 2004; 24: 1936-1940.

Weiser M, Vega-Saenz de Miera E, Kentros C, Moreno H, Franzen L, Hillman D, Baker H, Rudy B. Differential Expression of Shaw-related K+ Channels in the Rat Central Nervous System. *J. Neurosci.* 1994 March; 14(3):949-972.

Wickenden A D, McNaughton-Smith G. Kv7 channels as targets for the treatment of pain. *Curr. Pharm. Des.* 2009; 15(15):1773-98.

Woolf C J. What is this thing called pain? *J. Clin. Invest.* 2010 November; 120(11):3742-4.

Woolf C J. Central sensitization: implications for the diagnosis and treatment of pain. *Pain* 2011 March; 152(3 Suppl):S2-15.

Yeung S Y M, Thompson D, Wang Z, Fedida D, Robertson B. Modulation of Kv3 Subfamily Potassium Currents by the Sea Anemone Toxin BDS: Significance for CNS and Biophysical Studies. *J. Neurosci.* 2005 March; 25(38): 8735-8745.

Zamponi G W, Striessnig J, Koschak A, Dolphin A C. *Pharmacol Rev.* 2015 October; 67(4):821-70.

The invention claimed is:

1. A compound of formula (I):

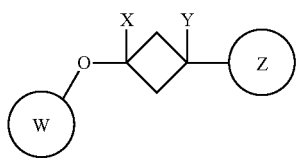

(I)

wherein:

X is H or CH$_3$;

Y is H or CH$_3$;

wherein at least one of X and Y is H;

W is group (Wa), group (Wb) or group (Wc):

wherein group (Wa) and group (Wb) are:

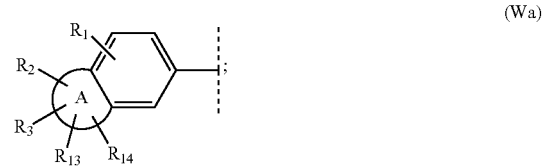

(Wa)

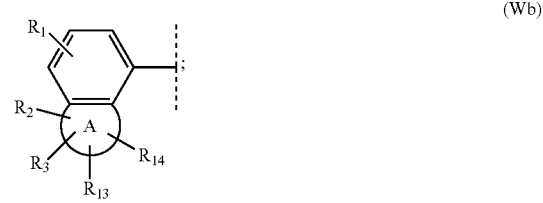

(Wb)

wherein:

$R_1$ is H, $C_{1-4}$alkyl, halo, halo$C_{1-4}$alkyl, CN, $C_{1-4}$alkoxy or halo$C_{1-4}$alkoxy;

$R_2$ is H, $C_{1-4}$alkyl, C3-5 spiro carbocyclyl, halo $C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

$R_{14}$ is H, $C_{1-4}$alkyl, halo$C_{1-4}$alkyl, halo; or $R_{14}$ is absent;

A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;

wherein $R_2$ and $R_3$ may be attached to the same or a different ring atom; $R_2$ may be attached to a fused ring atom; and wherein $R_{13}$ and $R_{14}$ may be attached to the same or a different ring atom;

wherein group (Wc) is:

(Wc)

wherein:

$R_{16}$ is halo, $C_{1-4}$alkyl, $C_{1-4}$alkoxy, halo$C_{1-4}$alkyl, halo$C_{1-4}$alkoxy or CN;

$R_{17}$ is H, halo, CN, $C_{1-4}$alkyl, $C_{1-4}$alkoxy or halo $C_{1-4}$alkoxy;

$R_{18}$ is H, halo, CN, $C_{1-4}$alkyl or $C_{1-4}$alkoxy;

Z is group (Za) or (Zb):
wherein group (Za) is:

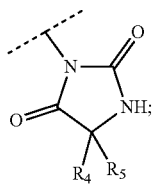
(Za)

wherein:
R$_4$ is H or C$_{1-4}$ alkyl;
R$_5$ is H or C$_{1-4}$ alkyl; or
R$_4$ and R$_5$ can be fused to form a C$_{3-5}$ spiro carbocyclyl or a C$_{2-5}$ spiro heterocyclyl;
and wherein group (Zb) is:

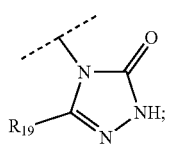
(Zb)

wherein:
R$_{19}$ is C$_{1-4}$ alkyl;
or a pharmaceutically acceptable salt and/or solvate thereof and/or derivative thereof, wherein the derivative is a pharmaceutically acceptable prodrug formed by functionalising the secondary nitrogen of the hydantoin or triazolone with a group L as illustrated below:

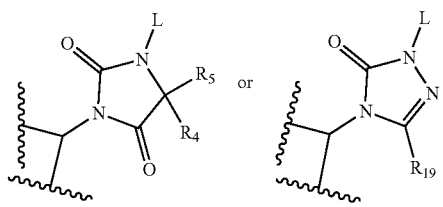

wherein L is selected from the groups consisting of:
a) —PO(OH)O$^-$.M$^+$,
b) —PO(O$^-$)$_2$.2M$^+$,
c) —PO(O$^-$)$_2$.D$^{2+}$, wherein D$^{2+}$ is a pharmaceutically acceptable divalent counterion,
d) —CH(R$^X$)—PO(OH)O$^-$.M$^+$, wherein R$^X$ is hydrogen or C$_{1-3}$ alkyl,
e) —CH(R$^X$)—PO(O$^-$)$_2$.2M$^+$,
f) —CH(R$^X$)—PO(O$^-$)$_2$.D$^{2+}$,
g) —SO$_3^-$.M$^+$,
h) —CH(R$^X$)—SO$_3^-$.M$^+$, and
i) —CO—CH$_2$CH$_2$—CO$_2$.M$^+$,
wherein M$^+$ is a pharmaceutically acceptable monovalent counterion.

2. The compound according to claim 1, wherein R$_4$ is C$_{1-4}$ alkyl; R$_5$ is H or C$_{1-4}$ alkyl; or R$_4$ and R$_5$ can be fused to form a C$_{3-5}$ spiro carbocyclyl or a C$_{2-4}$ spiro heterocyclyl; or a pharmaceutically acceptable salt and/or solvate thereof and/or derivative thereof.

3. The compound according to claim 1, wherein X and Y are both H.

4. The compound according to claim 1, wherein Z is group (Za).

5. The compound according to claim 1, wherein Z is group (Zb).

6. The compound according to claim 1, wherein R$_{19}$ is methyl.

7. The compound according to claim 1, wherein W is group (Wa).

8. The compound according to claim 1, wherein W is group (Wb).

9. The compound according to claim 1, wherein R$_1$ is H, methyl or CN.

10. The compound according to claim 1, wherein R$_2$ is methyl or halo.

11. The compound according to claim 1, wherein R$_3$ is methyl or halo.

12. The compound according to claim 1, wherein R$_{13}$ is H or is absent and is suitably absent.

13. The compound according to claim 1, wherein R$_{14}$ is H or is absent and is suitably absent.

14. The compound according to claim 1, wherein ring A is selected from the group consisting of:

15. The compound according to claim 1, wherein W is group (Wc).

16. The compound according to claim 1, wherein $R_{16}$ is methyl, ethyl, propyl, butyl, cyclopropyl, chloro, fluoro, methoxy, ethoxy, propoxy, trifluoromethyl, trifluoromethoxy or CN.

17. The compound according to claim 1, wherein $R_{17}$ is methyl, ethyl, propyl, butyl, cyclopropyl, chloro, fluoro, methoxy, ethoxy, propoxy, trifluoromethoxy or CN.

18. The compound according to claim 1, selected from the group consisting of:
- syn-5,5-dimethyl-3-[3-[4-methyl-3-(trifluoromethoxy) phenoxy]cyclobutyl]imidazolidine-2,4-dione (Example 1);
- syn-5,5-dimethyl-3-[3-(7-methylspiro[2H-benzofuran-3,1'-cyclopropane]-4-yl)oxycyclobutyl]imidazolidine-2,4-dione (Example 2);
- syn-4-[3-(4,4-dimethyl-2,5-dioxo-imidazolidin-1-yl)cyclobutoxy]-2-isopropyl-benzonitrile (Example 3);
- anti-5,5-dimethyl-3-[3-[4-methyl-3-(trifluoromethoxy) phenoxy] cyclobutyl]imidazolidine-2,4-dione (Example 4);
- anti-5,5-dimethyl-3-[3-(7-methylspiro[2H-benzofuran-3,1'-cyclopropane]-4-yl)oxycyclobutyl]imidazolidine-2,4-dione (Example 5);
- anti-4-[3-(4,4-dimethyl-2,5-dioxo-imidazolidin-1-yl)cyclobutoxy]-2-isopropyl-benzonitrile (Example 6);
- syn-5,5-dimethyl-3-[3-[3-(trifluoromethoxy)phenoxy]cyclobutyl]imidazolidine-2,4-dione (Example 7);
- anti-5,5-dimethyl-3-[3-[3-(trifluoromethoxy)phenoxy] cyclobutyl]imidazolidine-2,4-dione (Example 8);
- syn-3-[3-(2-tert-butylphenoxy)cyclobutyl]-5,5-dimethyl-imidazolidine-2,4-dione (Example 9);
- anti-3-[3-(2-tert-butylphenoxy)cyclobutyl]-5,5-dimethyl-imidazolidine-2,4-dione (Example 10),
- syn-3-tert-butyl-4-[3-(4,4-dimethyl-2,5-dioxo-imidazolidin-1-yl)cyclobutoxy]benzonitrile (Example 11);
- anti-3-tert-butyl-4-[3-(4,4-dimethyl-2,5-dioxo-imidazolidin-1-yl)cyclobutoxy]benzonitrile (Example 12);
- syn-4-[3-(4,4-dimethyl-2,5-dioxo-imidazolidin-1-yl)cyclobutoxy]-2-(trifluoromethoxy)benzonitrile (Example 13);
- anti-4-[3-(4,4-dimethyl-2,5-dioxo-imidazolidin-1-yl)cyclobutoxy]-2-(trifluoromethoxy)benzonitrile (Example 14);
- anti-5,5-dimethyl-3-(3-spiro[2H-benzofuran-3,1'-cyclopropane]-4-yloxycyclobutyl)imidazolidine-2,4-dione (Example 15);
- syn-5,5-dimethyl-3-(3-spiro[2H-benzofuran-3,1'-cyclopropane]-4-yloxycyclobutyl)imidazolidine-2,4-dione (Example 16);
- syn-(5R)-5-ethyl-3-[3-(7-methylspiro[2H-benzofuran-3,1'-cyclopropane]-4-yl)oxycyclobutyl]imidazolidine-2,4-dione (Example 17);
- anti-(5R)-5-ethyl-3-[3-[4-methyl-3-(trifluoromethoxy) phenoxy]cyclobutyl]imidazolidine-2,4-dione (Example 18);
- anti-(5R)-5-ethyl-3-[3-(7-methylspiro[2H-benzofuran-3,1'-cyclopropane]-4-yl)oxycyclobutyl]imidazolidine-2,4-dione (Example 19);
- syn-(5S)-5-ethyl-3-[3-(7-methylspiro[2H-benzofuran-3,1'-cyclopropane]-4-yl)oxycyclobutyl]imidazolidine-2,4-dione (Example 20);
- anti-(5S)-5-ethyl-3-[3-[4-methyl-3-(trifluoromethoxy) phenoxy]cyclobutyl]imidazolidine-2,4-dione (Example 21);
- anti-(5S)-5-ethyl-3-[3-(7-methylspiro[2H-benzofuran-3,1'-cyclopropane]-4-yl)oxycyclobutyl]imidazolidine-2,4-dione (Example 22);
- syn-3-methyl-4-[3-(7-methylspiro[2H-benzofuran-3,1'-cyclopropane]-4-yl)oxycyclobutyl]-1H-1,2,4-triazol-5-one (Example 23); and
- anti-3-methyl-4-[3-(7-methylspiro[2H-benzofuran-3,1'-cyclopropane]-4-yl)oxycyclobutyl]-1H-1,2,4-triazol-5-one (Example 24);
- 4-[3-(4,4-dimethyl-2,5-dioxo-imidazolidin-1-yl)cyclobutoxy]spiro[2H-benzofuran-3,1'-cyclopropane]-7-carbonitrile (Example 25);
- 6-[3-(7-methylspiro[2H-benzofuran-3,1'-cyclopropane]-4-yl)oxycyclobutyl]-2-oxa-6,8-diazaspiro[3.4]octane-5,7-dione (Example 26);
- 3-[3-(7-methylspiro[2H-benzofuran-3,1'-cyclopropane]-4-yl)oxycyclobutyl]imidazolidine-2,4-dione (Example 27);
- (5S)-5-methyl-3-[3-(7-methylspiro[2H-benzofuran-3,1'-cyclopropane]-4-yl)oxycyclobutyl]imidazolidine-2,4-dione (Example 28); and
- (5R)-5-methyl-3-[3-(7-methylspiro[2H-benzofuran-3,1'-cyclopropane]-4-yl)oxycyclobutyl]imidazolidine-2,4-dione (Example 29);

or a pharmaceutically acceptable salt and/or solvate thereof and/or derivative thereof.

\* \* \* \* \*